US010770276B2

(12) United States Patent
Kibbey et al.

(10) Patent No.: US 10,770,276 B2
(45) Date of Patent: Sep. 8, 2020

(54) TECHNIQUES OF MASS SPECTROMETRY FOR ISOTOPOMER ANALYSIS AND RELATED SYSTEMS AND METHODS

(71) Applicant: Yale University, New Haven, CT (US)

(72) Inventors: Richard Kibbey, Hamden, CT (US); Tiago Cardoso Alves, New Haven, CT (US); Graeme F. Mason, Guilford, CT (US)

(73) Assignee: Yale University, New Haven, CT (US)

( * ) Notice: Subject to any disclaimer, the term of this patent is extended or adjusted under 35 U.S.C. 154(b) by 326 days.

(21) Appl. No.: 15/755,641

(22) PCT Filed: Aug. 30, 2016

(86) PCT No.: PCT/US2016/049438
§ 371 (c)(1),
(2) Date: Feb. 27, 2018

(87) PCT Pub. No.: WO2017/040498
PCT Pub. Date: Mar. 9, 2017

(65) Prior Publication Data
US 2020/0234938 A1    Jul. 23, 2020

Related U.S. Application Data

(60) Provisional application No. 62/212,343, filed on Aug. 31, 2015.

(51) Int. Cl.
*H01J 49/26* (2006.01)
*H01J 49/00* (2006.01)
(Continued)

(52) U.S. Cl.
CPC ........ *H01J 49/0045* (2013.01); *G01N 27/622* (2013.01); *G01N 33/6848* (2013.01);
(Continued)

(58) Field of Classification Search
CPC ............... H01J 49/0045; H01J 49/0031; H01J 49/0036; H01J 49/421; G01N 33/6848; G01N 27/622
(Continued)

(56) References Cited

U.S. PATENT DOCUMENTS 8,129,335 B2 *   3/2012   Hellerstein ........ A61K 49/0002
                                                    514/1.1
2012/0237937 A1   9/2012   Fan et al.
(Continued)

FOREIGN PATENT DOCUMENTS

| CA | 2 494 715 C | 2/2004 |
| WO | WO 2003/029425 A2 | 4/2003 |
| WO | WO 2008/025016 A2 | 2/2008 |

OTHER PUBLICATIONS

International Search Report and Written Opinion dated Nov. 14, 2016 in connection with International Application No. PCT/US2016/049438.
(Continued)

*Primary Examiner* — Nicole M Ippolito
(74) *Attorney, Agent, or Firm* — Wolf, Greenfield & Sacks, P.C.

(57) ABSTRACT

According to some aspects, a spectrometer is provided, the spectrometer configured to receive molecules of a plurality of metabolites including one or more molecules of a first metabolite, filter the received molecules to retain molecules of the first metabolite including a plurality of different mass isotopomers of the first metabolite, fragment molecules of a first mass isotopmer of the retained molecules to produce a first plurality of daughter ions, measure abundances of the first plurality of daughter ions as a function of daughter ion mass, fragment molecules of a second istopomer, different from the first mass isotopmer, of the retained molecules to produce a second plurality of daughter ions, and measure
(Continued)

abundances of the second plurality of daughter ions as a function of the daughter ion mass.

20 Claims, 20 Drawing Sheets

(51) Int. Cl.
    *G01N 27/00*     (2006.01)
    *G01N 33/00*     (2006.01)
    *G01N 27/62*     (2006.01)
    *H01J 49/42*     (2006.01)
    *G01N 33/68*     (2006.01)

(52) U.S. Cl.
    CPC ...... *H01J 49/0031* (2013.01); *H01J 49/0036* (2013.01); *H01J 49/421* (2013.01)

(58) Field of Classification Search
    USPC .................................. 250/281, 282, 283, 288
    See application file for complete search history.

(56) References Cited

U.S. PATENT DOCUMENTS

| | | | |
|---|---|---|---|
| 2013/0203130 A1* | 8/2013 | Wittmann | C12P 13/08 435/115 |
| 2013/0331432 A1 | 12/2013 | Stephanopoulos et al. | |
| 2014/0273044 A1* | 9/2014 | Hellerstein | G01N 33/6848 435/15 |
| 2014/0329274 A1* | 11/2014 | Bowen | G01N 33/58 435/34 |
| 2015/0330969 A1* | 11/2015 | Kempa | G01N 33/6848 435/34 |

OTHER PUBLICATIONS

International Preliminary Report on Patentability dated Mar. 15, 2018 in connection with International Application No. PCT/US2016/049438.

* cited by examiner

| Metabolite | Q₁/Q₃ | | Daughter Ions | Mobile Phase Composition | (SV, CoV) |
|---|---|---|---|---|---|
| Taurine | 124/80 | | C1,2 | 15mM Ammonium Formate | (1400, -7.25) |
| PEP | M+0 | 167/79 | C1,2,3 | 15mM Ammonium Formate | (1800, -13.25) |
| | M+1 | 168/79 | | | |
| | M+2 | 169/79 | | | |
| | M+3 | 170/79 | | | |
| Pyruvate | M+0 | 87/87 | C1,2,3 | 15mM Ammonium Formate | (1200, -4.5) |
| | M+1 | 88/88 | | | |
| | M+2 | 89/89 | | | |
| | M+3 | 90/90 | | | |
| Malate | M+0 | 133/115 | C1,2,3,4 | 15uM Ammonium Formate | (1800, -12.25) |
| | M+1 | 134/116 | | | |
| | M+2 | 135/117 | | | |
| | M+3 | 136/118 | | | |
| | M+4 | 137/119 | | | |
| Aspartate | M+0 | 132/88 | C123  C234 | 15mM Ammonium Formate | (1800, -15.5) |
| | M+1 | 133/88 | | | |
| | | 133/89 | | | |
| | M+2 | 134/89 | | | |
| | | 134/90 | | | |
| | M+3 | 135/90 | | | |
| | | 135/91 | | | |
| | M+4 | 136/91 | | | |
| Glutamate | M+0 | 146/41 | C4,5 | 15uM Ammonium Formate | (1800, -12.5) |
| | M+1 | 147/41 | | | |
| | | 147/42 | | | |
| | M+2 | 148/41 | | | |
| | | 148/42 | | | |
| | | 148/43 | | | |
| | M+3 | 149/41 | | | |
| | | 149/42 | | | |
| | | 149/43 | | | |
| | M+4 | 150/42 | | | |
| | | 150/43 | | | |
| | M+5 | 151/43 | | | |
| Citrate | M+0 | 191/67 | C1,2,3,4  C2,3,4,5 | 15mM Ammonium Formate 0.1% Formic Acid 10uM EDTA | |
| | M+1 | 192/67 | | | |
| | | 192/68 | | | |
| | M+2 | 193/67 | | | |
| | | 193/68 | | | |
| | | 193/69 | | | |
| | M+3 | 194/68 | | | |
| | | 194/69 | | | |
| | | 194/70 | | | |
| | M+4 | 195/69 | | | |
| | | 195/70 | | | |
| | | 195/71 | | | |
| | M+5 | 196/70 | | | |
| | | 196/71 | | | |
| | M+6 | 197/71 | | | |
| Succinate | M+0 | 117/73 | C123  C234 | 15mM Ammonium Formate 0.1% Formic Acid 10uM EDTA | |
| | M+1 | 118/73 | | | |
| | | 118/74 | | | |
| | M+2 | 119/74 | | | |
| | | 119/75 | | | |
| | M+3 | 120/75 | | | |
| | | 120/76 | | | |
| | M+4 | 121/76 | | | |

FIG. 8

| | Acetyl-CoA Enrichments | |
|---|---|---|
| | $D_{4,5}$ | $S_{4,5}$ |
| | *From Citrate Isotopomeric Families* | |
| 1 | $cit_f$ | $cit_b$ |
| 2 | $cit_i$ | $cit_e$ |
| 3 | $cit_h$ | $cit_c$ |
| 4 | $cit_j$ | $cit_g$ |
| 5 | $\Sigma cit_{f,i,h,j}$ | $\Sigma cit_{b,e,c,g}$ |
| | *From Glutamate Isotopomers* | |
| 6 | 149/43 | 147/41 |
| 7 | 150/43 | 148/41 |
| 8 | 151/43 | 149/41 |
| 9 | 149/43+150/43+151/43 | 147/41+148/41+149/41 |

| | OAA Enrichments | | |
|---|---|---|---|
| | $D_{4,5}$ | | $S_{4,5}$ |
| | *From Citrate Isotopomeric Families* | | |
| 10 | $[(1)(2)(3)(4)-^{13}C_1]OAA$ | $cit_d$ | $\Sigma(cit_{a,f,h,i,j})$ |
| 11 | $[(1,2)(3,4)-^{13}C_2]OAA$ | $cit_f$ | $\Sigma(cit_{a,d,h,i,j})$ |
| 12 | $[(1,2,3)(2,3,4)-^{13}C_3]OAA$ | $cit_h$ | $\Sigma(cit_{a,d,f,i,j})$ |
| 13 | $[(1,2,3)(1,2,4)(1,3,4)(2,3,4)-^{13}C_3]OAA$ | $cit_i$ | $\Sigma(cit_{a,d,f,h,j})$ |
| 14 | $[U-^{13}C_4]OAA$ | $cit_j$ | $\Sigma(cit_{a,d,f,h,i})$ |

FIG. 12

| Flux | Substrate | Substrate Label | Product | Product Label |
|---|---|---|---|---|
| ΦPAc | Pyruvate (PEP) | $[U-^{13}C_3]$ | Acetyl-CoA | $[1,2-^{13}C_2]$ |
| Φβox | Lipid | NA | Acetyl-CoA | NA |
| ΦPAcCit | Pyruvate (PEP) | $[U-^{13}C_3]$ | Citrate | $\sum Cit_{a,d,f,h,i,j}$ |
| ΦPAcCitG | Pyruvate (PEP) | $[U-^{13}C_3]$ | Glutamate | $\sum Glut_{C4,5^{12}}$ |
| ΦAcCit | Acetyl-CoA | $[1,2-^{13}C_2]$ | Citrate | $\sum Cit_{a,d,f,h,i,j}$ |
| ΦAcCitG | Acetyl-CoA | $[1,2-^{13}C_2]$ | glutamate | $\sum Glut_{C4,5^{12}}$ |
| ΦPO* | Pyruvate (PEP) | $[U-^{13}C_3]PEP - OAA_{PC}$ | OAA | $OAA_{PC}$ (See Eqn. 2) |
| ΦPOD(1) | Pyruvate (PEP) | $[U-^{13}C_3]PEP - Asp_{PC}$ | Aspartate | $Asp_{PC}$ (See Eqn. 21) |
| ΦPOD(2) | Pyruvate (PEP) | $[U-^{13}C_3]PEP - Asp_{PC}$ | Aspartate | $Asp_{PC}$ (See Eqn. 24) |
| ΦPOM | Pyruvate (PEP) | $[U-^{13}C_3]PEP - Mal_{PC}$ | Malate | $Mal_{PC}$ (See Eqn. 19) |
| ΦPOCit | Pyruvate (PEP) | $[U-^{13}C_3]PEP - OAA_{PC}$ | Citrate | $\sum Cit_{c,h}$ |
| ΦCitG1* | Citrate | $\sum Cit_{a,d,f,h,i,j}$ | glutamate | $\sum Glut_{C4,5^{12}}$ |
| ΦCitG2 | Citrate | $Cit\left(\frac{h}{2}+\frac{i}{4}+j\right)$ | glutamate | $[U-^{13}C_3]Glutamate$ |
| ΦCitG3 | Citrate | $Cit\left(g+\frac{h+c}{2}+\frac{(i+e)}{4}+j\right)$ | glutamate | $\sum Glut_{C1,2,3^{13}}$ |
| ΦCitG4 | Citrate | $Cit\left(\frac{c}{2}+\frac{e}{4}+g\right)$ | glutamate | $[1,2,3-^{13}C_3]Glutamate$ |
| ΦCitG5 | Citrate | $Cit\left(\frac{b+f}{2}+\frac{h+c}{4}+\frac{3(i+e)}{4}\right)$ | glutamate | $\sum Glut_{C1,2,3^{13}}$ |
| ΦCitG6 | Citrate | $Cit\left(\frac{b+f}{2}+\frac{3d}{4}+\frac{3}{2}(192/68)\right)$ | glutamate | $\sum Glut_{C1,2,3^{13}}$ |
| ΦCitG7 | Citrate | $Cit(\sum(b,c,d,e,f,g,h,i,j,\frac{3}{2}(192/68)))$ | glutamate | $\sum Glut_{C1,2,3^{13}} + \sum Glut_{C1,2,3^{13}} + \sum Glut_{C1,2,3^{13}}$ |
| ΦCitS1 | Citrate | $Cit\left(a+c+\frac{d}{2}+\frac{e}{2}+g\right)$ | Succinate | $M^{+2}$ |
| ΦCitS2 | Citrate | $Cit\left(\frac{d}{2}+\frac{i}{2}+f\right)$ | Succinate | $M^{+3}$ |
| ΦCitS3 | Citrate | $Cit\left(\frac{i}{2}+h+j\right)$ | Succinate | $M^{+4}$ |
| ΦCitS4* | Citrate | $Cit\left(a+c+\frac{d}{2}+\frac{e}{2}+g+h+\frac{i}{2}+j\right)$ | Succinate | $M^{+2} + M^{+4}$ |
| ΦCitSM1 | Citrate | $Cit\left(a+c+\frac{d}{2}+\frac{e}{2}+g\right)$ | Malate | $M^{+2}$ |

FIG. 15A

| Flux | Substrate | Substrate Label | Product | Product Label |
|---|---|---|---|---|
| ΦCitSM1 | Citrate | $Cit\left(a+c+\dfrac{d}{2}+\dfrac{e}{2}+g\right)$ | Malate | $M^{+2}$ |
| ΦCitSM2 | Citrate | $Cit\left(\dfrac{i}{2}+h+j\right)$ | Malate | $M^{+4}$ |
| ΦCitSM3* | Citrate | $Cit\left(a+c+\dfrac{d}{2}+\dfrac{e}{2}+g+h+\dfrac{i}{2}+j\right)$ | Malate | $M^{+2}+M^{+4}$ |
| ΦGS | Glutamate | 149/43 + 150/43 + 151/43 | Succinate | $M^{+3}+M^{+4}$ |
| ΦSM1 | Succinate | $M^{+2}$ | Malate | $M^{+2}$ |
| ΦSM2 | Succinate | $M^{+4}$ | Malate | $M^{+4}$ |
| ΦSM3* | Succinate | $M^{+2}+M^{+4}$ | Malate | $M^{+2}+M^{+4}$ |
| ΦSMOD1 | Succinate | $M^{+2}$ | Aspartate | $M^{+2}$ |
| ΦSMOD2 | Succinate | $M^{+4}$ | Aspartate | $M^{+4}$ |
| ΦSMOD3* | Succinate | $M^{+2}+M^{+4}$ | Aspartate | $M^{+2}+M^{+4}$ |
| ΦMO1 | Malate | $M^{+2}$ | OAA | $M^{+2}$ |
| ΦMO2 | Malate | $M^{+3}$ | OAA | $M^{+3}$ |
| ΦMO3 | Malate | $M^{+4}$ | OAA | $M^{+4}$ |
| ΦMO4* | Malate | $M^{+2}+M^{+4}$ | OAA | $M^{+2}+M^{+4}$ |
| ΦMOCit1* | Malate | $M^{+2}$ | Citrate | $\sum Cit_{f,b}$ |
| ΦMOCit2 | Malate | $M^{+3}$ | Citrate | $\sum Cit_{c,e,h,i}$ |
| ΦMOCit3 | Malate | $M^{+4}$ | Citrate | $\sum Cit_{f,g}$ |
| ΦDO1 | Aspartate | $M^{+2}$ | OAA | $M^{+2}$ |
| ΦDO2 | Aspartate | $M^{+3}$ | OAA | $M^{+3}$ |
| ΦDO3 | Aspartate | $M^{+4}$ | OAA | $M^{+4}$ |
| ΦDO4* | Aspartate | $M^{+2}+M^{+4}$ | OAA | $M^{+2}+M^{+4}$ |
| ΦOC1* | OAA | $M^{+2}$ | Citrate | $\sum Cit_{f,b}$ |
| ΦOC2 | OAA | $M^{+3}$ | Citrate | $\sum Cit_{c,e,h,i}$ |
| ΦOC3 | OAA | $M^{+4}$ | Citrate | $\sum Cit_{f,g}$ |
| ΦDOC1* | Aspartate | $M^{+2}$ | Citrate | $\sum Cit_{f,b}$ |
| ΦDOC2 | Aspartate | $M^{+3}$ | Citrate | $\sum Cit_{c,e,h,i}$ |
| ΦDOC3 | Aspartate | $M^{+4}$ | Citrate | $\sum Cit_{f,g}$ |
| ΦOP | OAA | $\sum(\tfrac{1}{2}M^{+2}, \tfrac{1}{2}M^{+3})$ | Pyruvate | $M^{+2}$ |
| ΦMOP | Malate | $\sum(\tfrac{1}{2}M^{+2}, \tfrac{1}{2}M^{+3})$ | Pyruvate | $M^{+2}$ |
| ΦDOP | Aspartate | $\sum(\tfrac{1}{2}M^{+2}, \tfrac{1}{2}M^{+3})$ | Pyruvate | $M^{+2}$ |

FIG. 15B

TECHNIQUES OF MASS SPECTROMETRY FOR ISOTOPOMER ANALYSIS AND RELATED SYSTEMS AND METHODS

CROSS-REFERENCE TO RELATED APPLICATIONS

This application is the national phase filing under 35 U.S.C. § 371 of International Application No. PCT/US2016/049438, filed on Aug. 30, 2016, which claims priority to U.S. Provisional Patent Application No. 62/212,343, filed on Aug. 31, 2015, each of which are incorporated herein by reference to the maximum extent allowable.

FEDERALLY SPONSORED RESEARCH

This invention was made with government support under DK092606 awarded by National Institutes of Health. The government has certain rights in the invention.

BACKGROUND

Mass spectrometers are devices that may be used to identify amounts and types of a sample's chemical constituents by measuring the mass-to-charge ratio of the constituents when ionized. During a mass spectrometry analysis, a sample is ionized to produce molecular and/or elemental ions that are passed through a magnetic field. Ions with different mass-to-charge ratios will traverse different paths through the magnetic field, thereby allowing separation and measurement of each type of ion.

Mass isotopomers are molecules that have identical chemical and elemental compositions but contain different isotopes of their constituent elements and thereby have different masses. In some cases, there may be multiple mass isotopomers with the same mass that are different from one another because they have different positional arrangements of the same isotopes and/or different isotopic distributions. When a mass spectrometry analysis is performed that includes mass isotopomers, there may be present multiple different mass isotopomers having the same mass and/or unrelated chemical compounds that happen to have the same mass. Accordingly, some analyses of mass isotopomers via mass spectrometry may have trouble distinguishing one mass isotopomer from another and/or from other incidental compounds.

SUMMARY

The present application relates generally to techniques of mass spectrometry for isotopomer analysis.

According to some aspects, a spectrometer is provided, the spectrometer configured to receive molecules of a plurality of metabolites including one or more molecules of a first metabolite, filter the received molecules to retain molecules of the first metabolite including a plurality of different mass isotopomers of the first metabolite, fragment molecules of a first mass isotopomer of the retained molecules to produce a first plurality of daughter ions, measure abundances of the first plurality of daughter ions as a function of daughter ion mass, fragment molecules of a second mass isotopomer, different from the first mass isotopomer, of the retained molecules to produce a second plurality of daughter ions, and measure abundances of the second plurality of daughter ions as a function of daughter ion mass.

According to some embodiments, the spectrometer may be configured to perform said filtering based at least in part on a mobility of the received molecules.

According to some embodiments, the spectrometer may be configured to perform said filtering via ion-mobility spectrometry.

According to some embodiments, the spectrometer may be configured to perform said filtering via differential mobility spectrometry (DMS).

According to some embodiments, the spectrometer may be configured to perform said fragmenting steps and said measuring steps via tandem mass spectrometry.

According to some embodiments, the spectrometer may be configured to perform said fragmenting steps and said measuring steps via multiple reaction monitoring (MRM).

According to some embodiments, a system may be provided comprising the spectrometer and at least one processor configured to receive indications of the measured abundances of the first and second pluralities of daughter ions from the spectrometer, and determine a metabolic flux for the first metabolite based at least in part on the received indications.

According to some embodiments, the at least one processor may be further configured to perform a correction to the received indications of the measured abundances based on a process in which isocitrate dehydrogenase (ICDH) reacts with isocitrate.

According to some embodiments, the at least one processor may be further configured to perform a correction to the received indications of the measured abundances based on a natural abundance of carbon-13.

According to some embodiments, the determined metabolic flux may comprise a plurality of conversion rates to the first metabolite from metabolites of the plurality of metabolites other than the first metabolite.

According to some embodiments, determining the metabolic flux for the first metabolite may comprise determining an abundance of a group of positional isotopomers of the first mass isotopomer.

According to some aspects, a method is provided comprising receiving molecules of a plurality of metabolites including one or more molecules of a first metabolite, filtering the received molecules to retain molecules of the first metabolite including a plurality of different mass isotopomers of the first metabolite, fragmenting molecules of a first mass isotopomer of the retained molecules to produce a first plurality of daughter ions, measuring abundances of the first plurality of daughter ions as a function of daughter ion mass, fragmenting molecules of a second mass isotopomer, different from the first mass isotopomer, of the retained molecules to produce a second plurality of daughter ions, measuring abundances of the second plurality of daughter ions as a function of daughter ion mass.

According to some embodiments, the received molecules may include citrate, pyruvate, aspartate, malate, succinate and glutamate.

According to some embodiments, the molecules of the first metabolite may include a plurality of isotopologues of the first metabolite.

According to some embodiments, the molecules of the first metabolite may include a plurality of carbon-13 enriched molecules.

According to some embodiments, the method may further comprise introducing a source of carbon-13 to the molecules of the plurality of metabolites.

According to some embodiments, the method may further comprise determining metabolic fluxes for the first metabolite at a plurality of time points subsequent to the introduction of the source of carbon-13.

According to some embodiments, the method may further comprise determining a metabolic flux for the first metabolite based at least in part on the measured abundances.

According to some embodiments, the method may further comprise introducing a plurality of effector molecules to the molecules of the plurality of metabolites.

According to some embodiments, the method may further comprise determining metabolic fluxes for the first metabolite at a plurality of time points subsequent to the introduction of the plurality of effector molecules.

BRIEF DESCRIPTION OF DRAWINGS

Various aspects and embodiments will be described with reference to the following figures. It should be appreciated that the figures are not necessarily drawn to scale. In the drawings, each identical or nearly identical component that is illustrated in various figures is represented by a like numeral. For purposes of clarity, not every component may be labeled in every drawing.

FIG. 8 lists MRM transition pairs (Q1/Q3), carbons analyzed in each fragment, mobile phase and approximate SV-CoV pair for each metabolite studied in an illustrative analysis, according to some embodiments;

FIG. 12 depicts Acetyl-CoA and OAA fractional enrichments based on citrate and glutamate isotopic data for an illustrative analysis, according to some embodiments;

FIGS. 15A-15B lists steady-state precursor-product relationships between the metabolic intermediates involved in the PC, PDH and TCA cycle reactions in an illustrative analysis, according to some embodiments;

DETAILED DESCRIPTION

Figure 1:
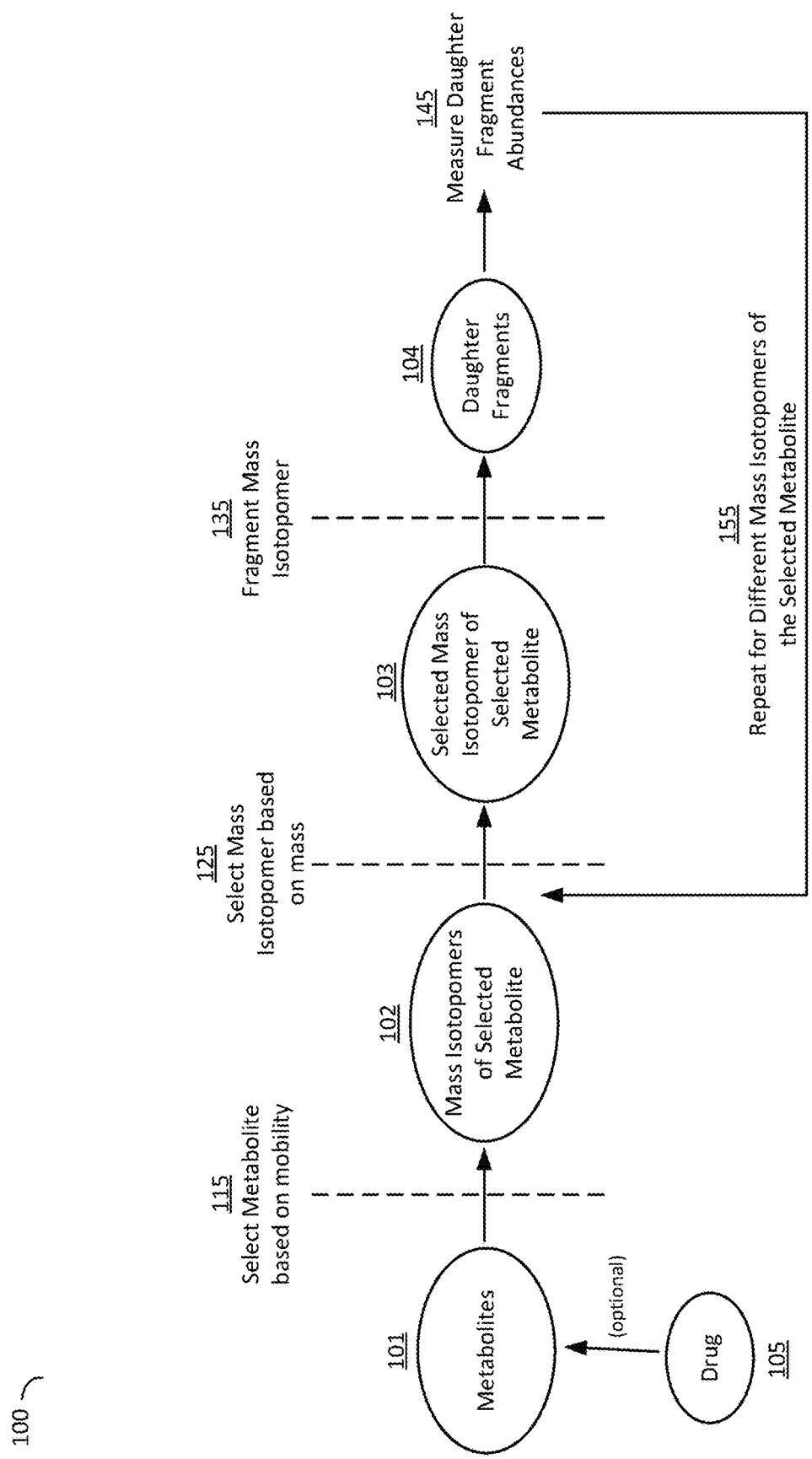
FIG. 1 is a flowchart of an illustrative process for performing an isotopomer analysis of metabolites, according to some embodiments.

As discussed above, mass spectrometry generally involves ionizing a sample to produce ions that are passed through a magnetic field, thereby allowing separation and measurement of the mass-to-charge ratio of each ion. In some cases, a mass spectrometer may perform multiple steps with ionized particles. For instance, an ionization step may produce ionized molecules that may be separated by type in a magnetic field, then a second step may fragment the separated ions. The ionized fragments may then be passed through another magnetic field and their abundances measured.

Mass spectrometry is often employed to understand the assembly and disassembly of complex molecules, such as polymers, that takes place during chemical processes. In particular, biological processes generally include numerous pathways by which biological molecules may be converted into other biological molecules, thereby producing a complex mix of interconverting molecules.

For instance, the citric acid cycle (sometimes referred to as the tricarboxylic acid (TCA) cycle, or the Kreb's cycle) is a series of chemical reactions that takes place within cells of all aerobic organisms, including everything from bacteria to humans. The TCA cycle generates chemical energy (in the form of adenosine triphosphate, or ATP) from carbohydrates, fats and proteins and is thereby the source of metabolism within cells. The TCA cycle is extremely complex, as a large number of chemical reactions form steps of the cycle, including steps that produce intermediates of the cycle's cyclical nature, in addition to steps that generate or consume byproducts such as water, carbon dioxide, or ATP. As a result of the large number of different chemicals present within the cell at any given time, it is not conventionally feasible to provide these chemicals to a mass spectrometer since the measured abundances of ions could not be traced back to their parent molecules. That is, the metabolites may not be distinguishable from one another once fragmented and their constituent ionic fragments measured, due to fragments with the same mass to charge ratios being potentially generated from different metabolites.

In other words, because a mass spectrometer attempts to identify a metabolite based on a measured mass to charge ratio, and because there are many metabolites with identical mass to charge ratios in the range of the spectrum where central carbon metabolism is observed, there is ambiguity in determination of one metabolite from another based solely on a mass to charge ratio analysis.

One approach that may distinguish molecular fragments from one another is to introduce a stable isotope mass label to the chemical reactions. The stable isotope used is typically carbon-13, which may replace naturally-occurring carbon-12 atoms present in the biological molecules and thereby alter the mass of the molecules without otherwise affecting their chemical or biological properties. A location within a molecule in which the usual atom has been replaced with a different isotope of the same atom is sometimes referred to as having been "labeled" by the replacement. Since the number of labeled atoms in a molecule affects the mass of the molecule, whether a molecule is labeled and if so, to what extent, can be measured through mass spectrometry. Moreover, since labeled atoms can propagate from one type of molecule to another as chemical reactions occur, it may be possible to track the labeled atoms through a biological process to provide information on how much of each metabolite is present over time.

However, the labeling approach may further increase the above-described ambiguity between metabolites when they are measured with a mass spectrometer, since the plurality of ways that a given molecule may be labeled produces an increased number of species with the same mass to charge ratio. For example, a molecule comprising multiple hydrogen atoms may be labeled in a number of ways by replacing a hydrogen atom with deuterium. For a given number of labeled hydrogen atoms, there are multiple ways in which the molecule can be labeled by selecting which of the hydrogen atoms is/are labeled, yet each way results in a molecule with the same mass. Abundances of each of these different mass isotopomers may therefore be ambiguous based on measurement of mass abundances alone. Furthermore, such an ambiguity may be present not only for a parent ion, but for any resultant daughter fragments produced from the parent, since different mass isotopomers may, once fragmented, produced fragments having the same or different masses as fragments produced from other mass isotopomers.

The inventors have recognized and appreciated that by considering the different possible labeling sites and fragmenting processes occurring during analysis of the many molecules participating in the TCA cycle via a mass spectrometer, sufficient information may be extracted to identify the abundances of each of the molecules.

The inventors have further recognized and appreciated that conventional mass spectrometry techniques are insufficient to perform measurements of metabolite interconversion reactions within the time scales necessary to understand the biological processes underlying the reactions. Due to the number of different metabolites that need to be measured to develop a full picture of metabolite reaction rates, and the time needed to measure each of these metabolites, there is simply not enough of a duty cycle within a conventional mass spectrometer to perform these measurements successfully. Metabolites quickly interconvert amongst one another in the TCA cycle, yet it is not possible to ascertain the metabolic reaction rates without measuring substantially all of the metabolites. A conventional mass spectrometer is unable to determine these rates, because by the time a measurement has been performed in a conventional approach sufficient changes have occurred in the metabolites to mitigate extraction of the necessary information to understand the ongoing processes.

The inventors have therefore further recognized and appreciated that an improved mass spectrometer which enables efficient analysis of multiple metabolites may allow for a complete set of metabolic reaction rates to be determined. In particular, the mass spectrometer may be configured to simultaneously receive all isotopomers of a single metabolite and to analyze all the isotopomers to determine an amount of each type of isotopomer. Such an approach may reduce cycling time, unify peak shape, and/or reduce the compounding of propagated errors that would otherwise significantly limit the analytic power of the mass spectrometer measurements when performed on groups of isotopomers in turn for a given metabolite.

As discussed above, isotopomers are molecules that have identical elemental compositions but are formed from different positional arrangements of isotopic variants of these elements. In some implementations, the improved mass spectrometer described herein may determine positions of stable isotope mass labels of the isotopomers. The inventors have developed novel isotopomer analysis techniques for interpreting data from the improved mass spectrometer such that the data obtained for a single metabolite can be interpreted appropriately and thereby used to determine metabolic reaction rates.

According to some embodiments, the improved mass spectrometer described herein may be used while measuring the time since the introduction of labeled atoms (e.g., carbon-13 atoms) to metabolic processes, thereby allowing reaction rates of stages of the metabolic cycle to be determined. A drug and/or condition may also be introduced to the metabolic processes, and metabolic reaction rates may be continuously measured using the mass spectrometer before and after introduction of the drug and/or condition, thereby leading to an understanding of how the drug affects the metabolic reactions within the cell. In some implementations, the isotopomer analysis techniques described herein may be used to determine how much of each metabolite is present at various times, and to determine positions of labels within those metabolites. The analysis may accordingly provide a comparison of metabolic function in the presence of a drug and/or condition with that of metabolic function in the drug and/or condition's absence.

Following below are more detailed descriptions of various concepts related to, and embodiments of, systems and methods of mass spectrometry for isotopomer analysis. It should be appreciated that various aspects described herein may be implemented in any of numerous ways. Examples of specific implementations are provided herein for illustrative purposes only. In addition, the various aspects described in the embodiments below may be used alone or in any combination, and are not limited to the combinations explicitly described herein.

FIG. 1 is a flowchart of an illustrative process for performing an isotopomer analysis of metabolites, according to some embodiments. In method 100, a plurality of metabolites (that is, a plurality of molecules that include at least two different metabolite molecules) are provided as input to a mass spectrometer. The mass spectrometer is configured to perform a series of operations to select a metabolite and fragment the metabolite into ions so that the composition of the metabolites present may be determined.

As described above, the inventors have developed an improved mass spectrometer which enables efficient analysis of multiple metabolites. The process shown in method 100 may employ such a mass spectrometer in order to perform the steps shown in the method and discussed further below. In particular, in some embodiments, a mass spectrometer performing method 100 may be configured to select all of the mass isotopomers of a single metabolite and to measure abundances of fragments of these isotopomers.

In the example of method 100, metabolites 101 are provided as input to a spectrometer. The spectrometer performing method 100 may include any suitable type of spectrometry device(s), including a spectrometer configured to perform ion-mobility spectrometry and/or tandem mass spectrometry. For instance, a spectrometer to which input is provided in method 100 may perform at least differential mobility spectrometry (DMS) and/or multiple reaction monitoring (MRM) operations.

Metabolites 101 may include any one or more metabolic molecule types, including but not limited to, aspartate, pyruvate, succinate, malate, oxalacetic acid (OAA), citrate, acetyl coenzyme A (AcCoA), glutamate, a-ketoglutarate, or combinations thereof. The metabolites 101 may include any number of molecules of any number of metabolic molecules (e.g., any number of aspartate molecules, any number of pyruvate molecules, etc.). According to some embodiments, the metabolites may have been prepared for delivery to the mass spectrometer for ionization with or without prior derivatization or adduct formulation.

In some embodiments, one or more molecules of the metabolites 101 are labeled. That is, as discussed above, in place of one or more of the naturally occurring isotopes within the molecule(s) alternative isotopes may be provided, thereby "labeling" those isotopes. In some embodiments, one or more molecules of the metabolites 101 are labeled using carbon-13 (e.g., by reacting the molecules comprising atoms of carbon-12 such that an additional neutron is added to one or more of those carbon atoms). A number of metabolites of a single molecule may be labeled (e.g., a number of citrate molecules may be the only labeled molecules), or a number of metabolites of a number of molecules may be labeled. As metabolites 101 interconvert, the number and type of molecules having labels may change over time. In some embodiments, drug 105 may be combined with metabolites 101 and provided as input to the mass spectrometer. Inclusion of the drug 105 with the metabolites may affect the rates at which the various metabolites interconvert as described further below.

According to some embodiments, the metabolites may be labeled either in vivo or in vitro with a positional mass substrate in place of the unlabeled endogenous substrate (e.g. labeling or infusion of variably enriched $[U-^{13}C_6]$-D-glucose in place of an equimolar amount of unlabeled D-glucose) for defined time points before being quenched/harvested for mass spectroscopic analysis.

In step 115 of method 100, one of the metabolite types (e.g., pyruvate, citrate, etc.) of metabolites 101 is selected based on a mobility of the metabolite type. For instance, all citrate molecules may be selected in step 115 based on their mobility (and not on the molecules' mass to charge ratios). Since mobility of the metabolites is unaffected by labeling of atoms of the metabolite molecules (both whether there is any labeling, and how many of the atoms are labeled), multiple (e.g., all) labeling configurations of the selected metabolite type may be captured in step 115. This step thereby can produce a plurality of mass isotopomers of the selected metabolite, which may include different isotopomers of the selected metabolite (e.g., citrate without labels and/or citrate with one labeled atom and/or citrate with two labeled atoms, etc.) if there is labeling exhibited by the selected metabolite, or may include only a single isotopomer (e.g., citrate without labels) if there is no labeling exhibited by the selected metabolite. In some embodiments, step 115 may be performed using ion-mobility spectrometry (IMS), such as, but not limited to, differential mobility spectrometry (DMS) or differential mobility analysis (DMA).

In step 125, molecules of one of the isotopomers 102 (that is, molecules sharing the same isotopic structure) are selected based on the isotopomer's mass. This may be performed, for instance, by ionizing the molecules 102 and selecting for a particular mass-to-charge ratio that selects for the desired mass isotopomer using a mass spectrometer. However, any suitable mass analyzer may be used to select for a desired mass isotopomer.

In step 135, the selected mass isotopomer is fragmented to produce daughter fragments 104. In some embodiments, the daughter fragments may be ionized during step 135 and/or may be fragments of ions produced during fragmentation performed in step 125.

In step 145, abundances of the daughter fragments 104 are measured. The abundances may include a determination of absolute and/or relative amounts of one or more daughter fragments by mass. For instance, abundances of a plurality of daughter fragment types having different masses may be measured.

In step 155, method 100 returns to step 125 to select a different mass isotopomer from isotopomers 102. Steps 125, 135 and 145 may then be repeated a desired number of times until daughter fragments for a desired selection of isotopomers from isotopomers 102 (which may include some or all of the isotopomers) have been measured.

According to some embodiments, steps 125, 135 and 145 may be repeated one or more times without adjusting step 115, which selects metabolites having the same mobility for input to step 125. In such embodiments, steps 125, 135 and 145 may be repeated a desired number of times in an efficient manner thereby measuring abundances of all desired daughter fragments for a given metabolite in a time window such as, but not limited to, less than 30 ms, less than 10 ms, less than 5 ms, or less than 2 ms. For instance, steps 125, 135 and 145 may be operated for a plurality of isotopomers for a time window of between 1 ms and 5 ms, and abundances of a plurality of daughter fragment abundances for a plurality of mass isotopomers of a metabolite determined based on data obtained during this time window.

Thereby, as discussed above, by continually operating step 115 in a fixed mode to pass in all molecules of a given metabolite, a spectrometer performing method 100 may determine abundances of daughter fragments of the metabolite in a short time. Step 115 may then be repeated for a different metabolite, and steps 125, 135 and 145 performed one or more times for the different metabolite. In this manner, each metabolite type of metabolites 101 may be analyzed and daughter fragment abundances determined in a sufficiently small time so as to allow determination of metabolite interconversion rates within metabolites 101, as discussed further below.

Figure 2:
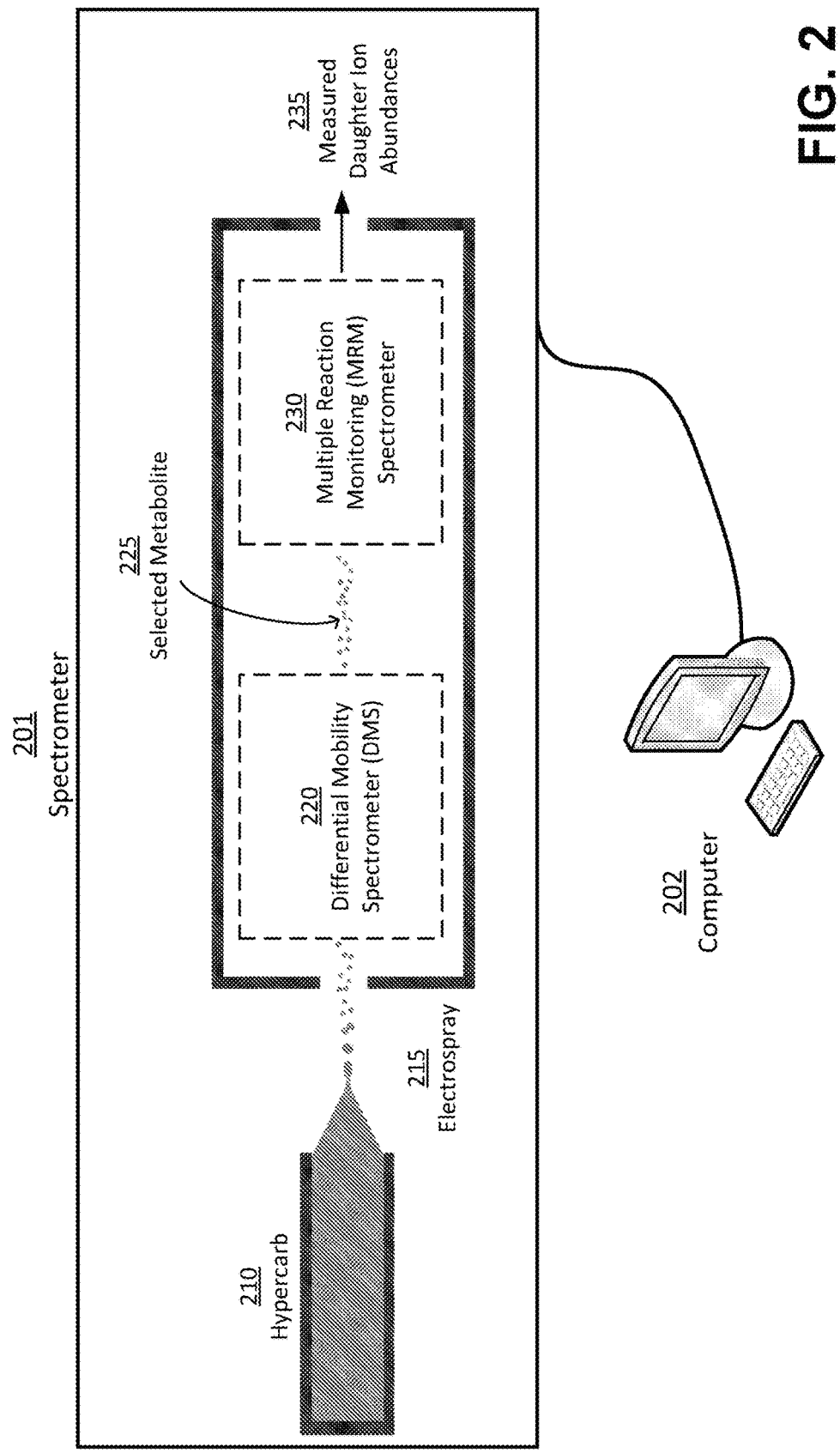
FIG. 2 depicts an illustrative spectrometer that may be used to perform an isotopomer analysis of metabolites, according to some embodiments.

FIG. 2 depicts an illustrative spectrometer that may be used to perform an isotopomer analysis of metabolites, according to some embodiments. System 200 includes spectrometer 201 and computer 202. Spectrometer 201 is an illustrative device that may, for instance, perform method 100 shown in FIG. 1, and computer 202 is an illustrative device that may perform calculations to determine metabolite interconversion rates based on data received from spectrometer 201. In some embodiments, computer 202 may operate one or more functions of spectrometer 201.

In the example of FIG. 2, spectrometer 201 includes hypercarb column 210 into which one or more metabolites are provided. The metabolites are ionized from droplets via electro spray 215 and provided to differential mobility spectrometer (DMS) 220. The DMS 220 selects a metabolite (e.g., citrate) based on the molecules' mobility, and may therefore select both labeled and unlabeled molecules of the metabolite. Molecules of the selected metabolite 225 are provided to multiple reaction monitoring (MRM) spectrometer 230, which selects a parent ion, fragments the parent ion into daughter ions, and measures abundances of one or more of the daughter ions, thereby producing abundance values 235.

Abundance values 235 may be provided to computer 202, which may record the abundance values for the selected metabolite and the selected parent ion as a function of daughter ion mass. Abundance values 235 may be determined for a number of different metabolite and/or parent ion combinations, and used to determine metabolite interconversion rates of the metabolites in hypercarb column 210. For instance, if the processes that interconvert metabolites into other metabolites are known, and the ways in which differently labeled isotopomers of a given metabolite can fragment into labeled or unlabeled fragments are known, abundances of these fragments can indicate rates at which metabolites are interconverting into other metabolites.

According to some embodiments, DMS 220 may be configured to output molecules having a particular mobility, thereby outputting selected metabolite 225 to MRM spectrometer 230, while MRM spectrometer 230 determines abundances of daughter ions for multiple parent ions. Conventional spectrometers may operate DMS 220 and MRM spectrometer 230 as a single unit such that DMS 220 must be "reset" after each set of daughter ion abundances is determined. As discussed above, such operation may reduce the duty cycle of the spectrometer such that a determination of metabolic interconversion rates is not possible. By continually operating DMS 220 to output a selected metabolite based on its mobility, whilst MRM spectrometer 230 performs measurements for multiple isotopomers of the selected metabolite, the duty cycle of the spectrometer 201 may be sufficiently low as to measure abundances for multiple isotopomers of multiple metabolites in a time window short enough to enable determination of metabolic interconversion rates of the metabolites.

According to some embodiments, ions produced from the electrospray 215 may be introduced into the vacuum of MRM spectrometer 230 after passing through DMS 220 in the presence of a retrograde flow of non-polar volatile and/or atomic modifier gas in order to filter out interfering ions that are isobaric with any of the isotopomers of interest.

Figure 3:
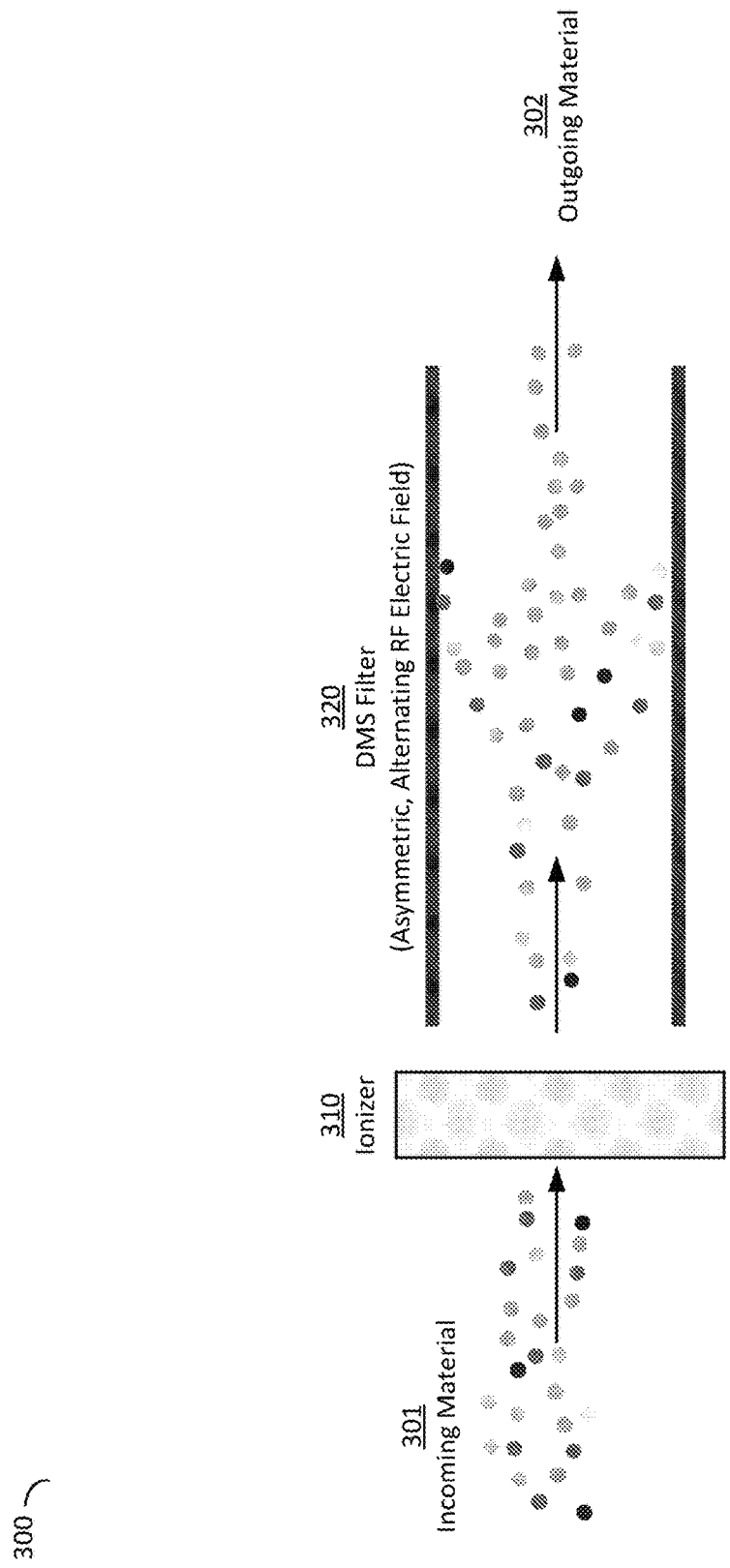
FIG. 3 depicts operation of a differential mobility spectrometry (DMS) device that may form part of a spectrometer, according to some embodiments.

To illustrate one possible way to select molecules based on mobility, FIG. 3 depicts operation of a differential mobility spectrometry (DMS) device, according to some embodiments. DMS device 300 may, for example, be used as DMS 220 in system 200 and/or to perform step 115 of method 100 shown in FIG. 1. In the example of FIG. 3, device 300 receives material 301, which may include molecules of a plurality of different types of metabolites. The material 301 is passed through ionizer 310, producing ions from at least some of the metabolite molecules, and the resultant ions are passed into DMS filter 320.

DMS filter 320 may be configured to apply an asymmetric, alternating electric field to the material while the ions pass through a transport gas, such as isopropanol and/or nitrogen gas. The alternating electric field causes the ions to move with an up/down or "zig-zag" motion through the filter. Ions with the same mobility in the gas will have substantially the same trajectory through the gas, which is dependent upon the electric field. Accordingly, the electric field strength may be used to select for ions with a particular mobility. Ions not having the selected mobility are either output from the filter or impact the walls of the filter. Outgoing material 302 having the selected mobility are thereby output from the device.

Figure 4:
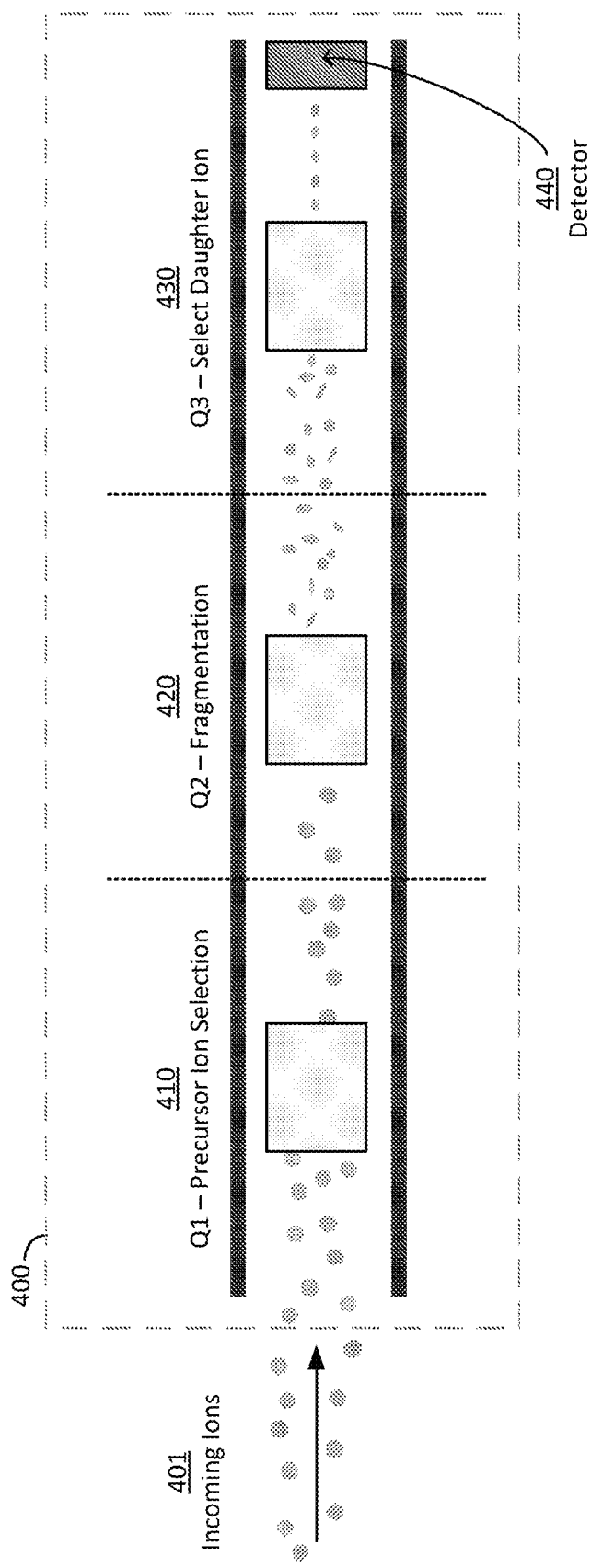
FIG. 4 depicts operation of a multiple reaction monitoring (MRM) device that may form part of a spectrometer, according to some embodiments.

FIG. 4 depicts operation of a multiple reaction monitoring (MRM) device that may form part of a spectrometer, according to some embodiments. MRM spectrometer 400 may, for example, be used as MRM spectrometer 230 in system 200 and/or to perform steps 125, 135 and/or 145 of method 100 shown in FIG. 1.

Incoming ions 401 (e.g., output from a DMS filter, such as DMS filter 320 shown in FIG. 3, or otherwise) are provided as input to MRM spectrometer 400. In stage 410, a precursor (parent) ion may be selected from the incoming ions by adjusting a magnetic field within stage 410 to select for the parent ion's charge-to-mass ratio. Thereby, substantially only those parent ions with the selected charge-to-mass ratio may be output from stage 410.

The selected parent ion is fragmented in stage 420 to produce a plurality of daughter ions, and in stage 430 a daughter ion having a particular mass is selected and output to a detector 440. The daughter ion selected in stage 430 may be selected by adjusting a magnetic field within stage 430 to select for the daughter ion's charge-to-mass ratio. The magnetic fields in stages 410 and 420 may be adjusted to facilitate measurement of multiple daughter ions of multiple parent ions within a short time frame, such as in less than 10 ms, or less than 2 ms, or between 1 ms and 5 ms.

Figure 5:
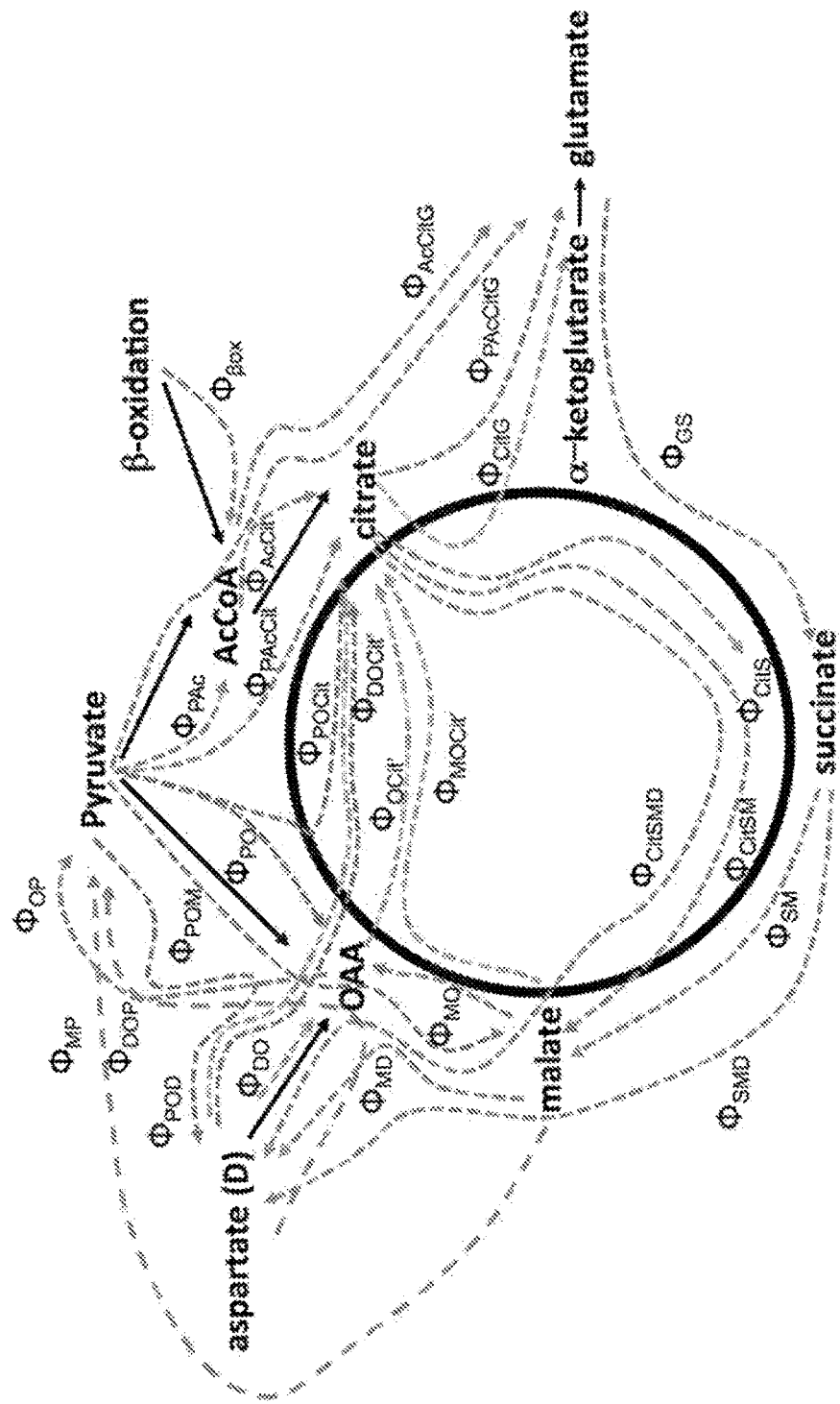
FIG. 5 is a graphical scheme of steady-state precursor-product relationships between metabolic intermediates contributing to a TCA cycle, according to some embodiments.

FIG. 5 is a graphical scheme of steady-state precursor-product relationships between metabolic intermediates contributing to a TCA cycle, according to some embodiments. Each of the parameters 1 shown in FIG. 5 represents a relative flux across a particular metabolic pathway of the TCA cycle. By measuring abundances of daughter fragments of the different metabolites of the TCA cycle using the techniques described above, and by utilizing stoichiometric relationships between isotopomers of the metabolites, the positions of labeled atoms within those metabolites may be tracked over time and the flux values determined.

According to some embodiments, a steady state analysis of the flux values 1 is performed to identify step-wise as well as trans-pathway dilutions to quantitatively identify the relative flows of metabolites across metabolic intersections. In some implementations, measurements of positional enrichments may be measured at a plurality of time points, thereby allowing measurement of enrichment build up rates across each of the isotopomer families of interest. These rates can be plotted and analyzed to generate metabolic rates of the individual reactions. An illustrative study utilizing this approach is described below using the insulinoma INS-1 cell line labeled for different durations of time using uniformly labeled glucose.

According to some embodiments, when determining one or more flux values, one or more of a number of corrections to the measured data may be applied. In some embodiments, a determination of the flux values includes a correction to account for the roughly 1.1% of natural carbon that is carbon-13, and that can therefore interfere with the labeling process by confusing which labels were due to the introduction of labeled carbon and which were naturally occurring.

In some embodiments, a determination of one or more flux values includes a correction for a process in which isocitrate dehydrogenase (ICDH) can remove a labeled carbon atom from isocitrate and replace it with an unlabeled carbon. Without this correction, it may not be possible to correctly interpret positional labeled of citrate, and understanding citrate is critical in understanding the metabolic interconversion rates of the TCA cycle.

In some embodiments, a determination of one or more flux values includes a mass isotope distribution analysis (MID A) to determine positional-enrichments of mitochondrial acetyl CoA and oxaloacetic acid.

Figure 6:
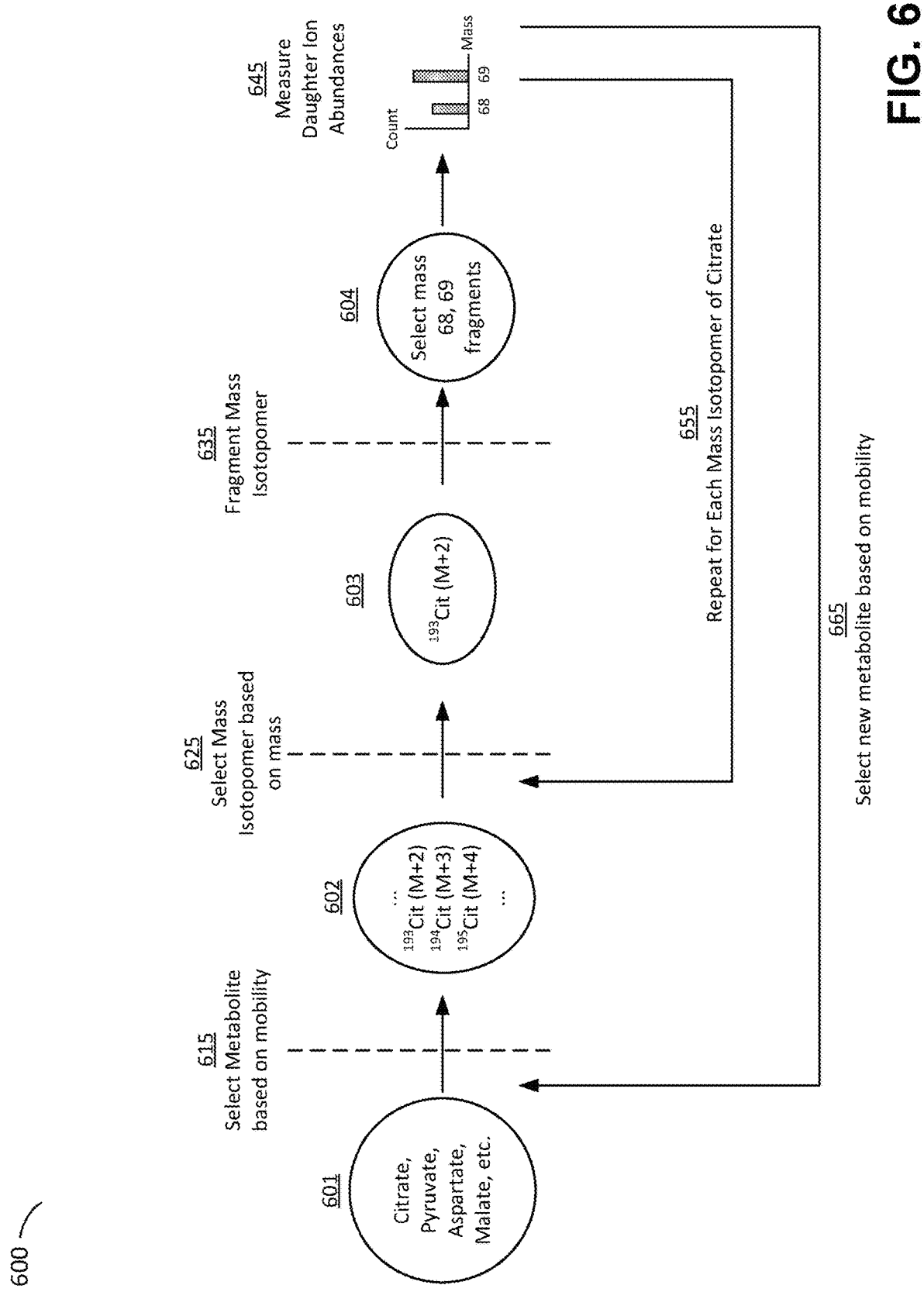
FIG. 6 is a flowchart of an illustrative process for performing an isotopomer analysis of citrate, according to some embodiments.

FIG. 6 is a flowchart of an illustrative process for performing an isotopomer analysis that includes an analysis of citrate, according to some embodiments. Method 600 is an illustrative embodiment of method 100 in which a plurality of metabolites 601 are provided and include citrate, and in which citrate is selected for based on its mobility.

In the example of FIG. 6, metabolites 601 include citrate, pyruvate, aspartate, malate and other metabolic molecules present in the TCA cycle (that is, being an element produced and/or consumed by the cycle, being fed into the cycle, and/or being exchanged with the cycle). In the example of FIG. 6, a source of labeled carbon-13 atoms has previously been introduced to metabolites 601 and the metabolites thereby may include one or more isotopomers of each of the types of metabolites.

In step 615, the citrate molecules in metabolites 601 are selected based on their mobility (which is substantially identical irrespective of which isotopomers of citrate are present in metabolites 601). Thereby, molecules of citrate isotopomers 602 are produced, which includes citrate molecules with two labeled carbon atoms and a molecular mass of 193, citrate molecules with three labeled carbon atoms and a molecular mass of 194, etc. In FIG. 6, the notation (M+X) is used to denote an isotopomer with a naturally-occurring mass M that has X additional neutrons present. This includes all isotopomers with the denoted mass, and therefore may include positional and/or isotopic variants having the same mass.

In step 615, molecules of the mass-193 citrate isotopomer are selected, and step 635 these molecules are fragmented to produce daughter fragments 604, which include fragments with a molecular mass of 68 and fragments with a molecular mass of 69. The abundance of each type of fragment is measured in step 645.

The relative abundances of the two daughter fragments measured in step 645 provides information about the positions of the labeled carbon atoms in the citrate isotopomer selected in step 625, due to the possible ways in which the citrate molecule may fragment. In step 655, the method returns to step 625 to select a different mass isotopomer of citrate, which provides further information about how the citrate atoms have been labeled. Further, steps 615, 625, 635 and 645 may be repeated for multiple metabolites, thereby allowing an analysis to track the propagation of labeled atoms through the TCA cycle over time.

Figure 7:
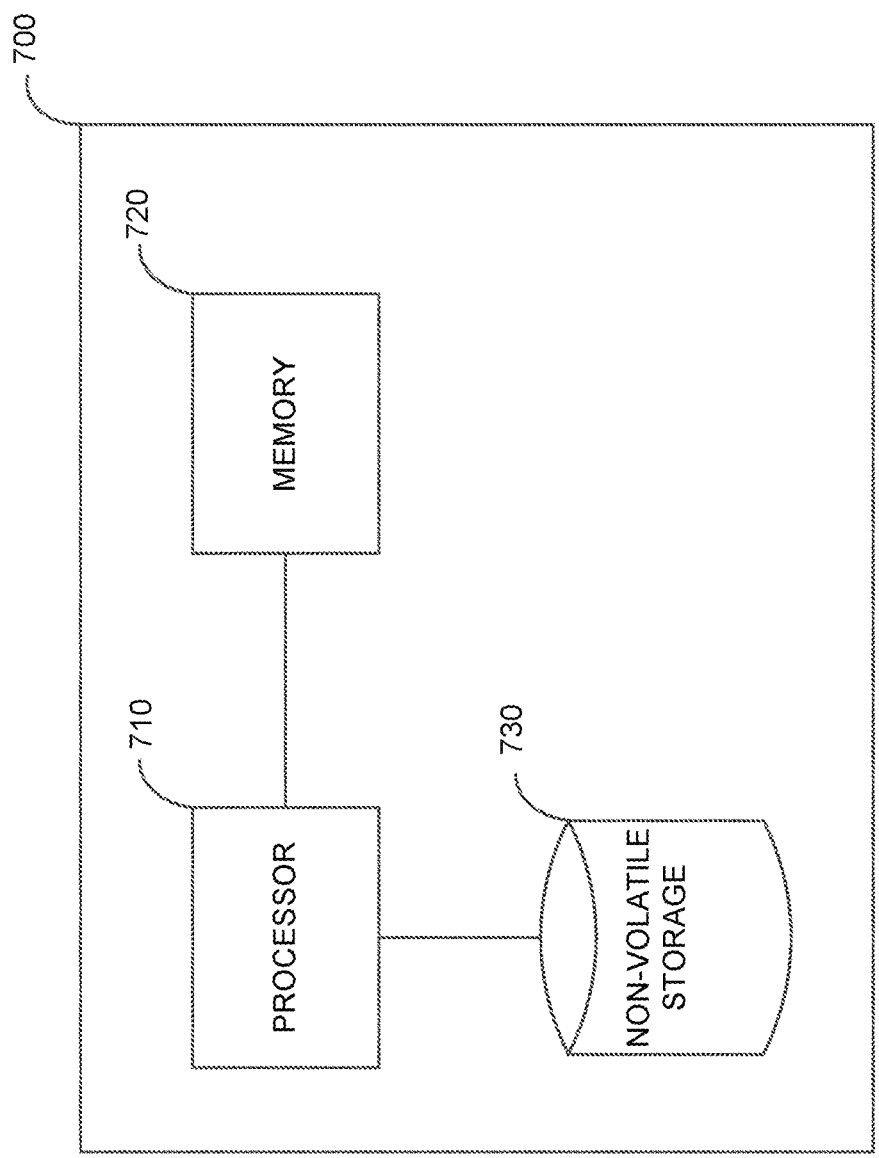
FIG. 7 illustrates an example of a computing system environment on which aspects of the invention may be implemented.

An illustrative implementation of a computer system 700 that may be used to perform isotopomer analysis in conjunction with a mass spectrometer as described herein is shown in FIG. 7. The computer system 700 may include one or more processors 710 and one or more non-transitory computer-readable storage media or storage devices (e.g., memory 720 and one or more non-volatile storage media 730). The processor 710 may control writing data to and reading data from the memory 720 and the non-volatile storage device 730 in any suitable manner, as the aspects of the invention described herein are not limited in this respect. To perform the functionality and/or techniques described herein, the processor 710 may execute one or more instructions stored in one or more computer-readable storage media (e.g., the memory 720, storage media, etc.), which may serve as non-transitory computer-readable storage media storing instructions for execution by the processor 710.

In connection with techniques for isotopomer analysis in conjunction with a mass spectrometer as described herein, code used to, for example, operate a mass spectrometer, calculate metabolic conversion rates, record measured ion abundances, etc. may be stored on one or more computer-readable storage media of computer system 700. Processor 710 may execute any such code to provide any techniques for performing isotopomer analysis in conjunction with a mass spectrometer as described herein. Any other software, programs or instructions described herein may also be stored and executed by computer system 700. It will be appreciated that computer code may be applied to any aspects of methods and techniques described herein. For example, computer code may be applied to measurement of ion abundances and/or calculation of metabolic interconversion rates.

Various inventive concepts may be embodied as at least one non-transitory computer readable storage medium (e.g., a computer memory, one or more floppy discs, compact discs, optical discs, magnetic tapes, flash memories, circuit configurations in Field Programmable Gate Arrays or other semiconductor devices, etc.) or a computer readable storage device encoded with one or more programs that, when executed on one or more computers or other processors, implement some of the various embodiments of the present invention. The non-transitory computer-readable medium or media may be transportable, such that the program or programs stored thereon may be loaded onto any computer resource to implement various aspects of the present invention as discussed above.

The terms "program," "software," and/or "application" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of one or more embodiments described herein need not reside on a single computer or processor, but may be distributed in a modular fashion among different computers or processors to implement various aspects of the present invention.

While particular techniques for mass spectrometry for isotopomer analysis have been discussed herein, it will be appreciated that the techniques described herein are not limited to any particular technique(s) for performing mass spectrometry in combination with a computer system. For instance, examples described herein include providing data from a spectrometer to a computer (e.g., as shown in FIG. 2). However, the techniques described herein are not limited to embodiments in which a computer is a separate device from the spectrometer, as any technique or techniques for performing calculations to determine metabolic reaction rates may be utilized. This non-limiting description thereby applies to, for example, a spectrometer with an "on-board" or otherwise built-in computing device in addition to a spectrometer coupled to one or more computing devices that perform calculations to determine (and/or aid in the determination of) reaction rates, including metabolic reaction rates.

The mass spectrometry techniques can be utilized in determination of metabolic flux as described herein, in addition to any other suitable use case in which mixtures of molecules are changing over time. For instance, the techniques could be used to analyze an enzymatic and/or chemical reaction, or series of such reactions, in which isotopomers are generated. Such reactions might relate to intact organisms, living cells, extracts/lysates, engineered/synthesized mixtures of enzymes, biochemical or industrial reactions, or combinations thereof, wherein distinguishing between a natural and/or unnatural products containing mass isotopomers is desirable. One or more proteins, peptides, nucleic acids, carbohydrates, and/or polymers that can acquire one or more mass labels in vivo and/or in vitro could be analyzed as whole or constituent parts.

For example, for a reaction in which a protein is digested into amino acids that are variably or positionally enriched with a mass label, the techniques described herein could be used to distinguish between one or more of those amino acids. In some use cases, detection of a compound within a complex mixture where a mass label is applied as a reactant and/or standard by which to normalize could be performed via enzymatic or chemical derivatization. For example, detection of a metabolite/reagent that has isobars not otherwise easily separated could undergo an enzymatic reaction (allotopic or orthotopic) or chemical reaction/derivatization (with or without a mass label) in the presence or absence of a standard (with or without mass label) that can then be distinguished/separated by such a modification and subjected to enrichment analysis.

According to some embodiments, the mass spectrometry techniques described herein may be particularly useful when applied in early stage drug discovery applications, for target identification and/or validation, assay development, hypothesis testing, multi-ordinate high-content screening, lead generation and/or optimization, mechanism of action, and/or de-orphaning studies. For instance, a mass spectrometry analysis of a mixture of metabolites and a drug to be analyzed may identify the drug's effects upon metabolism. Such an analysis may alternatively, or additionally, be performed to identify the effects of a drug metabolite and/or pathophysiologic condition upon metabolism.

For example, a class of chemical matter designed to enhance carbohydrate metabolism advanced in early stage drug discovery might have a positive mechanism that is coupled to a negative toxicity. A steady state Φ screen applied to such matter might identify how the class as a whole change metabolism (for instance, an increase in carbohydrate oxidation ($V_{PDH}/V_{CS}$) and carbohydrate anaplerosis ($V_{PC}/V_{CS}$)) might be identified. If the positive or sought after effect were predominantly associated with increased anaplerosis, then this would identify/confirm a mechanism of the compound (expected or unexpected). Lead matter could then be rank ordered for those that shifted the $V_{PC}/V_{CS}$ towards higher values. Alternatively, if it was noted that an increase in carbohydrate anaplerosis was associated with concomitant increase in carbohydrate oxidation ($V_{PDH}/V_{CS}$) and that increased oxidative cell injury, then candidate chemical matter could also be secondarily rank ordered to maximize $V_{PC}/V_{CS}$ while minimizing $V_{PDH}/V_{CS}$. Such a high-content screen could more rapidly narrow down the search for chemical matter as well as identify new and potentially less toxic downstream targets.

An illustrative and non-limiting use of the mass spectrometry techniques described herein will now be described. It will be appreciated that none of the experimental techniques described below are necessarily required or otherwise limiting, and are described merely to provide a descriptive example of one possible metabolite analysis procedure that may be performed utilizing the mass spectrometry techniques described above.

Illustrative Isotopomer Study

In the illustrative study, INS-1 cells (an insulin secreting beta cell derived line) were initially pre-incubated in DMEM medium and supplemented with glucose (2.5, 5, 7 and 9 mM), glutamine (4 mM), pyruvate (0.05 mM) and lactate (0.45 mM) for 2 h to reach metabolic steady state prior to the incorporation of labels. In this illustrative study, labels are additional neutrons applied to natural carbon atoms to produce carbon-13 atoms. The INS-1 cells were then washed with glucose-free DMEM medium and subsequently incubated with 2.5, 5, 7 or 9 mM of [U-$^{13}C_6$]glucose. Cells were quenched at different times (n=6 per time point) by a rapid wash with ice-cold PBS and then collected in 15 μl of an ice-cold solution containing 20% methanol, 0.1% formic acid, 1 mM phenylalanine, 3 mM NaF, 100 uM EDTA and 10 μM $^2H_4$-taurine (CDN Isotopes) as a load control. All the samples were lyophilized and resuspended in 50 μL of water prior to the LC-MS/MS (Liquid Chromatography-Mass Spectrometry) analysis described below.

In the illustrative study, samples were injected onto a Hypercarb column (3 μm particle size, 3×150 mm) at a flow rate of 1 mL/min and separated isocratically. Samples were ionized by electrospray into a ABSCIEX QTRAP LC-MS/MS system equipped with a SelexION for differential mobility separation (DMS) and acquired using multiple reaction monitoring (MRM) in negative mode. The source parameters were CUR: 30, CAD: high, IS: −1500, TEM: 625, GS 1: 50 and GS2: 55. DMS parameters were DT: low, MD: 2-propanol, MDC: low, DMO: 3 and DR: off. Retention times were confirmed with known standards and peaks integrated using Multiquant (ABSCIEX) using the individual MRM transition pairs ($Q_1/Q_3$) and mobile phase composition for each metabolite.

The metabolites examined in the illustrative analysis are listed in the table of FIG. 8. Table 800 lists, for each metabolite: MRM transition pairs ($Q_1/Q_3$), daughter ion carbon atoms analyzed in each fragment, mobile phase, and approximate SV-CoV pair values utilized during analysis (where SV refers to Separation Voltage, and CoV refers to Compensation Voltage (CoV)).

In table 800, M+n refers to the molecular weight (M) plus a number of carbon-13 atoms present (n). The parent/daughter masses are written as $M_{parent}/M_{daughter}$ under the $Q_1/Q_3$ column in table 800. For instance, the Malate M+1 isotopomer has a parent mass of 134 and a daughter mass of 116, written as "134/116."

In the illustrative analysis, fragments were identified using $^{13}C$-labeled standards. DMS was used as an orthogonal separation axis for pyruvate, lactate, malate, aspartate, PEP, glyceraldehyde 3-phosphate, succinate and dihydroxyacetone phosphate to eliminate unknown isobaric contributions generated in the presence of mass label. Separation Voltage (SV) and Compensation Voltage (CoV) for each metabolite was optimized before each experiment. The atomic percent excess (APE) was calculated as the quotient between each $Q_1/Q_3$ area and the sum of all $Q_1/Q_3$ areas from each metabolite multiplied by 100. The values obtained from time=0 min were used to subtract background noise and adjust for natural abundance. Endogenous taurine, an intracellular osmolyte, was used as an internal control for cell density. In the illustrative analysis, $^{13}C$ incorporation into taurine did not occur, nor did the absolute concentration of taurine change during the incubations. The atomic percent excess (APE) was calculated, and background and natural abundance corrected from an isotopomer matrix accounting for the presence of natural abundance carbons distributed throughout each possible parent/daughter ion combination (as discussed further below).

a) Configuration of Differential Mobility Separation (DMS)

A differential mobility filter to isolate entire isotopomer families was empirically optimized by generating multidimensional maps of (m±n)/z (where m is the mass of the metabolite, n is the greater of the number of carbons within the metabolite or interfering species, and z is the charge state) signal vs. separation parameters (e.g., not limited to the separation voltage, compensation voltage, DMS offset, DMS cell plate configuration, resolution gas, etc.) vs. the choice concentration, and temperature of a modifying gas, etc., for any condition that is used to introduce ions into the mass spectrometer. These maps were generated and compared to maps of potential isobars as well as the sample matrix to generate optimal separation parameters for each plurality of isotopomers of interest. The maps are then compared with one another and the DMS configured such that the full plurality of different isotopomers is allowed to simultaneously pass through the DMS cell as a group. As discussed above, a spectrometer configured as such may allow for a complete set of metabolic reaction rates to be determined.

In the illustrative analysis, a DMS may be configured to select the different isotopomers of a given metabolite using the following steps:

Coarse Tuning of DMS:

Chemical standards of molecules of interest as well as anticipated interfering isobaric species in the (m±n)/z range were pooled at 50 uM and directly introduced into the mass spectrometer. A 3-dimensional matrix of SV vs. CoV across the full m/z range of the pooled metabolites was acquired. Additional dimensions of these matrices were also acquired by changing modifier gas (e.g. methanol, isopropanol, acetone, N2, etc.) vs. temperature, vs. flow rate and then the multidimensional matrices were analyzed for maximal dispersion of the separation of the metabolites of interest from their potential isobars. Similarly, the full natural abundance sample matrix from prepared cell lysates was subjected to mapping to identify optimal dispersion.

With the root conditions determined, metabolites (of interest and isobars) were individually monitored by their MRM while SV vs. CoV matrices were built. Each of these two dimensional maps was superimposed with metabolites in the (m±n)/z mass range and conditions were chosen to maximize separation with sensitivity to serve as a starting point for the fine tune.

Fine Tuning the DMS:

Using predetermined Liquid Chromatography (LC) and Mass Spectrometry (MS) parameters (see above) to be used in the final method, the optimal DMS separations were determined under these conditions by performing column injections of individual metabolites. With each injection or series of injections, the full range of the SV vs. CoV matrices were re-determined by stepping the SV (e.g., 500 V steps) and CoV (e.g., 1 V steps). Once an approximate range of separation was determined the values were experimentally fine-tuned at an individual SV with smaller steps of the CoV (0.25 V). Injections of isobars were performed under these same conditions to ensure the specificity of the filtration. Before each analytical separation, this fine tune may be performed on a fully equilibrated instrument to ensure the fidelity of the separation.

As discussed above, operating a DMS in a standard configuration may not be sufficient to perform measurements of metabolite interconversion reactions within the time scales necessary to understand the biological processes underlying the reactions. As such, in the illustrative study the flow cell was not emptied and refilled between each isotopomer. Rather, all of the isotopomers selected by the DMS were selected for MS analysis.

If, instead, the DMS cell was allowed to fully empty between each detected ion, the cycling time of the instrument would be too long to acquire sample data within a single run. An individual metabolite or series of metabolites may have identical SV/CoV pairing, and/or some individual metabolites may have more than, say, 50 transitions detected. As such, with such long cycle lengths the acquired peak shape would be significantly different for transitions at the beginning vs. midpoint of the MRM series and would severely impact the desired deconvolvement of isotopomers. Acquiring data over multiple runs could otherwise lead to propagation of experimental error.

To mitigate or avoid these problems, the mass spectrometer was programmed to: i) pool together isotopomers sharing identical SV and CoVs within an individual experiment ("clutches") during the acquisition; ii) set pause times to a feasible minimum to maintain fidelity (empirically determined) to minimize cycle time (pause time+dwell time); and iii) set a delay time between each of the individual clutches to allow full clearance of the DMS cell with interposed non-acquisition scans (dummy scans) to allow DMS cell filling.

b) Quantitative Isotopomer Analysis

For the illustrative study, the analysis of metabolic fluxes was performed under the following assumptions:

Assumption 1: For the deconvolution of citrate isotopomers, only three turns of the TCA cycle were considered necessary for analysis (see FIG. 9). This assumption has been experimentally confirmed by the low percentage of citrate $M^{+1}$ expected in the third cycle.

Assumption 2: In an open system, bicarbonate does not contribute significantly to the labeling patterns.

Assumption 3: For calculating citrate and glutamate isotopomers, pyruvate is considered predominantly either $M^{+0}$ or $M^{+3}$. $M^{+2}$ pyruvate from pyruvate carboxylase (PC)-mediated pyruvate recycling will be mostly [2,3-$^{13}C_2$]pyruvate and will label acetyl-CoA the same as $M^{+3}$. Other $M^{+1}$ and $M^{+2}$ labeled pyruvate is assumed to make an insignificant contribution (experimentally confirmed by low enrichments).

Assumption 4: Acetyl-CoA only contributes carbons to the Pro-S carbons of citrate.

Assumption 5: For the analysis of citrate, aspartate and OAA (oxalacetic acid) enrichments, OAA and fumarate are assumed to be in near-equilibrium. Therefore, for any given isotopomer of aspartate, OAA and malate there is an equal percentage of the symmetrical isotopomer. This was confirmed by the modeling fluxes ($V_{SC} \gg V_{CS}$, See table of FIG. 8) and by $^{13}C$-NMR analysis of glutamate C3 and C2 (C3/C2=0.96±0.06).

In addition, a natural abundance correction was performed to the experimental data based on a value of 1.1%. Specifically, a corrected isotopomer matrix, $l'_{(P_m,D_n)}$, was generated to account for the presence of natural abundance carbons for each possible parent/daughter ion combination of the positive matrix $l'_{(P_m,D_n)}$. The matrix $l'_{(P_m,D_n)}$ indicates the peak l area measured in a mass spectrometer corresponding to a parent ion P and a daughter ion D, and is corrected as follows:

$$l'_{(P_m,D_n)} = l_{(P_m,D_n)} * (1+k(p-m)) - l_{(P_{m-1},D_n)} * k((p-d)-(m-n-1)) - l_{(P_{m-1},D_{n-1})} * k(d-(n-1)) \quad \text{(Eqn. 1)}$$

where p is the total number of carbons in the parent ion, d is the total number of carbons in the daughter ion, m is the number of $^{13}C$ in the parent ion, n is the number of $^{13}C$ in the daughter ion, l is the peak area corresponding to parent ion with mass P from 0→p and daughter ion with mass D from 0→d, k is 0.011 (the natural abundance of $^{13}C$ in the environment), and m−n≤p−d.

i) Deconvolution of Citrate Isotopomers

The principles and derivation of mass isotopomeric deconvolution for the indicated metabolites are described below. The enrichments of citrate isotopomers were calculated from the 191/67 fragment family according to Eqn. 2 through Eqn. 11 below. Prior to calculation of citrate isotopomer families, the citrate spectrum was corrected for C6 loss from reversible exchange across isocitrate dehydrogenase (ICDH).

Figure 9:
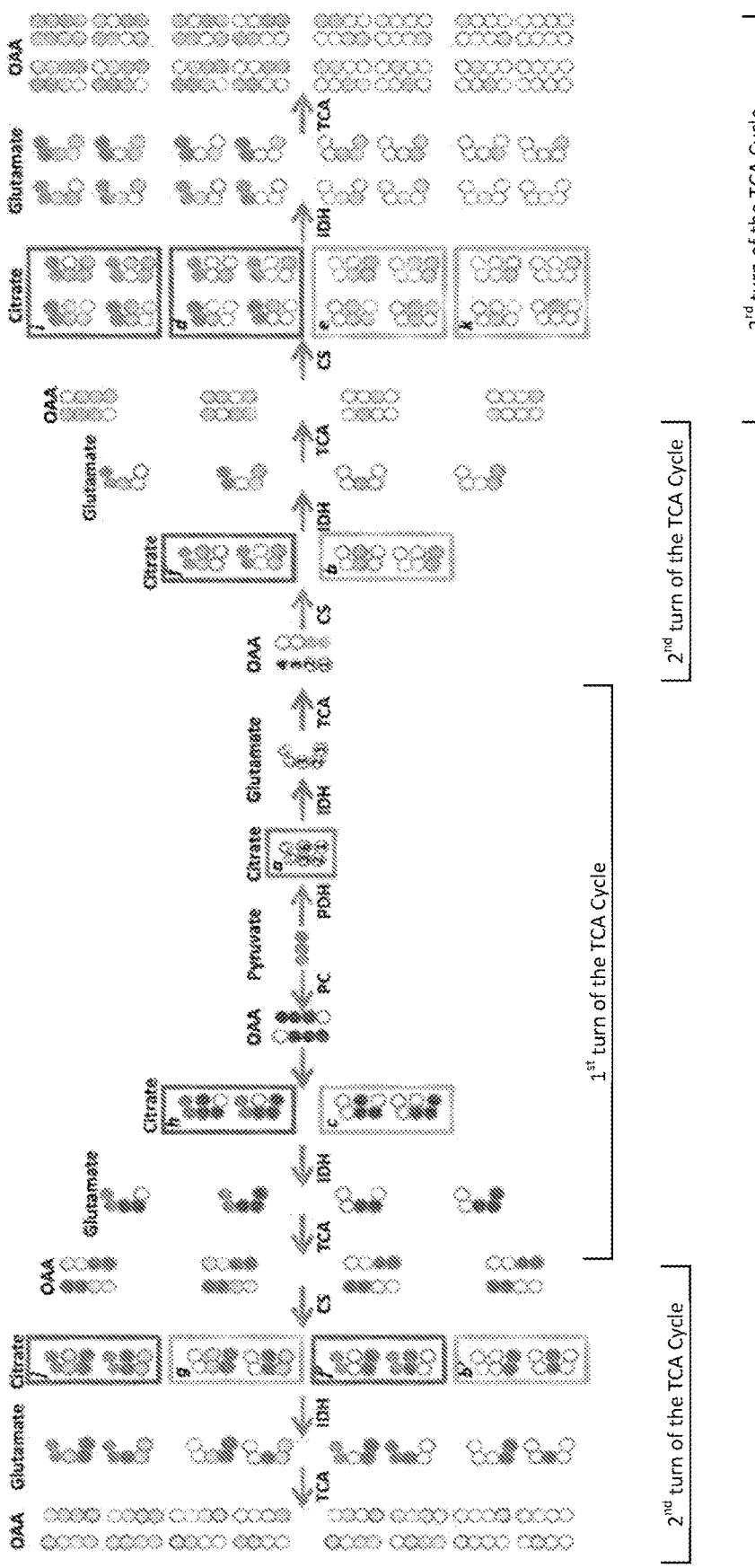
FIG. 9 illustrates isotopomers generated during $1^{st}$, $2^{nd}$ and $3^{rd}$ turns of the TCA cycle considered in an illustrative analysis, according to some embodiments.

Citrate is a symmetric molecule but it contains a prochiral center that can be stereochemically distinguished by enzymes of the TCA cycle. The recognition of positional transfer of labeled carbons from metabolite to metabolite in the TCA cycle forms the basis of these flux experiments. Rather than using standard prochiral nomenclature to identify the carbons, citrate carbons are numbered as shown in FIG. 9 (see citrate molecule $Cit_a$ at the center of the figure). This allows easier comparison of the positional transfer of labeled carbons from those metabolites with prochirality (e.g., citrate, fumarate) to those without (e.g., succinate, malate, glutamate).

Isotopomers generated during the $1^{st}$, $2^{nd}$ and $3^{rd}$ turns of the TCA cycle considered in this analysis are shown in FIG. 9. Citrate isotopomers were grouped into families depending on whether the label is originated from PDH flux only ($Cit_a$, $Cit_f$, $Cit_b$, $Cit_i$, $Cit_d$, $Cit_e$ and $Cit_k$) or from both pyruvate dehydrogenase (PDH) and pyruvate carboxylase (PC) fluxes ($Cit_b$, $Cit_c$, $Cit_j$, $Cit_g$, $Cit_f$, and $Ch_b$).

Acetyl-CoA generated via β-oxidation or the PDH reaction contributes carbons 4 and 5 (per this numbering scheme) while those derived from OAA provide carbons 1, 2, 3 and 6. The metabolism of $[U-^{13}C_6]$glucose will generate $[U-^{13}C_3]$pyruvate that then enters the TCA cycle via either PDH (dark grey in the right hand half of the figure) or PC (dark grey in the left hand half of the figure). As these labeled pyruvate carbons flow through subsequent turns of the TCA cycle, additional labeling patterns are generated (light grey). All of the isotopomers generated by $^{13}C$ carbons coming from PDH flux can be measured if all of the isotopomers with $^{13}C$ in positions 4,5 (in FIG. 9, carbons indicated in dark grey within the citrate isotopomer families $cit_{a,d,f,h,t,j}$) can be measured. Similarly, PC-derived carbons are represented by isotopomer families $cit_{c,h}$ (also shown in dark grey in FIG. 9). The division of the citrate isotopomers into families is based on the condensation of OAA with labeled or unlabeled acetyl-CoA. Within each family all the isotopomers have equal probability (assumption 5 above). These stoichiometric relationships make it possible to fully deconvolve citrate isotopomers.

Figure 10A:
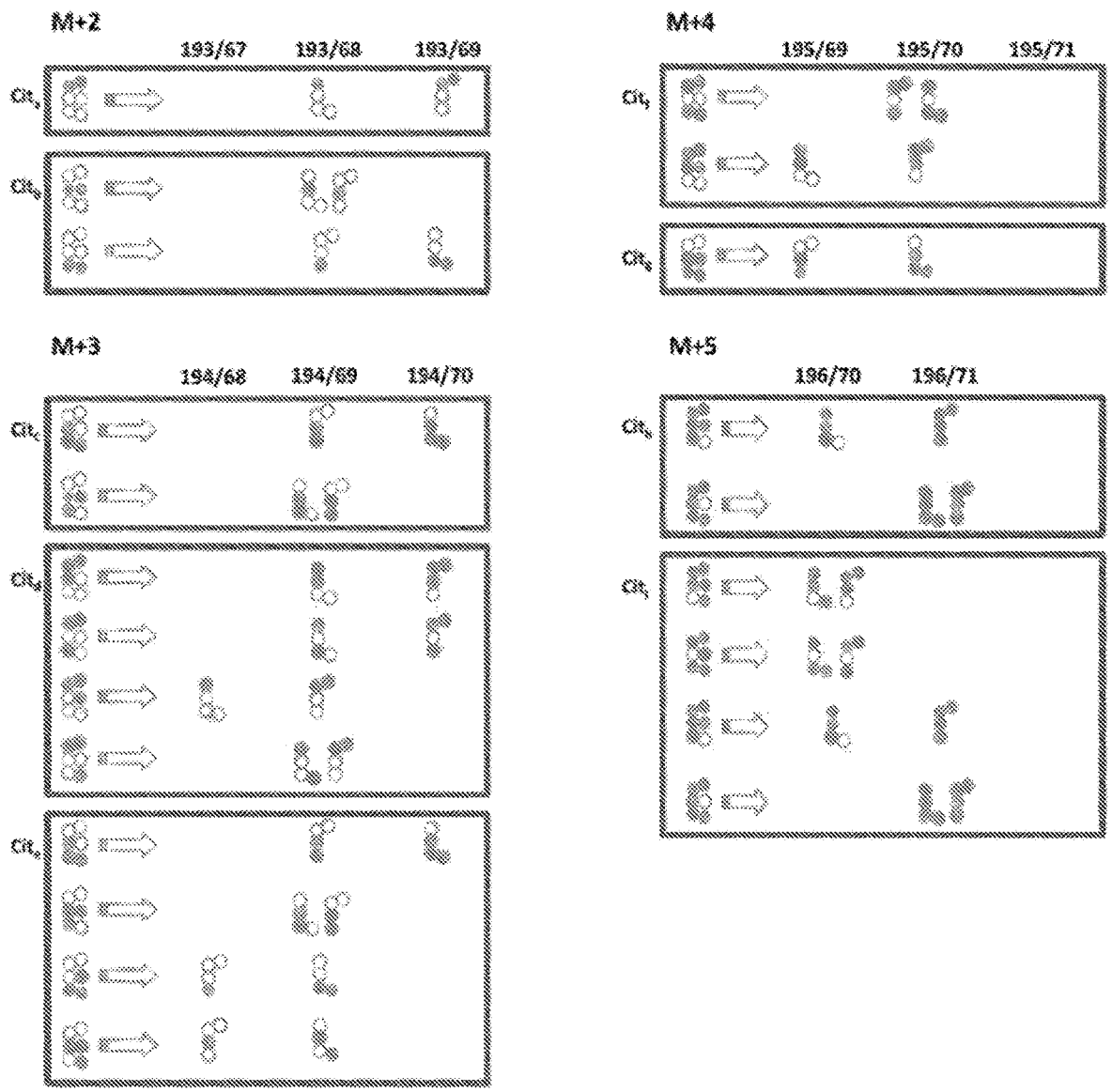
FIG. 10A depicts parent/daughter distributions of the citrate fragments for $M^{+2}$, $M^{+3}$, $M^{+4}$ and $M^{+5}$ for an illustrative analysis, according to some embodiments.
Figure 10B:
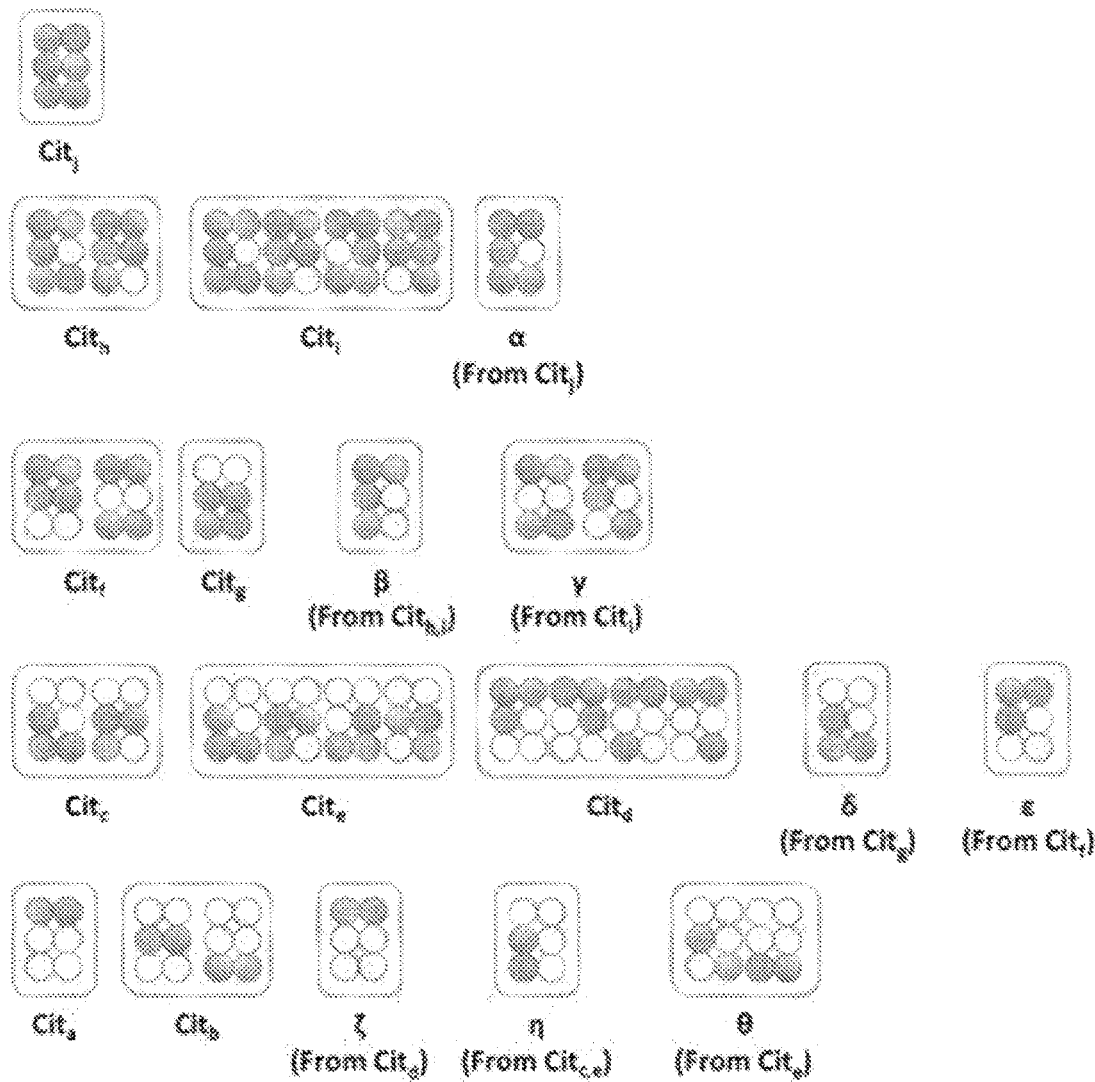
FIG. 10B illustrates citrate isotopomers generated by reverse ICDH for an illustrative analysis, according to some embodiments.

Citrate prochirality, while recognizable by enzymes, does not alter fragmentation patterns. Any asymmetric fragmentation of a citrate parent ion has equal probability of generating of pro-S and pro-R daughters. The 191/67 citrate parent/daughter anion occurs from the loss of carbons C1,6, and with equal probability carbons C5,6. The fragmentation patterns of the citrate mass isotopomer families generated from uniformly labeled pyruvate are shown in FIG. 10A, which depicts parent/daughter distributions of the citrate fragments for $M^{+2}$, $M^{+3}$, $M^{+4}$ and $M^{+5}$, according to some embodiments. FIG. 10B illustrates citrate isotopomers generated by reverse ICDH, according to some embodiments.

The assignments of the parent/daughter combinations for the individual $M^{+2}$ to $M^{+6}$ mass isotopomer families is described below:

Citrate $M^{+2}$: There are three ways to generate $M^{+2}$ labeling of citrate: from PDH to generate $cit_a$ as well as from second cycle TCA from either PDH or PC flux to generate the indistinguishable families $cit_b$ and $cit_b$. Because they do not provide unique flux information, for simplicity they will be collapsed into the single term $cit_b$ representing the combination (FIG. 9). Fragmentation of family $cit_a$ will generate equal amounts of 193/68 and 193/69 daughters. Fragmentation of $cit_b$ generates three 193/68 daughters for every one 193/69 daughter. Therefore, the excess 193/68 is attributable to family $cit_b$. Based on the distribution of the fragments (FIG. 10A) we can derive the equations describing the isotopomer composition of each $Q_1/Q_3$ parent daughter combination:

$$193/60 = \frac{a}{2} + \frac{3b}{4}$$

$$193/69 = \frac{a}{2} + \frac{b}{4}$$

Above, a represents the isotopomers from labeled acetyl-CoA with $[4,5-^{13}C_2]$ labeled, and b is the combination of $[3,6-^{13}C_2]$ and $[1,2-^{13}C_2]$ both arising from second cycle (from either PDH or PC flux). From Assumption 5 described above, the enrichments of $[1,2-^{13}C_2]$citrate and $[3,6-^{13}C_2]$ citrate are assumed to be equal and reduce to a single term represented as $[\Sigma(1,2)(3,6)-^{13}C_2]$citrate. The enrichments of the possible isotopomers considered for $M^{+2}$ are then calculated according to Eqn. 2 and Eqn. 3 after solving for a and b, respectively.

$cit_a = [4,5-^{13}C_2]Citrate = 3*193/69 - 193/68$ (Eqn. 2)

$cit_b = [\Sigma(3,6)(1,2)-^{13}C_2]Citrate = 2*(193/68 - 193/69)$ (Eqn. 3)

Citrate $M^{+3}$: Three groups of citrate $M^{+3}$ isotopomers come from PC ($cit_c$), PDH $M^{+2}$ plus $M^{-1}$ OAA ($cit_d$), and the four possible M+3 OAA patterns coming from second cycle of $cit_f$ (family $cit_e$). Based on the distribution of the fragments we can derive the equations describing the isotopomer composition of each $Q_1/Q_3$ parent daughter combination:

$$194/68 = \frac{1}{8}d + \frac{2}{8}e$$

$$194/69 = \frac{3}{4}c + \frac{5}{8}d + \frac{5}{8}e$$

$$194/70 = \frac{1}{4}c + \frac{2}{8}d + \frac{1}{8}e$$

The enrichments of all the isotopomers considered for $M^{+3}$ are calculated according to equations 4-6 (after solving for c, d and e, respectively).

$cit_c = [\Sigma(1,2,3)(2,3,6)-^{13}C_3]Citrate = 3*194/69 - 5*194/68 - 5*194/70$ (Eqn. 4)

$cit_d = [\Sigma(1,4,5)(2,4,5)(3,4,5)(6,4,5)-^{13}C_3]Citrate = 4*194/68 - 4*194/69 + 12*194/70$ (Eqn. 5)

$cit_e = [\Sigma(1,2,3)(2,3,6)(1,1,6)(1,3,5)-^{13}C_3]Citrate = 2*194/68 + 2*194/69 - 6*194/70$ (Eqn. 6)

Citrate $M^{+4}$: There are two $M^{+4}$ isotopomer families. The first, $cit_f$, comes from $[1,2-^{13}C_2]$Acetyl-CoA from PDH flux combined with the second turn of the TCA cycle carrying forward the condensation of OAA labeled from PDH. Alternatively, the same labeling pattern is generated by first cycle PDH combined with second cycle PC ($cit_f$). The families $cit_f$ and $cit_f$ are indistinguishable and therefore collapsed into a single isotopomer family ($cit_f$). Family $cit_g$ arises during the second turn of the TCA cycle from the condensation of $M^{+4}$ OAA coming (from $cit_h$) with unlabeled acetyl-CoA. Based on the distribution of the fragments we can derive the equations describing the isotopomer composition of each $Q_1/Q_3$ parent daughter combination:

$$196/69 = \frac{1}{4}f + \frac{1}{2}g$$

$$195/70 = \frac{3}{4}f + \frac{1}{2}g$$

The enrichments of all the isotopomers considered for $M^{+4}$ are calculated according to equations 7 and 8 after solving for f and g, respectively.

$$cit_f = [\Sigma(1,2,4,5)(3,6,4,5)\text{-}^{13}C_4]\text{Citrate} = 2*1.95/70 - 2*195/69 \quad \text{(Eqn. 7)}$$

$$cit_g = [1,2,3,6\text{-}^{13}C_4]\text{Citrate} = 3*1.95/69 - 195/70 \quad \text{(Eqn. 8)}$$

Citrate $M^{+5}$: There are two families of $M^{+5}$ isotopomers. Family $cit_h$ results from the combination of PC and PDH fluxes during the first turn of the TCA cycle. Family cit, arises from labeled PDH flux plus the recycling of family $cit_f$ during the third turn of the TCA cycle. Based on the distribution of the fragments the equations describing the isotopomer composition of each $Q_1/Q_3$ are:

$$196/70 = \frac{1}{4}h + \frac{5}{8}i$$

$$196/71 = \frac{3}{4}h + \frac{3}{8}i$$

The enrichments of all the isotopomers considered for $M+^5$ are calculated according to Eqns. 9 and 10 after solving for h and i, respectively.

$$cit_h = [\Sigma(1, 2, 3, 4, 5)(2, 3, 6, 4, 5) - {}^{13}C_5]\text{Citrate} = \quad \text{(Eqn. 9)}$$
$$\frac{5}{3} = 196/71 - 196/70$$

$$cit_i = [\Sigma(1, 2, 3, 4, 5)(2, 3, 6, 4, 5)(1, 3, 6, 4, 5)(1, 2, 6, 4, 5) - \quad \text{(Eqn. 10)}$$
$${}^{13}C_5]\text{Citrate} = 2*196/70 - \frac{2}{3}*196/71$$

Citrate $M^{+6}$: This family contains a single member formed from the condensation of OAA derived from $cit_h$ with $[1,2\text{-}^{13}C_2]$Acetyl-CoA. It gives a unique fragmentation pattern (197/71):

$$cit_j = [1,2,3,4,5,6\text{-}^{13}C_6]\text{Citrate} = 197/71 \quad \text{(Eqn. 11)}$$

ii) Correction for Isocitrate Dehydrogenase Exchange

This deconvolution assumes a direct flow of carbons from citrate to aKG. However, the existence of a reversed flow through ICDH creates an exchange between citrate and aKG. The practical implication is that the reversed flux through ICDH will impact the labeling patterns of citrate (FIG. 10B). Because bicarbonate is assumed to not contribute significantly to the labeling patterns, the reverse flux through ICDH will only affect citrate isotopomers containing $^{13}C$ in position 6. For instance, the decarboxylation of $[U\text{-}^{13}C_6]$citrate yields $[1,2,3,4,5\text{-}^{13}C_5]$aKG, which through reverse ICDH generates $[1,2,3,4,5\text{-}^{13}C_5]$ citrate that was not originated by $[1,2,3\text{-}^{13}C_3]$OAA. Because the label in carbons 4 and 5 is not affected by reverse ICDH, the relevance of this flux is proportional to the ratio between the sum of all $[4,5\text{-}^{13}C]$ isotopomers ($\Sigma\ Cit_a$, $Cit_f$, $Cit_i$, $Cit_h$, $Cit_d$, $Cit_j$) and $[1,2\text{-}^{13}C_2]$acetyl-CoA, defined as $\Phi_{AcCit}$ (Isotopic Steady-State Relationships). The following equations use $\Phi_{AcCit}$ to correct the area of each Q1/Q3 citrate fragments in order to account for the reverse ICDH flux:

$M^{+6}$ $$197/71_c = \frac{197/71}{\Phi_{AcCit}}$$

$M^{+5}$ $$196/71_c = 196/71 - 197/71(1 - \Phi_{AcCit}) + 195/71$$

$$196/70_c = \frac{196/70}{\Phi_{AcCit}}$$

$M^{+4}$ $$195/70_c = 195/70 - 196/70(1 - \Phi_{AcCit}) + 195/69(1 - \Phi_{AcCit})$$

$$195/69_c = \frac{195/69}{\Phi_{AcCit}}$$

$M^{+3}$ $$194/70_c = 194/70 - 195/69(1 - \Phi_{AcCit})$$

$$194/69_c = 194/69 - 195/69(1 - \Phi_{AcCit}) + 194/68(1 - \Phi_{AcCit}) + 193/67$$

$$194/68_c = \frac{194/68}{\Phi_{AcCit}}$$

$M^{+a}$ $$193/69_c = 193/69 - 194/68(1 - \Phi_{AcCit})$$

$$193/68_c = 193/68 - 194/68(1 - \Phi_{AcCit}) + (193/68 - 193/69)(1 - \Phi_{AcCit})$$

iii) Deconvolution of Glutamate Isotopomers

Further metabolism of citrate to aKG in the TCA cycle results in loss of C6 of citrate but C1-C5 retain their positional labeling. aKG is in rapid exchange (via reversible transamination or via anaplerotic entry via GDH) with glutamate—a highly concentrated and commonly used surrogate of the TCA cycle.

Carbons 4 and 5 coming from acetyl-CoA are directly measured in the 2-carbon 146/41 daughter. This fragment effectively divides glutamate into its two precursor components: acetyl-CoA (glutamate C4 and C5) and OAA (glutamate C1-C3). Consequently, all of the glutamate isotopomers with daughters of 41 have no enrichment)($Glu_{C4,5}^{0}$, with daughters of 42 are $M^{+1}$ enriched ($Glu_{C4,5}^{+1}$), and 43 are $M^{+2}$ enriched ($Glu_{C4,5}^{+2}$). It is not possible to determine the position of the enriched carbon in $Glu_{C4,5}^{+1}$.

Because of the lack of additional positional enrichment in carbons 1-3 from the fragmentation, only the isotopologues of this fragment can be assessed (M, $M^{+1}$, $M^{+2}$, $M^{+3}$). While there is no unique solution for the $M^{+1}$ and $M^{+2}$ isotopologues of the C1-3 glutamate fragment, $[U\text{-}^{13}C_4]$OAA and $[2,3,4\ {}^{13}C_3]$OAA (but not $[1,2,3\ {}^{13}C_3]$OAA) are the precursors for the $M^{+3}$ labeled C1-3 of glutamate.

Glutamate C4,5 Isotopologues:

$$Glu_{C4,5}{}^0=[C4,5^{13}C_0]glutamate=\Sigma(146/41,147/41,148/41,149/41) \quad \text{(Eqn. 12)}$$

$$Glu_{C4,5}{}^{+1}=[C4,5^{13}C_1]glutamate=\Sigma(147/42,148/42,149/43,150/42) \quad \text{(Eqn. 13)}$$

$$Glu_{C4,5}{}^{+2}=[C4,5^{13}C_2]glutamate=\Sigma(148/43,149/43,150/43,151/43) \quad \text{(Eqn. 14)}$$

Glutamate C1-3 Isotopologues $$Glu_{C1,2,3}{}^0=[C1,2,3^{13}C_0]glutamate=\Sigma(146/41,147/42,148/43) \quad \text{(Eqn. 15)}$$

$$Glu_{C1,2,3}{}^+=[C1,2,3^{13}C_1]glutamate=\Sigma(147/41,148/42,149/43) \quad \text{(Eqn. 16)}$$

$$Glu_{C1,2,3}{}^{+2}=[C1,2,3^{13}C_2]glutamate=\Sigma(148/41,149/42,150/43) \quad \text{(Eqn. 17)}$$

$$Glu_{C1,2,3}{}^+=[C1,2,3^{13}C_3]glutamate=\Sigma(149/41,150/42,151/43) \quad \text{(Eqn. 18)}$$

In the illustrative analysis, the inability to discern positional labeling within the daughter ion containing C1-3 limits the possibility of fully deconvolving this metabolite.

iv) Deconvolution of Succinate Isotopomers

Succinate is an excellent readout of TCA cycle activity. It is formed almost exclusively in the mitochondria. Unlike malate and fumarate, the labeling pattern of succinate is not directly affected by PC flux since succinic dehydrogenase (SDH) is unidirectional and doesn't receive carbons from fumarate under normal conditions.
Therefore, succinate labeling is a consequence of label passing through citrate synthase (CS). Since succinate is symmetric, $^{13}C$-label is evenly distributed across the molecule. The 117/73 fragment corresponds to the loss of either C1 or C4 (See FIG. 8) and can be used to obtain the positional enrichment of $^{13}C$-label:

Succinate M+1: There is an equal probability of $M^{+1}$ enrichment in all four carbons. The relationship 3×118/74=118/73 predicted based on the labeling scheme was observed. See FIG. 11 A.

Succinate M+2: Doubly labeled succinate will be equally label C1,2 and C3,4 with other combinations not likely. Here, 119/74 closely approximates 119/75 at all times See FIG. 11B.

Succinate M+3: There are four possible labeling patterns for $M^{+3}$ succinate: $[(1,2,3)(2,3,4)(1,3,4)(1,2,4)-^{13}C_3]$. These four isotopomers arise from Cit$_t$ and thus have equal probability of occurring. For this reason, the predicted relationship 120/75=120/76×3 is confirmed and rules out the contribution of meaningful reverse labeling of succinate See FIG. 11C.

Succinate M+4: There is only one possible fragmentation pattern: 120/76 iv) Deconvolution of Malate Isotopomers

In the illustrative analysis, the fragment used to study malate is the result of a dehydrogenation and contains all four carbons (See FIG. 8) and thus positional enrichments cannot be resolved.

Positional enrichments for $M^{+3}$ are needed to distinguish $[(1,2,3)(2,3,4)-^{13}C_3]$malate generated through PC, from $[(1,2,3)(2,3,4)(1,2,4)(1,3,4)-^{13}C_3]$malate generated within the TCA cycle. The isotopomers, however, can be deduced considering the irreversibility of SDH under most physiological states. Since there is no direct PC generated $M^{+3}$ label contribution to succinate then malate can be corrected by a weighted subtraction of succinate enrichments: $[(1,2,3)(2,3,4)(1,2,4)(1,3,4)-^{13}C_3]$malate is predicted based from $[(1,2,3)(2,3,4)(1,2,4)(1,3,4)-^{13}C_3]$succinate (Eqn. 19). In this calculation, the dilution between the malate and succinate pools must be accounted for. Because $[U-^{13}C_4]$malate can only be generated from $[U-^{13}C_4]$succinate, the ratio $[U-^{13}C_4]$malate/$[U-^{13}C_4]$succinate can be used as a correction factor for that dilution. The enrichments originating from the PC reaction, $[(1,2,3)(2,3,4)-[U-^{13}C_4]$malate, can then be obtained by subtraction from the total $M^{+3}$ enrichments (Eqn. 20). The malate enrichments obtained from equations 19 and 20 are very similar to the OAA enrichments.

$$[(1,2,3)(2,3,4)(1,2,4)(1,3,4)-^{13}C_3]\text{malate}=[(1,2,3)(2,3,4)(1,2,4)(1,3,4)-^{13}C_3]\text{succinate}*\frac{[U-^{13}C_4]\text{malate}}{[U-^{13}C_4]\text{succinate}} \quad \text{(Eqn. 19)}$$

$$[(1,2,3)(2,3,4)-^{13}C_3]\text{malate}=[^{13}C_3]\text{malate}-[(1,2,3)(2,3,4)(1,2,4)(1,3,4)-^{13}C_3]\text{malate} \quad \text{(Eqn. 20)}$$

iv) Deconvolution of Aspartate Isotopomers

De novo synthesis of OAA from pyruvate via PC incorporates natural abundance $CO_2$ into C4 in an open system (Assumption 2). If OAA is in near-equilibrium with malate across fumarase, this racemically scrambles this carbon between positions 1 and 4 (and carbon 2 with 3). Since aspartate and malate share OAA as a common intermediate, the equivalence of aspartate and malate $M^{+2}$ enrichments, arising from the turning of the TCA cycle, suggest these pools are in isotopic equilibrium with each other through OAA (See FIG. 11F). The asymmetric fragmentation of aspartate leads to loss of C4 (See FIG. 8) thus allowing positional assignment of label.

Aspartate $M^{+1}$: There is no advantage to deconvolving these isotopomers since there is an equal probability of $M^{+1}$ enrichment in all four carbons. Nevertheless, the relationship 3×133/88=133/89 is predicted based on the labeling scheme.

Aspartate $M^+{}_2$: Doubly labeled aspartate will be equally C1,2 and C3,4 with other combinations not likely. Here, 134/89 equals 134/90 confirming the expected symmetry (See FIG. 8).

Figure 11A:
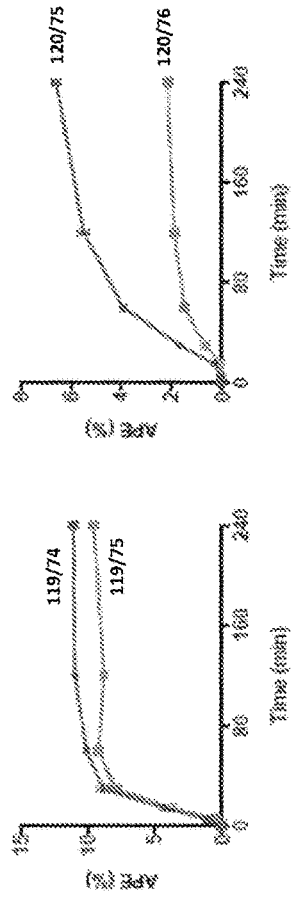
FIGS. 11A-11I illustrate time dependent C-enrichment of succinate, malate, OAA and aspartate fragments for an illustrative analysis, according to some embodiments.
Figure 11B:
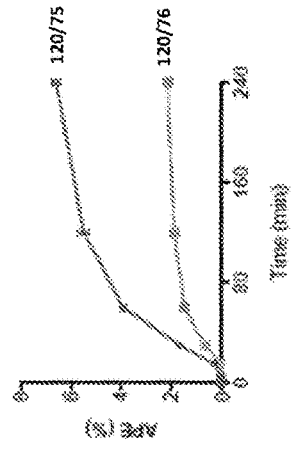
Figure 11C:
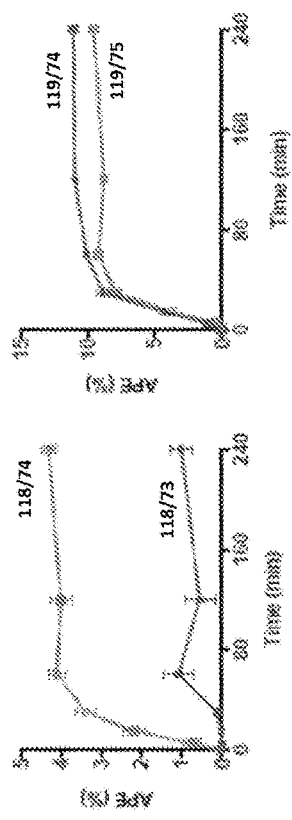
Figure 11D:
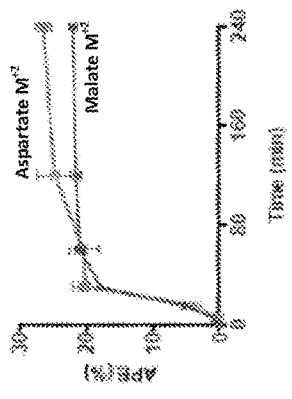
Figure 11E:
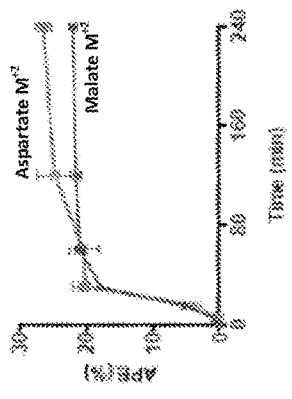
Figure 11F:
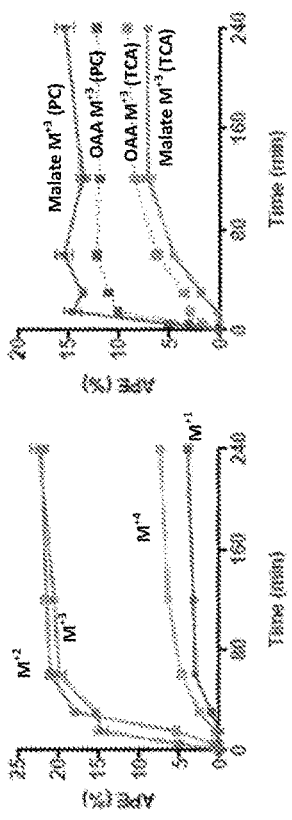
Figure 11G:
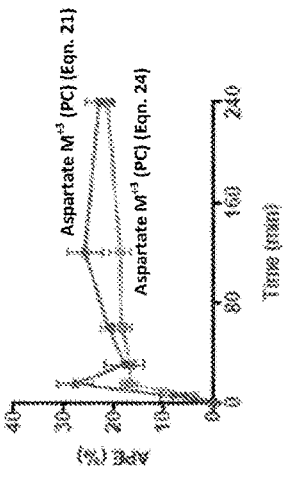
Figure 11H:
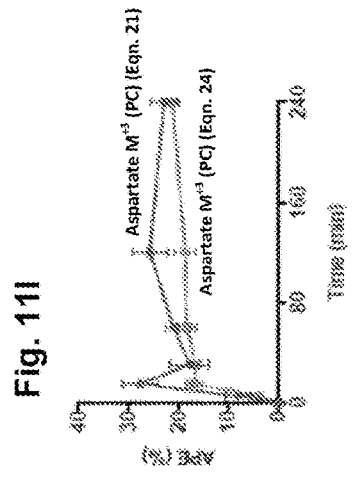
Figure 11I:
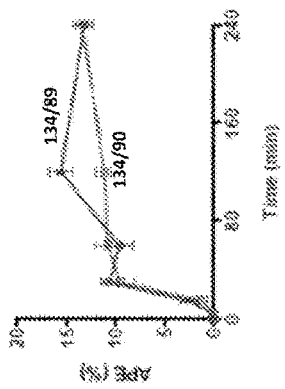

Aspartate $M^{+3}$: As with malate, there are two possible labeling patterns for M+3 aspartate. The $[(1,2,3)(2,3,4)-^{13}C_3]$ arising from PC flux and $[(1,2,3)(1,2,4)(1,3,4)(2,3,4)-^{13}C_3]$ generated within the TCA cycle. The former would generate equal amounts of 135/90 and 135/91. The latter, would generate three 135/90 for every 135/91. FIG. 11H shows the time courses for both 135/90 and 135/91. The amount coming from TCA, PC, and total $M^{+3}$ then are defined by the following:

$$[(1,2,3)(2,3,4)(1,2,4)(1,3,4)-^{13}C_3]\text{aspartate}=2*(135/90-135/91) \quad \text{(Eqn. 21)}$$

$$[(1,2,3)(2,3,4)-^{13}C_3]\text{aspartate}=3*(135/91)-(135/90) \quad \text{(Eqn. 22)}$$

$$[^{13}C_3]\text{aspartate}=(135/90+135/91) \quad \text{(Eqn. 23)}$$

Alternatively, $[(1,2,3)(2,3,4)-^{13}C_3]$aspartate can also be determined using the same principle described above to calculate malate $M^{+3}$ isotopomers.
Therefore, $[(1,2,3)(2,3,4)(1,2,4)(1,3,4)-^{13}C_3]$ and $[(1,2,3)(2,3,4)-^{13}C_3]$aspartate were calculated according to equations 24 and 25. Both approaches yield similar results (See FIG. 11I).

$$[(1, 2, 3)(2, 3, 4)(1, 2, 4)(1, 3, 4) - {}^{13}C_3] \quad \text{(Eqn. 24)}$$
$$\text{aspartate} = [(1, 2, 3)(2, 3, 4)(1, 2, 4)(1, 3, 4) - {}^{13}C_3]$$
$$\text{succinate} * \frac{[U - {}^{13}C_4]\text{aspartate}}{[U - {}^{13}C_4]\text{succinate}}$$

$$[(1, 2, 3)(2, 3, 4) - {}^{13}C^3]\text{aspartate} = [{}^{13}C_3]\text{aspartate} - \quad \text{(Eqn. 25)}$$
$$[(1, 2, 3)(2, 3, 4)(1, 2, 4)(1, 3, 4) - {}^{13}C_3]\text{aspartate}$$

Aspartate $M^{+4}$: There is only one possible fragmentation pattern: 136/91 c) Calculation of Acetyl-CoA and OAA Enrichments

The fractional enrichments of the mitochondrial matrix pool of acetyl-CoA and OAA were calculated using mass isotopologue distribution analysis. Enrichments were calculated from either glutamate or citrate isotopomers according to the description above.

The relative contribution of glucose oxidation and β-oxidation to the acetyl-CoA used by citrate synthase can be determined if both pyruvate and acetyl-CoA enrichments are known. While in practice, directly measuring the fractional enrichment of the mitochondrial matrix pool of acetyl-CoA and OAA can be a challenge, it is nonetheless possible using mass isotopomer distribution analysis (MIDA).

In a reaction where two substrates (A and B) combine to form a product (AB), if both substrates are fractionally enriched ($FE_{A*}$ and $FE_{B*}$), then MID A determines the enrichment of both precursors even if there is dilution from outside unlabeled product. For the reaction A+B-→AB the fractional enrichment of the substrates are defined as $$FE_{A*} = \left(\frac{A^*}{A + A^*}\right) \quad \text{(Eqn. 26)}$$

$$FE_{B*} = \left(\frac{B^*}{B + B^*}\right) \quad \text{(Eqn. 27)}$$

where (*) designates the presence of a measurable label.

The reaction of (A+A*) with (B+B*) will generate the populations of $$AB + A^*B + AB^* + A^*B^* = 1 \quad \text{(Eqn. 28)}$$

by their binomial distribution even if there is a contaminating source of unlabeled product (A'B') as described by Eqn. 29.

$$AB + A^*B + AB^* + A^*B^* + A'B' = 1 \quad \text{(Eqn. 29)}$$

The probability of generating the doubly labeled product ($D_{A*B*}$) and singly labeled substrates ($S_{A*B}$ and $S_{A\ B*}$) are determined by the fractional enrichments in the compartment where the product is formed:

$$D_{A*B*} = \left(\frac{A^*}{A + A^*}\right) * \left(\frac{B^*}{B + B^*}\right) \quad \text{(Eqn. 30)}$$

$$S_{A*B} = \left(\frac{A^*}{A + A^*}\right) * \left(\frac{B}{B + B^*}\right) \quad \text{(Eqn. 31)}$$

$$S_{AB*} = \left(\frac{A}{A + A^*}\right) * \left(\frac{B^*}{B + B^*}\right) \quad \text{(Eqn. 32)}$$

The ratio of singly to doubly labeled products is described by equations 33 and 34.

$$\frac{S_{AB*}}{D_{A*B*}} = \frac{A}{A^*} \quad \text{(Eqn. 33)}$$

$$\frac{S_{A*B}}{D_{A*B*}} = \frac{B}{B^*} \quad \text{(Eqn. 34)}$$

Solving equations 33 and 34 for A and B and then substituting into the equations for the fractional enrichments, the $FE_{A*}$ and $FE_{B*}$ (Eqns. 26 and 27) are determined:

$$FE_{A*} = \frac{1}{\frac{S_{AB*}}{D_{A*B*}} + 1} \quad \text{(Eqn. 35)}$$

$$FE_{B*} = \frac{1}{\frac{S_{A*B}}{D_{A*B*}} + 1} \quad \text{(Eqn. 36)}$$

Citrate (and subsequently glutamate) is formed in the mitochondrial matrix via citrate synthase through the condensation acetyl-CoA and OAA. Unlike NMR, mass spectroscopy evaluates individual molecules. Therefore, it is possible determine $D_{A*B*}$, $S_{A\ B*}$, and $S_{A*B}$ from isotopomer deconvolution (see Deconvolution of Citrate Isotopomers). There are several potential ways to calculate the fractional enrichments of both acetyl-CoA ($FE_{A*}$) and OAA ($FE_{B*}$) in the mitochondrial matrix. FIG. 12 shows a numbered list of equivalent alternatives to calculate [1,2-$^{13}C_2$]acetyl-CoA from a citrate and glutamate isotopomer analysis.

In practice, options (5) and (9) shown in FIG. 12 may provide the best possible signal/noise and in the illustrative analysis were used to calculate [1,2-$^{13}C_2$]acetyl-CoA from citrate and from glutamate. Of note, they are similar at steady state (Citrate 80+2% vs. Glutamate 86+2%, N.S.). MIDA can also be applied to calculate the mitochondrial enrichments of OAA. Since one OAA carbon is lost in the conversion of citrate into glutamate, then it may not be possible to calculate the relative OAA isotopomers from glutamate using these data.

Together, the enrichments of several citrate isotopomers can be calculated based on the steady-state enrichments of OAA and acetyl-CoA. Any given citrate isotopomer is the result of the product between OAA and acetyl-CoA enrichments. For instance, [U-$^{13}C_6$]citrate is the product of [U-$^{13}C_4$]OAA and [1,2-$^{13}C_2$]acetyl-CoA.

Figure 13:
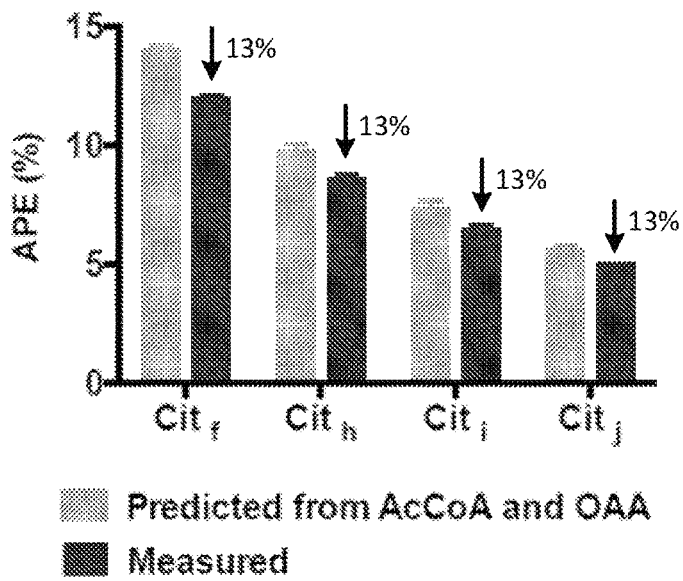
FIG. 13 illustrates a comparison between stead state enrichments of $Cit_f$, $Cit_h$, $Cit_i$ and $Cit_j$ predicted by the enrichments of OAA and acetyl-CoA and those calculated in an illustrative analysis, according to some embodiments.

FIG. 13 compares the predicted steady-state enrichments of $Cit_f$, $Cit_h$, $Cit_i$ and $Cit_j$ to those measured in Deconvolution of Citrate Isotopomers. The use of OAA and acetyl-CoA isotopic data overestimates the citrate isotopomer enrichments by approximately 13%. This consistent overestimation of the enrichments further emphasizes the argument in favor of the equilibration of citrate with ocKG through reversed ICDH.

d) Isotopic Steady-State Relationships

In the illustrative analysis, a steady-state ($\Phi\chi$) analysis was performed to identify sites of anaplerosis and exchange at intersecting metabolic nodes based on the quotient of product and precursor enrichments.

One or more metabolic pathways may contribute substrate to an enzymatic reaction. For instance Acetyl-CoA formation arises primarily from either pyruvate decarboxylation (PDH) or β-oxidation of fatty acids or some amino acids. The relative source of the carbons flowing into an enzymatic pathway can be determined if one of the pathways (e.g. pyruvate dehydrogenation or pyruvate carboxylation) can be selectively labeled. Differential equations can be defined to describe the rate of change of enrichment of a labeled metabolite of a substrate arising from a metabolic inflow minus the disappearance of the product. For the generalized reaction

where A is the initial substrate converted to product B by enzyme Ei and then B is converted to C by reaction E2, then the general equation is:

$$\frac{d[FE_{B*}]}{dt} = FE_{A*} * v_{E_1} - FE_{B*} * v_{E_2} \quad \text{(Eqn. 37)}$$

At metabolic and isotopic steady-state, the variation in 13 C-enrichment with time is zero by definition. Therefore the relative flux of $E_1$ with respect to E2 ($\Phi_{1\rightarrow 2}$) can be solved such that the relative contribution of the input relative to the output is equal to the enrichment of the product to its precursor:

$$\Phi_{1\rightarrow 2} = \frac{v_{E_1}}{v_{E_2}} = \frac{FE_{B*}}{FE_{A*}} \quad \text{(Eqn. 38)}$$

If $v_{E_1}$ is the only flux contributing to the generation of B, then no other pathway contributes to $FE_{B*}$ and $$\frac{v_{E_1}}{v_{E_2}}$$

will approach 1. So long as there are no additional metabolic inputs into the product B, then $E_1$ could describe multiple different reactions along the same pathway. Unfortunately, such a steady-state isotopic analysis can only determine whether or not there are significant net entry or exchange (balanced entry and exit) of an unlabeled metabolite between sequential or tandem metabolic reactions. Values less than 1 indicate unlabeled inputs from another source. For simplicity, we refer to the relative contribution of a substrate from a pathway A to its product pathway B as $\Phi_{AB}$ and $1-\Phi_{AB}$ equals the unlabeled input(s) to that pathway as shown below. It is worth noting that this analysis cannot distinguish anaplerotic from exchange reactions and is unable to identify cataplerotic loss of carbon as well.

PDH and PC reactions are the two main entry points of the $^{13}$C-label into the TCA cycle. At steady state, PDH and PC fluxes can be described relative to CS. Both of these relationships are shown in FIGS. 14A-14B.

In this analysis, the pools of OAA and malate were considered as one single pool due to the high exchange rate between OAA and malate relative to CS (Assumption 5 described above).

Figure 14A:
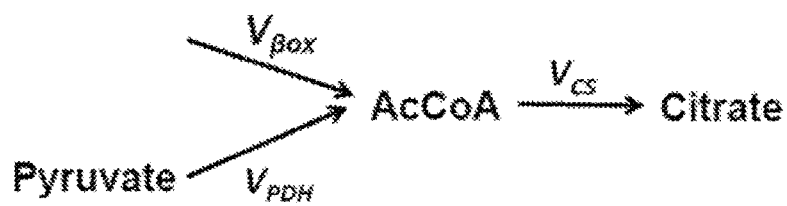
FIGS. 14A-14B illustrate metabolic schemes used to derive steady-state equations in an illustrative analysis, according to some embodiments.
Figure 14B:
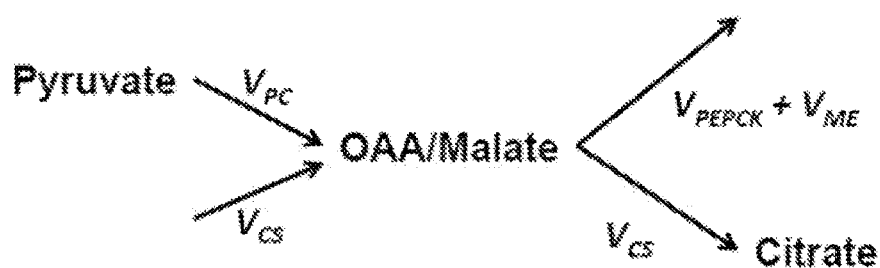
Figure 16B:
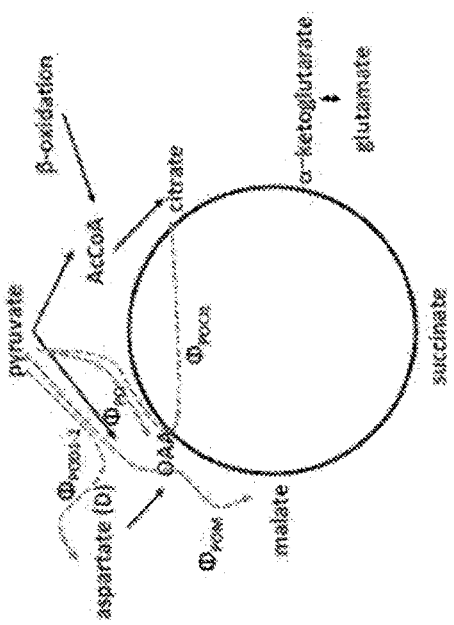
FIGS. 16A-16E are graphical representations of steady-state precursor-product relationships between metabolic intermediates involved in the PC, PDH and TCA cycle reactions in an illustrative analysis, according to some embodiments.
Figure 16C:
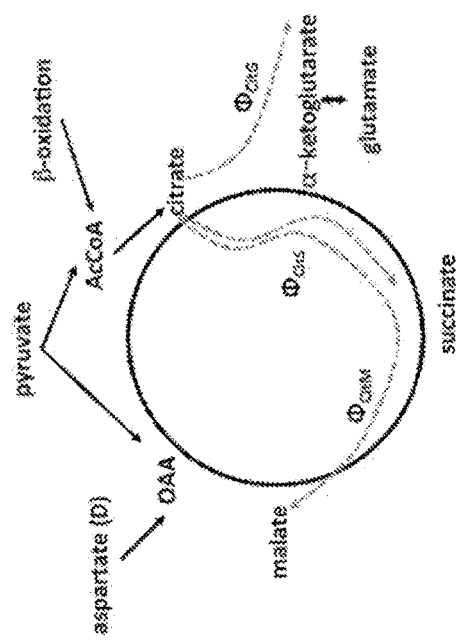
Figure 16A:
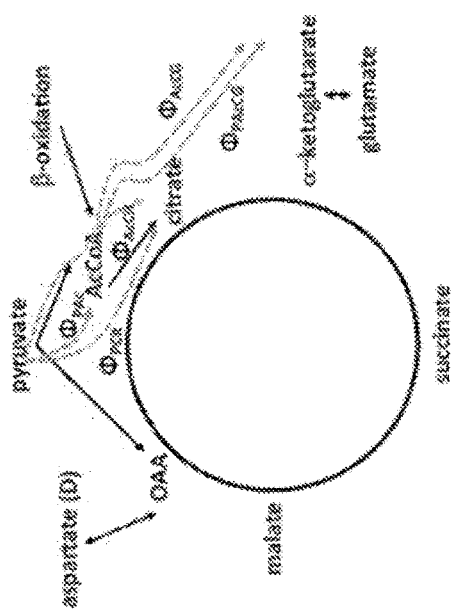
Figure 16E:
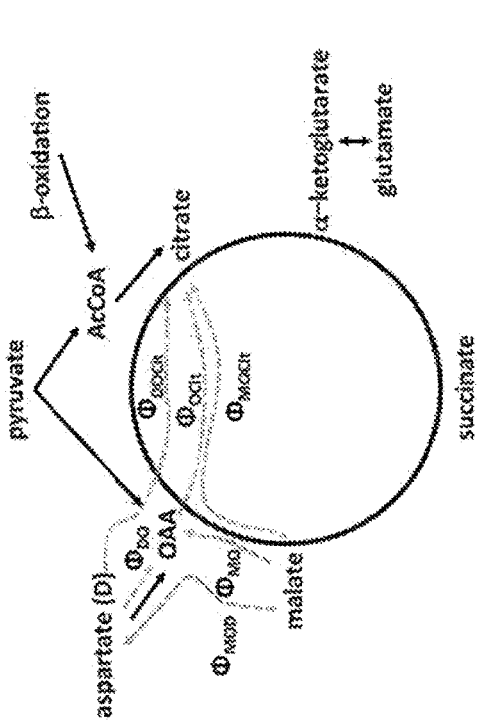
Figure 16D:
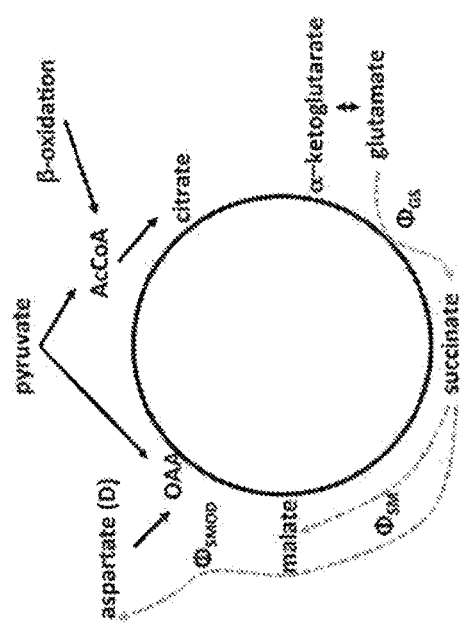

PDH converts [U-$^{13}$C$_3$]pyruvate into [1,2-$^{13}$C$_2$]acetyl-CoA which can, in turn, undergo further oxidation via the TCA cycle reactions (FIG. 14A). The variation of [1,2-$^{13}$C$_2$] acetyl-CoA with time as well as the mass balance relation are described by equations 39 and 40. As discussed above, [U-$^{13}$C$_3$]PEP may better represent the true enrichment of the glycolytic precursors. Therefore, [U-$^{13}$C$_3$]pyruvate has been replaced with [U-$^{13}$C$_3$]PEP enrichments in all equations that follow (including equation 39).

d[1,2-$^{13}$C$_2$]acetyl-CoA $$\frac{d[1,2-^{13}C_2]acetyl\text{-}CoA}{dt} = [U-^{13}C_3] \quad \text{(Eqn. 39)}$$
$$PEP * V_{PDH} - [1,2-^{13}C_2]AcCoA * V_{CS}$$

$$V_{PDH} + V_{\beta ox} = V_{CS} \quad \text{(Eqn. 40)}$$

At steady state, Eqn. 39 can be further simplified and solved for $V_{PDH}/V_{CS}$ to get the relative flux of PDH to CS ($\Phi_{PAc}$) (Eqn. 41). The enrichment in [1,2-$^{13}$C$_2$]AcCoA can be calculated as described in "Calculation of Acetyl-CoA Enrichments" while [U-$^{13}$C$_3$]PEP can be directly measured. Additionally, unlabeled input(s) coming from β-oxidation (or other unlabeled pathways) into mitochondrial acetyl-CoA ($V_{\beta ox}$, FIG. 14A) can also be calculated by taking Eqn. 40 into account (Eqn. 42).

$$\Phi_{PAc} = \frac{v_{PDH}}{V_{CS}} = \frac{[1,2-^{13}C_2]AcCoA}{[U-^{13}C_3]PEP} \quad \text{(Eqn. 41)}$$

$$\Phi_{\beta Ac} = \frac{v_{\beta ox}}{V_{CS}} = 1 - \Phi_{PAc} \quad \text{(Eqn. 42)}$$

PC is a mitochondrial enzyme that converts pyruvate into OAA (FIG. 14B). The relative rate of [(1,2,3)(2,3,4)-$^{13}$C$_3$] OAA synthesized from [U-$^{13}$C$_3$]pyruvate can be determined similarly to the described for PDH. In this case, OAA and malate are considered as one pool due to the rapid exchange relative to the TCA cycle flux (Assumption 5, Methods section). It follows that both PEPCK (phosphoenolpyruvate carboxykinase) and ME (malic enzyme) must be accounted for as reactions that consume [(1,2,3)(2,3,4)-$^{13}$C$_3$]OAA. It should also be noted that it is impossible to distinguish between OAA coming directly through PC flux from that coming indirectly via reverse 13 malic enzyme flux (pyruvate→malate). Both the variation of [(1,2,3)(2,3,4)-$^{13}$C$_3$] OAA with time as well as the mass balance relation is described by equations 43 and 44, respectively.

$$\frac{d[(1,2,3)(2,3,4)-^{13}C_3]OAA}{dt} = [U-^{13}C_3]PEP * \quad \text{(Eqn. 43)}$$
$$V_{PC} - [(1,2,3)(2,3,4)-^{13}C_3]OAA * (V_{CS} + V_{ME} + V_{PEPCK})$$

$$V_{CS} + V_{PC} = V_{CS} + V_{PEPCK} + V_{ME} \Rightarrow V_{PC} = V_{PEPCK} + V_{ME} \quad \text{(Eqn. 44)}$$

Equation 43 can be re-arranged when we take equation 44 into account (Eq. 45). At steady state, equation 45 can be further simplified and solved for $V_{PC}/V_{CS}$ to get the relative flux of PC to CS ($\Phi_{PO}$) (Eqn. 46).

$$\frac{d[(1,2,3)(2,3,4)-^{13}C_3]OAA}{dt} = [U-^{13}C_3] \quad \text{(Eqn. 45)}$$
$$PEP * V_{PC} - [(1,2,3)(2,3,4)-^{13}C_3]OAA *$$
$$V_{PC} - [(1,2,3)(2,3,4)-^{13}C_3]OAA * V_{CS}$$

$$\Phi_{PO} = \frac{V_{PC}}{V_{CS}} = \frac{[(1,2,3)(2,3,4)-^{13}C_3]OAA}{([U-^{13}C_3]PEP - [(1,2,3)(2,3,4)-^{13}C_3]OAA)} \quad \text{(Eqn. 46)}$$

In addition, $V_{PC}/V_{CS}$ can also be calculated using malate ($\Phi_{POM}$) and aspartate ($\Phi_{POD}$) as surrogate for the enrichments of OAA (Deconvolution of Citrate Isotopomers) (Eqns. 47-48).

$$\Phi_{POM} = \frac{[(1,2,3)(2,3,4)-{}^{13}C_3]\text{malate}}{([U-{}^{13}C_3]PEP - [(1,2,3)(2,3,4)-{}^{13}C_3]\text{malate})} \quad (\text{Eqn. 47})$$

$$\Phi_{POD} = \frac{[(1,2,3)(2,3,4)-{}^{13}C_3]\text{aspartate}}{([U-{}^{13}C_3]PEP - [(1,2,3)(2,3,4)-{}^{13}C_3]\text{aspartate})} \quad (\text{Eqn. 48})$$

PC and PDH fluxes share the same precursor (pyruvate) that react in the mitochondria to form a common product (citrate). The relative glycolytic contribution to the TCA cycle of PC vs. PDH ($\Phi_{PO}/\Phi_{PAc}$) can be determined from analysis of citrate isotopomers without the enrichment of pyruvate (the input function) since they are the same for both. Dividing the equations simplifies to eliminate the pyruvate enrichment (Eqn. 49).

$$\frac{\Phi_{PO}}{\Phi_{PAc}} = \quad (\text{Eqn. 49})$$

$$\frac{[(1,2,3)(2,3,4)-{}^{13}C_3]OAA}{[1,2-{}^{13}C_2]\text{acetyl-}CoA} \approx \frac{[(1,2,3)(2,3,4)-{}^{13}C_3]\text{malate}}{[1,2-{}^{13}C_2]\text{acetyl-}CoA} \approx$$

$$\frac{[(1,2,3)(2,3,4)-{}^{13}C_3]\text{aspartate}}{[1,2-{}^{13}C_2]\text{acetyl-}CoA}$$

As shown above, the citrate isotopomer family analysis measures the individual populations of isotopomers that contribute to both PC-derived OAA (families $\text{cit}_{c,h}$) and PDH-derived Acetyl CoA (families $\text{cit}_{a,d,f,h,i,j}$). Thus the relative PC/PDH flux can be determined by deconvolving the intramolecular isotopomeric labeling of citrate alone (Eqn. 50). These and other relationships are described in FIGS. 15A-15B.

$$\Phi_{PO}/\Phi_{PAc} = \frac{cit(c, h)}{cit(a, d, f, i, h, j)} \quad (\text{Eqn. 50})$$

Graphical representations of the results from FIGS. 15A-15B are illustrated in FIGS. 16A-16E. Some of the relationships described in FIGS. 15A-15B are equivalent, i.e., the ratio between precursor and product should be similar for different isotopomer groups if undergoing the same reaction. This is indicated by the numbered index following the flux description. For example, $\Phi_{CitG1-7}$, describe seven similar ways to characterize the flux from citrate to glutamate. However, because some of these isotopomer groups have low enrichment, the analysis is naturally prone to a certain degree of variability. For this reason, the relationship involving the highest enrichments, from within equivalent relationships, are marked with (*) in FIGS. 15A-15B and used as a reference.

e) Dynamic Modeling

The time courses of $^{13}C$ labeling were fit with a mathematical model of the TCA cycle describing the labeling of the pyruvate pool from a glycolytic precursor and the entry of carbons into the TCA cycle via the PDH and PC reactions using $[U-{}^{13}C_3]$-PEP as a driving function. The label is distributed through all possible isotopomers for citrate, aKG, glutamate, succinate, malate and OAA. The isotopomers were grouped in combination pools based on the number and/or position of labeled carbons and used to fit target data. As target data we used the following time course: $[U-{}^{13}C_3]$ pyruvate, $\text{Cit}_{a,f,i,d,h,j}$, $\text{Cit}_a$, $\text{Cit}_f$, $\text{Cit}_{h+i}$ and $\text{Cit}_j$, total label in glutamate-C4,5, and $^{13}C_2$—, $^{13}C_3$—, $^{13}C_4$-succinate, malate and OAA. The mass balance and isotope rate equations are shown below. The distributions of uncertainty were calculated using a Monte-Carlo analysis with 20 repetitions.

Figure 17:
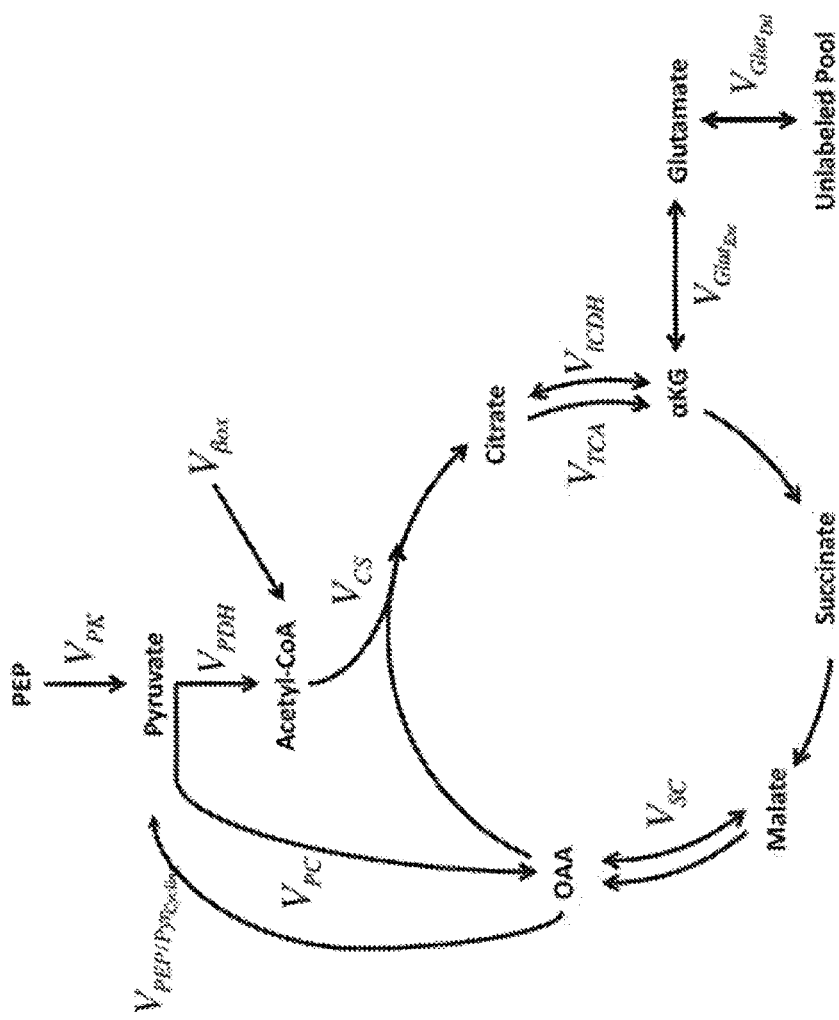
FIG. 17 is a schematic of reactions included in a mathematical model used to determine citrate synthase flux in an illustrative analysis, according to some embodiments.

FIG. 17 is a schematic of the reactions included in the mathematical model used to determine citrate synthase ($V_{cs}$) flux. Pyruvate kinase ($V_{PK}$) is the reaction responsible for the enrichment of the pyruvate pool. $^{13}C$-Label is then incorporated into the TCA cycle via pyruvate dehydrogenase ($V_{PDH}$) and pyruvate carboxylase ($V_{PC}$). PC flux is balanced by a rate converting oxaloacetate (OAA) into pyruvate ($V_{PEP/Pyr_{Cycling}}$). $V_{ICDH}$ is the exchange between the citrate/isocitrate and the α-ketoglutarate (αKG) pools, catalyzed by isocitrate dehydrogenase. $V_{Glut_{Exc}}$ refers to the exchange reaction between αKG and glutamate catalyzed by the aspartate transaminase. $v_{Glut_{Dil}}$ is the reaction responsible by the dilution of glutamate. $V_{sc}$ indicates the rate of exchange between the malate/fumarate pools and OAA responsible for the racemization of label.

Flux through citrate synthase ($V_{cs}$) was determined by fitting a one compartment metabolic model to the labeling time course of the TCA cycle intermediates (See FIG. 17). At metabolic steady state, anaplerosis is balanced by cataplerosis. Similarly, molecular exchange in equals exchange out. For the purpose of these measurements: 1) TCA flux is assumed to flow through CS, 2) PC flux must be balanced ($V_{PC}=V_{PEP/Pyr_{Cycling}}$) and 3) the entry of glutamate into the TCA cycle by transaminase exchange does not contribute to net TCA flux. The model depicted in See FIG. 17 was fitted to the $^{13}C$-label time courses.

The model used to calculate $V_{CS}$ is driven by the time course of $[U-{}^{13}C_3]$PEP and it starts with the conversion of PEP into pyruvate (See FIG. 17). In this model, pyruvate enters the TCA cycle via either the pyruvate dehydrogenase (PDH) or pyruvate carboxylase (PC) reactions. The pool of pyruvate is balanced by a cycling reaction, $V_{PEP/Pyr_{Cycling}}$ which converts OAA into pyruvate. Acetyl-CoA is synthesized directly by PDH. The dilution of the acetyl-CoA by oxidation of unlabeled lipid sources is described by $V_{\beta ox}$. $V_{\beta ox}$ was set as $(1-\Phi_{PAc})*V_{CS}$ (See FIGS. 15A-15B). Citrate is converted to aKG at a flux equal to $V_{CS}$. An additional exchange rate is defined between the aKG and the citrate ($V_{ICDH}$) pools to explain the label dilution between acetyl-CoA and citrate at steady state (See FIGS. 16A-16E).

Several factors were taken into account when choosing the addition of an exchange between citrate and aKG, as opposed to an exchange between citrate and an unlabeled source of carbons. While the only realistic source of dilution of the citrate pool is cytosolic citrate, at steady state, both pools, cytosolic and mitochondrial, are expected to have similar enrichments. Additionally, the quality of the fits of the $^{13}C$-citrate time course data is much improved with the addition $V_{ICDH}$. For instance, the analysis of the time course for labeled citrate originated from PDH ($\Sigma \text{Cit}_{a,f,i,d,h,j}$) at 9 mM glucose is better fit by multiexponential function and required an exchange between citrate and an unlabeled source. However, when $V_{ICDH}$ is included we obtain a more accurate description of the time course. Finally, the addition of $V_{ICDH}$ is in agreement with the physiology of the INS-1 cells where the possibility for reversed flux through isocitrate dehydrogenase (ICDH) has been considered.

At the level of αKG, $v_{Glut_{Exc}}$ describes the transaminase reaction between aKG and glutamate. In our model, $v_{Glut_{Exc}}$ was allowed to vary in order to settle in a value that corresponded to a complete exchange between the two pools. However, an upper limit was defined at $100*V_{CS}$. The limit of $100*V_{CS}$ simultaneously allows the model to find a rate that is not limiting relative to CS and reduces the amount of noise that comes from the search of a value of $v_{Glut_{Exc}}$ a several magnitudes higher than $V_{CS}$. The description of the glutamate enrichment data required the addition of a dilution rate. $v_{Glut_{Dil}}$ describes the dilution observed in the glutamate pool relative to the enrichments in citrate. This dilution can be explained by the presence of unlabeled glutamine in the experimental media. When unlabeled glutamine is absent from the experimental media the enrichments of citrate approach those of glutamate. Without $v_{Glut_{Dil}}$ the data cannot be fit (data not shown). Finally, $V_{SC}$ refers to the exchange between the OAA and malate/fumarate pools. The goal of this rate is to achieve the racemization of label expected from the equilibrium with fumarate. Therefore, $V_{SC}$ was allowed to vary with an upper limit of $100*V_{SC}$ similar to what was described for $v_{Glut_{Exc}}$.

The mass balance equations used to describe the variation of the concentration of the metabolites are as follows:

$$\frac{d[Pyruvate]}{dt} = V_{PEP/Pyr_{Cycling}} + V_{PE} - (V_{PC} + V_{PDH})$$

$$\frac{d[AcetylCoA]}{dt} = V_{PDH} + V_{\beta ox} - V_{CS}$$

$$\frac{d[Citrate]}{dt} = V_{CS} + V_{ICDH} - (V_{CS} + V_{ICDH})$$

$$\frac{d[\alpha KG]}{dt} = V_{CS} + V_{Glut_{Ext}} + V_{ICDH} - (V_{CS} + V_{Glut_{Exc}} + V_{ICDH})$$

$$\frac{d[Glutamate]}{dt} = V_{???} + V_{Glut_{Exc}} - (V_{Glut_{???}} + V_{Glut_{Exc}})$$

$$\frac{d[Succinate]}{dt} = V_{CS} - V_{CS}$$

$$\frac{d[Malate]}{dt} = V_{CS} + V_{SC} - (V_{CS} + V_{SC})$$

$$\frac{d[OAA]}{dt} = V_{CS} + V_{SC} + V_{PC} - \left(V_{CS} + V_{SC} + V_{PEP/Pyr_{Cycling}}\right)$$

$$V_{PK} = V_{PDH}$$

$$V_{PEP/Pyr_{Cycling}} = V_{PC}$$

$$V_{CS} = V_{PDH} + V_{\beta ox} = V_{TCA}$$

$$V_{\beta ox} = (1 - \Phi_{PAc}) * V_{CS}$$

Figure 18:
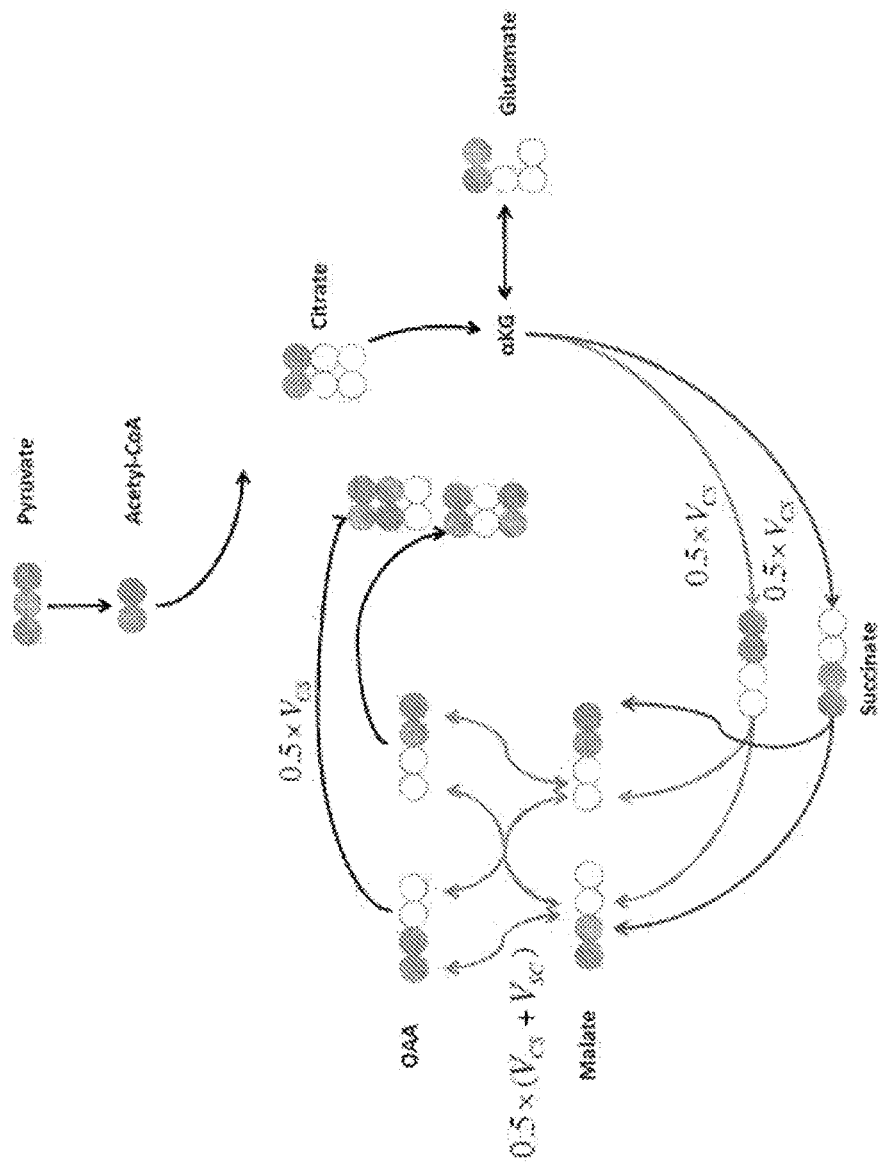
FIG. 18 depicts label flow within the TCA cycle in an illustrative analysis, according to some embodiments.

A depiction of the label flow within the TCA cycle is shown in FIG. 18. Essentially, all the carbon positions are maintained during the mass transfer from citrate to glutamate. An exception is carbon 6 of citrate, which is lost during the first decarboxylation occurring in the TCA cycle. Thus, [4,5-$^{13}C_2$]citrate, for instance, originates [4,5-$^{13}C_2$] glutamate (Figure D-1B). In the transition from glutamate to succinate, the molecular symmetry of succinate must be taken into account. Because of this symmetry, [4,5-$^{13}C_2$] glutamate originates equal amounts of [1,2-$^{13}C_2$] and [3,4-$^{13}C_2$] succinate, each formed at rate that is ½ of the TCA cycle flux. A similar concept was used to described the racemization of the label between the OAA, malate and fumarate pools. This racemization occurs because of the near-equilibrium reactions connecting the OAA and malate pools with fumarate, also a symmetrical molecule. Fumarate was not included in this model. Instead, we assumed that racemization occurred in the malate pool. Thus, [1,2-$^{13}C_2$] malate originates [1,2-$^{13}C_2$] and [3,4-$^{13}C_2$]OAA at a rate that is ½ of ($V_{CS}$+$V_{SC}$).

In an illustrative analysis, the isotopic balance equations used to describe the $^{13}$C-label flow between all possible isotopomers of the considered metabolites may be as follows:

Pyruvate
  dPyruvate_123/dt=PK(PEP_123/PEP)+PEP/Pyr_cycling (OAA_123/OAA)+PEP/Pyr_cycling(OAA_1234/OAA)−(PDH+PC)(Pyruvate_123/Pyruvate)
  dPyruvate_12/dt=PEP/Pyr_cycling(OAA_124/OAA)+PEP/Pyr_cycling(OAA_12/OAA)+PDH(NA_0/NA)−(PDH+PC)(Pyruvate_12/Pyruvate)
  dPyruvate_23/dt=PEP/Pyr_cycling(OAA_23/OAA)+PEP/Pyr_cycling(OAA_234/OAA)+PDH(NA_0/NA)−(PDH+PC)(Pyruvate_23/Pyruvate)
  dPyruvate_13/dt=PEP/Pyr_cycling(OAA_13/OAA)+PEP/Pyr_cycling(OAA_134/OAA)+PDH(NA_0/NA)−(PDH+PC)(Pyruvate_13/Pyruvate)
  dPyruvate_1/dt=PEP/Pyr_cycling(OAA_1/OAA)+PEP/Pyr_cycling(OAA_4/OAA)+PDH(NA_0/NA)−(PDH+PC)(Pyruvate_1/Pyruvate)
  dPyruvate_2/dt=PEP/Pyr_cycling(OAA_2/OAA)+PEP/Pyr_cycling(OAA_24/OAA)+PDH(NA_0/NA)−(PDH+PC)(Pyruvate_2/Pyruvate)
  dPyruvate_3/dt=PEP/Pyr_cycling(OAA_3/OAA)+PEP/Pyr_cycling(OAA_34/OAA)+PDH(NA_0/NA)−(PDH+PC)(Pyruvate_3/Pyruvate)

Acetyl-CoA
  dAcetylCoA_12/dt=PDH(Pyruvate_123/Pyruvate)+PDH(Pyruvate_23/Pyruvate)+Beta_ox(NA_0/NA)−CS(AcetylCoA_12/AcetylCoA)
  dAcetylCoA_1/dt=PDH(Pyruvate_12/Pyruvate)+PDH(Pyruvate_2/Pyruvate)+Beta_ox(NA_0/NA)−CS(AcetylCoA_1/AcetylCoA)
  dAcetylCoA_2/dt=PDH(Pyruvate_13/Pyruvate)+PDH(Pyruvate_3/Pyruvate)+Beta_ox(NA_0/NA)−CS(AcetylCoA_2/AcetylCoA)

Citrate
  dCitrate_1/dt=CS(AcetylCoA_0/AcetylCoA)(OAA_1/OAA)+ICDH(aKG_1/aKG)−(CS+ICDH)(Citrate_1/Citrate)
  dCitrate_2/dt=CS(OAA_2/OAA)(AcetylCoA_0/AcetylCoA)+ICDH(aKG_2/aKG)−(CS+ICDH)(Citrate_2/Citrate)
  dCitrate_3/dt=CS(OAA_3/OAA)(AcetylCoA_0/AcetylCoA)+ICDH(aKG_3/aKG)−(CS+ICDH)(Citrate_3/Citrate)
  dCitrate_4/dt=CS(AcetylCoA_2/AcetylCoA)(OAA_0/OAA)+ICDH(aKG_4/aKG)−(CS+ICDH)(Citrate_4/Citrate)
  dCitrate_5/dt=CS(AcetylCoA_1/AcetylCoA)(OAA_0/OAA)+ICDH(aKG_5/aKG)−(CS+ICDH)(Citrate_5/Citrate)
  dCitrate_6/dt=CS(OAA_4/OAA)(OAA_0/OAA)+ICDH(NA_0/NA)−(CS+ICDH)(Citrate_6/Citrate)
  dCitrate_12/dt=CS(OAA_12/OAA)(OAA_0/OAA)+ICDH(aKG_12/aKG)−(CS+ICDH)(Citrate_12/Citrate)
  dCitrate_13/dt=CS(OAA_13/OAA)(AcetylCoA_0/AcetylCoA)+ICDH(aKG_13/aKG)−(CS+ICDH)(Citrate_13/Citrate)
  dCitrate_14/dt=CS(AcetylCoA_2/AcetylCoA)(OAA_1/OAA)+ICDH(aKG_14/aKG)−(CS+ICDH)(Citrate_14/Citrate)
  dCitrate_15/dt=CS(AcetylCoA_1/AcetylCoA)(OAA_1/OAA)+ICDH(aKG_15/aKG)−(CS+ICDH)(Citrate_15/Citrate)

dCitrate_16/dt=CS(OAA_14/OAA)(AcetylCoA_0/AcetylCoA)+ICDH(NA_0/NA)−(CS+ICDH)(Citrate_16/Citrate)

dCitrate_23/dt=CS(OAA_23/OAA)(AcetylCoA_0/AcetylCoA)+ICDH(aKG_23/aKG)−(CS+ICDH)(Citrate_23/Citrate)

dCitrate_24/dt=CS(OAA_2/OAA)(AcetylCoA_2/AcetylCoA)+ICDH(aKG_24/aKG)−(CS+ICDH)(Citrate_24/Citrate)

dCitrate_25/dt=CS(OAA_2/OAA)(AcetylCoA_1/AcetylCoA)+ICDH(aKG_25/aKG)−(CS+ICDH)(Citrate_25/Citrate)

dCitrate_26/dt=CS(OAA_24/OAA)(AcetylCoA_0/AcetylCoA)+ICDH(NA_0/NA)−(CS+ICDH)(Citrate_26/Citrate)

dCitrate_34/dt=CS(OAA_3/OAA)(AcetylCoA_2/AcetylCoA)+ICDH(aKG_34/aKG)−(CS+ICDH)(Citrate_34/Citrate)

dCitrate_35/dt=CS(OAA_3/OAA)(AcetylCoA_1/AcetylCoA)+ICDH(aKG_35/aKG)−(CS+ICDH)(Citrate_35/Citrate)

dCitrate_36/dt=CS(OAA_34/OAA)(AcetylCoA_0/AcetylCoA)+ICDH(NA_0/NA)−(CS+ICDH)(Citrate_36/Citrate)

dCitrate_45/dt=CS(AcetylCoA_12/AcetylCoA)(OAA_0/OAA)+ICDH(aKG 45/aKG)−(CS+ICDH)(Citrate_45/Citrate)

dCitrate_46/dt=CS(AcetylCoA_2/AcetylCoA)(OAA_4/OAA)+ICDH(NA_0/NA)−(CS+ICDH)(Citrate_46/Citrate)

dCitrate_56/dt=CS(AcetylCoA_1/AcetylCoA)(OAA_4/OAA)+ICDH(NA_0/NA)−(CS+ICDH)(Citrate_56/Citrate)

dCitrate_123/dt=CS(OAA_123/OAA)(AcetylCoA_0/AcetylCoA)+ICDH(aKG_123/aKG)−(CS+ICDH)(Citrate_123/Citrate)

dCitrate_124/dt=CS(AcetylCoA_2/AcetylCoA)(OAA_12/OAA)+ICDH(aKG_124/aKG)−(CS+ICDH)(Citrate_124/Citrate)

dCitrate_125/dt=CS(AcetylCoA_1/AcetylCoA)(OAA_12/OAA)+ICDH(aKG_125/aKG)−(CS+ICDH)(Citrate_125/Citrate)

dCitrate_126/dt=CS(OAA_124/OAA)(AcetylCoA_0/AcetylCoA)+ICDH(NA_0/NA)−(CS+ICDH)(Citrate_126/Citrate)

dCitrate_134/dt=CS(AcetylCoA_2/AcetylCoA)(OAA_13/OAA)+ICDH(aKG_134/aKG)−(CS+ICDH)(Citrate_134/Citrate)

dCitrate_135/dt=CS(AcetylCoA_1/AcetylCoA)(OAA_13/OAA)+ICDH(aKG_135/aKG)−(CS+ICDH)(Citrate_135/Citrate)

dCitrate_136/dt=CS(OAA_134/OAA)(AcetylCoA_0/AcetylCoA)+ICDH(NA_0/NA)−(CS+ICDH)(Citrate_136/Citrate)

dCitrate_145/dt=CS(AcetylCoA_12/AcetylCoA)(OAA_1/OAA)+ICDH(aKG_145/aKG)−(CS+ICDH)(Citrate_145/Citrate)

dCitrate_146/dt=CS(AcetylCoA_2/AcetylCoA)(OAA_14/OAA)+ICDH(NA_0/NA)−(CS+ICDH)(Citrate_146/Citrate)

dCitrate_156/dt=CS(AcetylCoA_1/AcetylCoA)(OAA_14/OAA)+ICDH(NA_0/NA)−(CS+ICDH)(Citrate_156/Citrate)

dCitrate_234/dt=CS(AcetylCoA_2/AcetylCoA)(OAA_23/OAA)+ICDH(aKG_234/aKG)−(CS+ICDH)(Citrate_234/Citrate)

dCitrate_235/dt=CS(AcetylCoA_1/AcetylCoA)(OAA_23/OAA)+ICDH(aKG_235/aKG)−(CS+ICDH)(Citrate_235/Citrate)

dCitrate_236/dt=CS(OAA_234/OAA)(AcetylCoA_0/AcetylCoA)+ICDH(NA_0/NA)−(CS+ICDH)(Citrate_236/Citrate)

dCitrate_245/dt=CS(AcetylCoA_12/AcetylCoA)(OAA_2/OAA)+ICDH(aKG_245/aKG)−(CS+ICDH)(Citrate_245/Citrate)

dCitrate_246/dt=CS(AcetylCoA_2/AcetylCoA)(OAA_24/OAA)+ICDH(NA_0/NA)−(CS+ICDH)(Citrate_246/Citrate)

dCitrate_256/dt=CS(AcetylCoA_1/AcetylCoA)(OAA_24/OAA)+ICDH(NA_0/NA)−(CS+ICDH)(Citrate_256/Citrate)

dCitrate_345/dt=CS(AcetylCoA_12/AcetylCoA)(OAA_3/OAA)+ICDH(aKG_345/aKG)−(CS+ICDH)(Citrate_345/Citrate)

dCitrate_346/dt=CS(AcetylCoA_2/AcetylCoA)(OAA_34/OAA)+ICDH(NA_0/NA)−(CS+ICDH)(Citrate_346/Citrate)

dCitrate_356/dt=CS(AcetylCoA_1/AcetylCoA)(OAA_34/OAA)+ICDH(NA_0/NA)−(CS+ICDH)(Citrate_356/Citrate)

dCitrate_456/dt=CS(AcetylCoA_12/AcetylCoA)(OAA_4/OAA)+ICDH(NA_0/NA)−(CS+ICDH)(Citrate_456/Citrate)

dCitrate_1234/dt=CS(AcetylCoA_2/AcetylCoA)(OAA_123/OAA)+ICDH(aKG_1234/aKG)−(CS+ICDH)(Citrate_1234/Citrate)

dCitrate_1235/dt=CS(AcetylCoA_1/AcetylCoA)(OAA_123/OAA)+ICDH(aKG_1235/aKG)−(CS+ICDH)(Citrate_1235/Citrate)

dCitrate_1236/dt=CS(OAA_1234/OAA)(AcetylCoA_0/AcetylCoA)+ICDH(NA_0/NA)−(CS+ICDH)(Citrate_1236/Citrate)

dCitrate_1245/dt=CS(AcetylCoA_12/AcetylCoA)(OAA_12/OAA)+ICDH(aKG_1245/aKG)−(CS+ICDH)(Citrate_1245/Citrate)

dCitrate_1246/dt=CS(AcetylCoA_2/AcetylCoA)(OAA_124/OAA)+ICDH(NA_0/NA)−(CS+ICDH)(Citrate_1246/Citrate)

dCitrate_1256/dt=CS(AcetylCoA_1/AcetylCoA)(OAA_124/OAA)+ICDH(NA_0/NA)−(CS+ICDH)(Citrate_1256/Citrate)

dCitrate_1345/dt=CS(AcetylCoA_12/AcetylCoA)(OAA_13/OAA)+ICDH(aKG_1345/aKG)−(CS+ICDH)(Citrate_1345/Citrate)

dCitrate_1346/dt=CS(AcetylCoA_2/AcetylCoA)(OAA_134/OAA)+ICDH(NA_0/NA)−(CS+ICDH)(Citrate_1346/Citrate)

dCitrate_1356/dt=CS(AcetylCoA_1/AcetylCoA)(OAA_134/OAA)+ICDH(NA_0/NA)−(CS+ICDH)(Citrate_1356/Citrate)

dCitrate_1456/dt=CS(AcetylCoA_12/AcetylCoA)(OAA_14/OAA)+ICDH(NA_0/NA)−(CS+ICDH)(Citrate_1456/Citrate)

dCitrate_2345/dt=CS(AcetylCoA_12/AcetylCoA)(OAA_23/OAA)+ICDH(aKG_2345/aKG)−(CS+ICDH)(Citrate_2345/Citrate)

dCitrate_2346/dt=CS(AcetylCoA_2/AcetylCoA)(OAA_234/OAA)+ICDH(NA_0/NA)−(CS+ICDH)(Citrate_2346/Citrate)

dCitrate_2356/dt=CS(AcetylCoA_1/AcetylCoA)(OAA_234/OAA)+ICDH(NA_0/NA)−(CS+ICDH)(Citrate_2356/Citrate)

dCitrate_2456/dt=CS(AcetylCoA_12/AcetylCoA)(OAA_24/OAA)+ICDH(NA_0/NA)−(CS+ICDH)(Citrate_2456/Citrate)

dCitrate_3456/dt=CS(AcetylCoA_12/AcetylCoA)(OAA_34/OAA)+ICDH(NA_0/NA)−(CS+ICDH)(Citrate_3456/Citrate)

dCitrate_12345/dt=CS(AcetylCoA_12/AcetylCoA)(OAA_123/OAA)+ICDH(aKG_12345/aKG)−(CS+ICDH)(Citrate_12345/Citrate)

dCitrate_12346/dt=CS(AcetylCoA_2/AcetylCoA)(OAA_1234/OAA)+ICDH(NA_0/NA)−(CS+ICDH)(Citrate_12346/Citrate)

dCitrate_12356/dt=CS(AcetylCoA_1/AcetylCoA)(OAA_1234/OAA)+ICDH(NA_0/NA)−(CS+ICDH)(Citrate_12356/Citrate)

dCitrate_12456/dt=CS(AcetylCoA_12/AcetylCoA)(OAA_124/OAA)+ICDH(NA_0/NA)−(CS+ICDH)(Citrate_12456/Citrate)

dCitrate_13456/dt=CS(AcetylCoA_12/AcetylCoA)(OAA_134/OAA)+ICDH(NA_0/NA)−(CS+ICDH)(Citrate_13456/Citrate)

dCitrate_23456/dt=CS(AcetylCoA_12/AcetylCoA)(OAA_234/OAA)+ICDH(NA_0/NA)−(CS+ICDH)(Citrate_23456/Citrate)

dCitrate_123456/dt=CS(AcetylCoA_12/AcetylCoA)(OAA_1234/OAA)+ICDH(NA_0/NA)−(CS+ICDH)(Citrate_123456/Citrate)

aKG daKG_1/dt=CS(Citrate_1/Citrate)+CS(Citrate_16/Citrate)+Glut_exc(Glutamate_1/Glutamate)+ICDH(Citrate_1/Citrate)+ICDH(Citrate_16/Citrate)−(CS+Glut_exc+ICDH)(aKG_1/aKG)

daKG_2/dt=CS(Citrate_2/Citrate)+CS(Citrate_26/Citrate)+Glut_exc(Glutamate_2/Glutamate)+ICDH(Citrate_2/Citrate)+ICDH(Citrate_26/Citrate)−(CS+Glut_exc+ICDH)(aKG_2/aKG)

daKG_3/dt=CS(Citrate_3/Citrate)+CS(Citrate_36/Citrate)+Glut_exc(Glutamate_2/Glutamate)+ICDH(Citrate_3/Citrate)+ICDH(Citrate_36/Citrate)−(CS+Glut_exc+ICDH)(aKG_3/aKG)

daKG_4/dt=CS(Citrate_4/Citrate)+CS(Citrate_46/Citrate)+Glut_exc(Glutamate_4/Glutamate)+ICDH(Citrate_4/Citrate)+ICDH(Citrate_46/Citrate)−(CS+Glut_exc+ICDH)(aKG_4/aKG)

daKG_5/dt=CS(Citrate_5/Citrate)+CS(Citrate_56/Citrate)+Glut_exc(Glutamate_5/Glutamate)+ICDH(Citrate_5/Citrate)+ICDH(Citrate_56/Citrate)−(CS+Glut_exc+ICDH)(aKG_5/aKG)

daKG_12/dt=CS(Citrate_12/Citrate)+CS(Citrate_126/Citrate)+Glut_exc(Glutamate_12/Glutamate)+ICDH(Citrate_126/Citrate)+ICDH(Citrate_12/Citrate)−(CS+Glut_exc+ICDH)(aKG_12/aKG)

daKG_13/dt=CS(Citrate_13/Citrate)+CS(Citrate_136/Citrate)+Glut_exc(Glutamate_13/Glutamate)+ICDH(Citrate_13/Citrate)+ICDH(Citrate_136/Citrate)−(CS+Glut_exc+ICDH)(aKG_13/aKG)

daKG_14/dt=CS(Citrate_14/Citrate)+CS(Citrate_146/Citrate)+Glut_exc(Glutamate_14/Glutamate)+ICDH(Citrate_14/Citrate)+ICDH(Citrate_146/Citrate)−(CS+Glut_exc+ICDH)(aKG_14/aKG)

daKG_15/dt=CS(Citrate_15/Citrate)+CS(Citrate_156/Citrate)+Glut_exc(Glutamate_15/Glutamate)+ICDH(Citrate_15/Citrate)+ICDH(Citrate_156/Citrate)−(CS+Glut_exc+ICDH)(aKG_15/aKG)

daKG_23/dt=CS(Citrate_23/Citrate)+CS(Citrate_236/Citrate)+Glut_exc(Glutamate_23/Glutamate)+ICDH(Citrate_23/Citrate)+ICDH(Citrate_236/Citrate)−(CS+Glut_exc+ICDH)(aKG_23/aKG)

daKG_24/dt=CS(Citrate_24/Citrate)+CS(Citrate_246/Citrate)+Glut_exc(Glutamate_24/Glutamate)+ICDH(Citrate_24/Citrate)+ICDH(Citrate_246/Citrate)−(CS+Glut_exc+ICDH)(aKG_24/aKG)

daKG_25/dt=CS(Citrate_25/Citrate)+CS(Citrate_256/Citrate)+Glut_exc(Glutamate_25/Glutamate)+ICDH(Citrate_25/Citrate)+ICDH(Citrate_256/Citrate)−(CS+Glut_exc+ICDH)(aKG_25/aKG)

daKG_34/dt=CS(Citrate_34/Citrate)+CS(Citrate_346/Citrate)+Glut_exc(Glutamate_34/Glutamate)+ICDH(Citrate_34/Citrate)+ICDH(Citrate_346/Citrate)−(CS+Glut_exc+ICDH)(aKG_34/aKG)

daKG_35/dt=CS(Citrate_35/Citrate)+CS(Citrate_356/Citrate)+Glut_exc(Glutamate_35/Glutamate)+ICDH(Citrate_35/Citrate)+ICDH(Citrate_356/Citrate)−(CS+Glut_exc+ICDH)(aKG_35/aKG)

daKG_45/dt=CS(Citrate_45/Citrate)+CS(Citrate_456/Citrate)+Glut_exc(Glutamate_45/Glutamate)+ICDH(Citrate_45/Citrate)+ICDH(Citrate_456/Citrate)−(CS+Glut_exc+ICDH)(aKG 45/aKG)

daKG_123/dt=CS(Citrate_123/Citrate)+CS(Citrate_1236/Citrate) Glut_exc(Glutamate_123/Glutamate)+ICDH(Citrate_123/Citrate)+ICDH(Citrate_1236/Citrate)−(CS+Glut_exc+ICDH)(aKG_123/aKG)

daKG_124/dt=CS(Citrate_124/Citrate)+CS(Citrate_1246/Citrate) Glut_exc(Glutamate_124/Glutamate)+ICDH(Citrate_124/Citrate)+ICDH(Citrate_1246/Citrate)−(CS+Glut_exc+ICDH)(aKG_124/aKG)

daKG_125/dt=CS(Citrate_125/Citrate)+CS(Citrate_1256/Citrate) Glut_exc(Glutamate_125/Glutamate)+ICDH(Citrate_125/Citrate)+ICDH(Citrate_1256/Citrate)−(CS+Glut_exc+ICDH)(aKG_125/aKG)

daKG_134/dt=CS(Citrate_134/Citrate)+CS(Citrate_1346/Citrate) Glut_exc(Glutamate_134/Glutamate)+ICDH(Citrate_134/Citrate)+ICDH(Citrate_1346/Citrate)−(CS+Glut_exc+ICDH)(aKG_134/aKG)

daKG_135/dt=CS(Citrate_135/Citrate)+CS(Citrate_1356/Citrate) Glut_exc(Glutamate_135/Glutamate)+ICDH(Citrate_135/Citrate)+ICDH(Citrate_1356/Citrate)−(CS+Glut_exc+ICDH)(aKG_135/aKG)

daKG_145/dt=CS(Citrate_145/Citrate)+CS(Citrate_1456/Citrate) Glut_exc(Glutamate_145/Glutamate)+ICDH(Citrate_145/Citrate)+ICDH(Citrate_1456/Citrate)−(CS+Glut_exc+ICDH)(aKG_145/aKG)

daKG_234/dt=CS(Citrate_234/Citrate)+CS(Citrate_2346/Citrate)+Glut_exc(Glutamate_234/Glutamate)+ICDH(Citrate_234/Citrate)+ICDH(Citrate_2346/Citrate)−(CS+Glut_exc+ICDH)(aKG_234/aKG)

daKG_235/dt=CS(Citrate_235/Citrate)+CS(Citrate_2356/Citrate)+Glut_exc(Glutamate_235/Glutamate)+ICDH(Citrate_235/Citrate)+ICDH(Citrate_2356/Citrate)−(CS+Glut_exc+ICDH)(aKG_235/aKG)

daKG_245/dt=CS(Citrate_245/Citrate)+CS(Citrate_2456/Citrate)+Glut_exc(Glutamate_245/Glutamate)+ICDH(Citrate_245/Citrate)+ICDH(Citrate_2456/Citrate)−(CS+Glut_exc+ICDH)(aKG_245/aKG)

daKG_345/dt=CS(Citrate_345/Citrate)+CS(Citrate_3456/Citrate)+Glut_exc(Glutamate_3456/Glutamate)+ICDH(Citrate_345/Citrate)+ICDH(Citrate_3456/Citrate)−(CS+Glut_exc+ICDH)(aKG_345/aKG)

daKG_1234/dt=CS(Citrate_1234/Citrate)+CS(Citrate_12346/Citrate)+Glut_exc(Glutamate_1234/Glutamate)+ICDH(Citrate_1234/Citrate)+ICDH(Citrate_12346/Citrate)−(CS+Glut_exc+ICDH)(aKG_1234/aKG)

daKG_1235/dt=CS(Citrate_1235/Citrate)+CS(Citrate_12356/Citrate)+Glut_exc(Glutamate_1235/Glutamate)+ICDH(Citrate_1235/Citrate)+ICDH(Citrate_12356/Citrate)−(CS+Glut_exc+ICDH)(aKG_1235/aKG)

daKG_1245/dt=CS(Citrate_1245/Citrate)+CS(Citrate_12456/Citrate)+Glut_exc(Glutamate_1245/Glutamate)+ICDH(Citrate_1245/Citrate)+ICDH(Citrate_12456/Citrate)−(CS+Glut_exc+ICDH)(aKG_1245/aKG)

daKG_1345/dt=CS(Citrate_1345/Citrate)+CS(Citrate_13456/Citrate)+Glut_exc(Glutamate_1345/Glutamate)+ICDH(Citrate_1345/Citrate)+ICDH(Citrate_13456/Citrate)−(CS+Glut_exc+ICDH)(aKG_1345/aKG)

daKG_2345/dt=CS(Citrate_2345/Citrate)+CS(Citrate_23456/Citrate)+Glut_exc(Glutamate_2345/Glutamate)+ICDH(Citrate_2345/Citrate)+ICDH(Citrate_23456/Citrate)−(CS+Glut_exc+ICDH)(aKG_2345/aKG)

daKG_12345/dt=CS(Citrate_12345/Citrate)+CS(Citrate_123456/Citrate)+Glut_exc(Glutamate_12345/Glutamate)+ICDH(Citrate_12345/Citrate)+ICDH(Citrate_123456/Citrate)−(CS+Glut_exc+ICDH)(aKG_12345/aKG)

Glutamate dGlutamate_1/dt=Glut_dil(NA_0/NA)+Glut_exc(aKG_1/aKG)−(Glut_dil+Glut_exc)(Glutamate_1/Glutamate)

dGlutamate_2/dt=Glut_dil(NA_0/NA)+Glut_exc(aKG_2/aKG)−(Glut_dil+Glut_exc)(Glutamate_2/Glutamate)

dGlutamate_3/dt=Glut_dil(NA_0/NA)+Glut_exc(aKG_3/aKG)−(Glut_dil+Glut_exc)(Glutamate_3/Glutamate)

dGlutamate_4/dt=Glut_dil(NA_0/NA)+Glut_exc(aKG_4/aKG)−(Glut_dil+Glut_exc)(Glutamate_4/Glutamate)

dGlutamate_5/dt=Glut_dil(NA_0/NA)+Glut_exc(aKG_5/aKG)−(Glut_dil+Glut_exc)(Glutamate_5/Glutamate)

dGlutamate_12/dt=Glut_dil(NA_0/NA)+Glut_exc(aKG_12/aKG)−(Glut_dil+Glut_exc)(Glutamate_12/Glutamate)

dGlutamate_13/dt=Glut_dil(NA_0/NA)+Glut_exc(aKG_13/aKG)−(Glut_dil+Glut_exc)(Glutamate_13/Glutamate)

dGlutamate_14/dt=Glut_dil(NA_0/NA)+Glut_exc(aKG_14/aKG)−(Glut_dil+Glut_exc)(Glutamate_14/Glutamate)

dGlutamate_15/dt=Glut_dil(NA_0/NA)+Glut_exc(aKG_15/aKG)−(Glut_dil+Glut_exc)(Glutamate_15/Glutamate)

dGlutamate_23/dt=Glut_dil(NA_0/NA)+Glut_exc(aKG_23/aKG)−(Glut_dil+Glut_exc)(Glutamate_23/Glutamate)

dGlutamate_24/dt=Glut_dil(NA_0/NA)+Glut_exc(aKG_24/aKG)−(Glut_dil+Glut_exc)(Glutamate_24/Glutamate)

dGlutamate_25/dt=Glut_dil(NA_0/NA)+Glut_exc(aKG_25/aKG)−(Glut_dil+Glut_exc)(Glutamate_25/Glutamate)

dGlutamate_34/dt=Glut_dil(NA_0/NA)+Glut_exc(aKG_34/aKG)−(Glut_dil+Glut_exc)(Glutamate_34/Glutamate)

dGlutamate_35/dt=Glut_dil(NA_0/NA)+Glut_exc(aKG_35/aKG)−(Glut_dil+Glut_exc)(Glutamate_35/Glutamate)

dGlutamate_45/dt=Glut_dil(NA_0/NA)+Glut_exc(aKG_45/aKG)−(Glut_dil+Glut_exc)(Glutamate_45/Glutamate)

dGlutamate_123/dt=Glut_dil(NA_0/NA)+Glut_exc(aKG_123/aKG)−(Glut_dil+Glut_exc)(Glutamate_123/Glutamate)

dGlutamate_124/dt=Glut_dil(NA_0/NA)+Glut_exc(aKG_124/aKG)−(Glut_dil+Glut_exc)(Glutamate_124/Glutamate)

dGlutamate_125/dt=Glut_dil(NA_0/NA)+Glut_exc(aKG_125/aKG)−(Glut_dil+Glut_exc)(Glutamate_125/Glutamate)

dGlutamate_134/dt=Glut_dil(NA_0/NA)+Glut_exc(aKG_134/aKG)−(Glut_dil+Glut_exc)(Glutamate_134/Glutamate)

dGlutamate_135/dt=Glut_dil(NA_0/NA)+Glut_exc(aKG_135/aKG)−(Glut_dil+Glut_exc)(Glutamate_135/Glutamate)

dGlutamate_145/dt=Glut_dil(NA_0/NA)+Glut_exc(aKG_145/aKG)−(Glut_dil+Glut_exc)(Glutamate_145/Glutamate)

dGlutamate_234/dt=Glut_dil(NA_0/NA)+Glut_exc(aKG_234/aKG)−(Glut_dil+Glut_exc)(Glutamate_234/Glutamate)

dGlutamate_235/dt=Glut_dil(NA_0/NA)+Glut_exc(aKG_235/aKG)−(Glut_dil+Glut_exc)(Glutamate_235/Glutamate)

dGlutamate_245/dt=Glut_dil(NA_0/NA)+Glut_exc(aKG_245/aKG)−(Glut_dil+Glut_exc)(Glutamate_245/Glutamate)

dGlutamate_345/dt=Glut_dil(NA_0/NA)+Glut_exc(aKG_345/aKG)−(Glut_dil+Glut_exc)(Glutamate_345/Glutamate)

dGlutamate_1234/dt=Glut_dil(NA_0/NA)+Glut_exc(aKG_1234/aKG)−(Glut_dil+Glut_exc)(Glutamate_1234/Glutamate)

dGlutamate_1235/dt=Glut_dil(NA_0/NA)+Glut_exc(aKG_1235/aKG)−(Glut_dil+Glut_exc)(Glutamate_1235/Glutamate)

dGlutamate_1245/dt=Glut_dil(NA_0/NA)+Glut_exc(aKG_1245/aKG)−(Glut_dil+Glut_exc)(Glutamate_1245/Glutamate)

dGlutamate_1345/dt=Glut_dil(NA_0/NA)+Glut_exc(aKG_1345/aKG)−(Glut_dil+Glut_exc)(Glutamate_1345/Glutamate)

dGlutamate_2345/dt=Glut_dil(NA_0/NA)+Glut_exc(aKG_2345/aKG)−(Glut_dil+Glut_exc)(Glutamate_2345/Glutamate)

dGlutamate_12345/dt=Glut_dil(NA_0/NA)+Glut_exc(aKG_12345/aKG)−(Glut_dil+Glut_exc)(Glutamate_12345/Glutamate)

Succinate dSuccinate_1/dt=0.5CS(aKG_12/aKG)+0.5CS(aKG_15/aKG)+0.5CS(aKG_5/aKG)+0.5CS(aKG_2/aKG)−CS(Succinate_1/Succinate)

dSuccinate_2/dt=0.5CS(aKG_4/aKG)+0.5CS(aKG_14/aKG)+0.5CS(aKG_3/aKG)+0.5CS(aKG_13/aKG)−CS(Succinate_2/Succinate)

dSuccinate_3/dt=0.5CS(aKG_4/aKG)+0.5CS(aKG_3/aKG)+0.5CS(aKG_13/aKG)+0.5CS(aKG_14/aKG)−CS(Succinate_3/Succinate)

dSuccinate_4/dt=0.5CS(aKG_5/aKG)+0.5CS(aKG_2/aKG)+0.5CS(aKG_12/aKG)+0.5CS(aKG_15/aKG)−CS(Succinate_4/Succinate)

dSuccinate_12/dt=0.5CS(aKG_23/aKG)+0.5CS(aKG_45/aKG)+0.5CS(aKG_145/aKG)+0.5CS(aKG_123/aKG)−CS(Succinate_12/Succinate)

dSuccinate_13/dt=0.5CS(aKG_24/aKG)+0.5CS(aKG_35/aKG)+0.5CS(aKG_124/aKG)+0.5CS(aKG_135/aKG)−CS(Succinate_13/Succinate)

dSuccinate_14/dt=CS(aKG_25/aKG)+CS(aKG_125/aKG)−CS(Succinate_14/Succinate)

dSuccinate_23/dt=CS(aKG_34/aKG)+CS(aKG_134/aKG)−CS(Succinate_23/Succinate)

dSuccinate_24/dt=0.5CS(aKG_35/aKG)+0.5CS(aKG_24/aKG)+0.5CS(aKG_124/aKG)+0.5CS(aKG_135/aKG)−CS(Succinate_24/Succinate)

dSuccinate_34/dt=0.5CS(aKG_45/aKG)+0.5CS(aKG_23/aKG)+0.5CS(aKG_145/aKG)+0.5CS(aKG_123/aKG)−CS(Succinate_34/Succinate)

dSuccinate_123/dt=0.5CS(aKG_234/aKG)+0.5CS(aKG_345/aKG)+0.5CS(aKG_1234/aKG)+0.5CS(aKG_1345/aKG)−CS(Succinate_123/Succinate)

dSuccinate_124/dt=0.5CS(aKG_235/aKG)+0.5CS(aKG_245/aKG)+0.5CS(aKG_1245/aKG)+0.5CS(aKG_1235/aKG)−CS(Succinate_124/Succinate)

dSuccinate_134/dt=0.5CS(aKG_235/aKG)+0.5CS(aKG_245/aKG)+0.5CS(aKG_1245/aKG)+0.5CS(aKG_1235/aKG)−CS(Succinate_134/Succinate)

dSuccinate_234/dt=0.5CS(aKG_234/aKG)+0.5CS(aKG_345/aKG)+0.5CS(aKG_1234/aKG)+0.5CS(aKG_1345/aKG)−CS(Succinate_234/Succinate)

dSuccinate_1234/dt=CS(aKG_12345/aKG)+CS(aKG_2345/aKG)−CS(Succinate_1234/Succinate)

Malate dMalate_1/dt=0.5CS(Succinate_1/Succinate)+0.5CS(Succinate_4/Succinate)+0.5SC(OAA_1/OAA)+0.5SC(OAA_4/OAA)−(CS+SC)(Malate_1/Malate)

dMalate_2/dt=0.5CS(Succinate_2/Succinate)+0.5CS(Succinate_3/Succinate)+0.5SC(OAA_2/OAA)+0.5SC(OAA_3/OAA)−(CS+SC)(Malate_2/Malate)

dMalate_3/dt=0.5CS(Succinate_3/Succinate)+0.5CS(Succinate_2/Succinate)+0.5SC(OAA_3/OAA)+0.5SC(OAA_2/OAA)−(CS+SC)(Malate_3/Malate)

dMalate_4/dt=0.5CS(Succinate_1/Succinate)+0.5CS(Succinate_4/Succinate)+0.5SC(OAA_4/OAA)+0.5SC(OAA_1/OAA)−(CS+SC)(Malate_4/Malate)

dMalate_12/dt=0.5CS(Succinate_12/Succinate)+0.5CS(Succinate_34/Succinate)+0.5SC(OAA_12/OAA)+0.5SC(OAA_34/OAA)−(CS+SC)(Malate_12/Malate)

dMalate_13/dt=0.5CS(Succinate_13/Succinate)+0.5CS(Succinate_24/Succinate)+0.5SC(OAA_13/OAA)+0.5SC(OAA_24/OAA)−(CS+SC)(Malate_13/Malate)

dMalate_14/dt=CS(Succinate_14/Succinate)+SC(OAA_14/OAA)−(CS+SC)(Malate_14/Malate)

dMalate_23/dt=CS(Succinate_23/Succinate)+SC(OAA_23/OAA)−(CS+SC)(Malate_23/Malate)

dMalate_24/dt=0.5CS(Succinate_24/Succinate)+0.5CS(Succinate_13/Succinate)+0.5SC(OAA_24/OAA)+0.5SC(OAA_13/OAA)−(CS+SC)(Malate_24/Malate)

dMalate_34/dt=0.5CS(Succinate_34/Succinate)+0.5CS(Succinate_12/Succinate)+0.5SC(OAA_12/OAA)+0.5SC(OAA_34/OAA)−(CS+SC)(Malate_34/Malate)

dMalate_123/dt=0.5CS(Succinate_123/Succinate)+0.5CS(Succinate_234/Succinate)+0.5SC(OAA_123/OAA)+0.5SC(OAA_234/OAA)    (CS+SC)(Malate_123/Malate)

dMalate_234/dt=0.5CS(Succinate_234/Succinate)+0.5CS(Succinate_123/Succinate)+0.5SC(OAA_123/OAA)+0.5SC(OAA_234/OAA)    (CS+SC)(Malate_234/Malate)

dMalate_124/dt=0.5CS(Succinate_124/Succinate)+0.5CS(Succinate_134/Succinate)+0.5SC(OAA_124/OAA)+0.5SC(OAA_134/OAA)    (CS+SC)(Malate_124/Malate)

dMalate_134/dt=0.5CS(Succinate_134/Succinate)+0.5CS(Succinate_124/Succinate)+0.5SC(OAA_134/OAA)+0.5SC(OAA_124/OAA)    (CS+SC)(Malate_134/Malate)

dMalate_1234/dt=CS(Succinate_1234/Succinate)+SC(OAA_1234/OAA)−(CS+SC)(Malate_1234/Malate)

OAA dOAA_123/dt=PC(Pyruvate_123/Pyruvate)+0.5(CS+SC)(Malate_123/Malate)+0.5(CS+SC)(Malate_234/Malate)−(CS+PEP/Pyr_cycling+SC)(OAA_123/OAA)

dOAA_234/dt=PC(NA_0/NA)+0.5(CS+SC)(Malate_234/Malate)+0.5(CS+SC)(Malate_123/Malate)−(CS+PEP/Pyr_cycling+SC)(OAA_234/OAA)

dOAA_124/dt=PC(NA_0/NA)+0.5(CS+SC)(Malate_124/Malate)+0.5(CS+SC)(Malate_134/Malate)−(CS+PEP/Pyr_cycling+SC)(OAA_124/OAA)

dOAA_134/dt=PC(NA_0/NA)+0.5(CS+SC)(Malate_134/Malate)+0.5(CS+SC)(Malate_124/Malate)−(CS+PEP/Pyr_cycling+SC)(OAA_134/OAA)

dOAA_1234/dt=PC(NA_0/NA)+(CS+SC)(Malate_1234/Malate)−(CS+PEP/Pyr_cycling+SC)(OAA_1234/OAA)

dOAA_12/dt=PC(Pyruvate_12/Pyruvate)+0.5(CS+SC)(Malate_12/Malate)+0.5(CS+SC)(Malate_34/Malate)−(CS+PEP/Pyr_cycling+SC)(OAA_12/OAA)

dOAA_34/dt=PC(NA_0/NA)+0.5(CS+SC)(Malate_12/Malate)+0.5(CS+SC)(Malate_34/Malate)−(CS+PEP/Pyr_cycling+SC)(OAA_34/OAA)

dOAA_13/dt=PC(Pyruvate_13/Pyruvate)+0.5(CS+SC)(Malate_13/Malate)+0.5(CS+SC)(Malate_24/Malate)−(CS+PEP/Pyr_cycling+SC)(OAA_13/OAA)

dOAA_14/dt=PC(NA_0/NA)+(CS+SC)(Malate_14/Malate)−(CS+PEP/Pyr_cycling+SC)(OAA_14/OAA)

dOAA_23/dt=PC(Pyruvate_23/Pyruvate)+(CS+SC)(Malate_23/Malate)−(CS+PEP/Pyr_cycling+SC)(OAA_23/OAA)

dOAA_24/dt=PC(NA_0/NA)+0.5(CS+SC)(Malate_24/Malate)+0.5(CS+SC)(Malate_13/Malate)−(CS+PEP/Pyr_cycling+SC)(OAA_24/OAA)

dOAA_1/dt=PC(Pyruvate_1/Pyruvate)+0.5(CS+SC)(Malate_1/Malate)+0.5(CS+SC)(Malate_4/Malate)−(CS+PEP/Pyr_cycling+SC)(OAA_1/OAA)

dOAA_2/dt=PC(Pyruvate_2/Pyruvate)+0.5(CS+SC)(Malate_2/Malate)+0.5(CS+SC)(Malate_3/Malate)−(CS+PEP/Pyr_cycling+SC)(OAA_2/OAA)

dOAA_3/dt=PC(Pyruvate_3/Pyruvate)+0.5(CS+SC)(Malate_3/Malate)+0.5(CS+SC)(Malate_2/Malate)−(CS+PEP/Pyr_cycling+SC)(OAA_3/OAA)

dOAA_4/dt=PC(NA_0/NA)+0.5(CS+SC)(Malate_1/Malate)+0.5(CS+SC)(Malate_4/Malate)−(CS+PEP/Pyr_cycling+SC)(OAA_4/OAA)

As shown by the equations above, a model may be developed that generates and describes the reactions giving rise to all possible isotopomers for the considered metabolites. The time courses of citrate, glutamate, succinate, malate and OAA enrichments may be used as target data.

It may be beneficial in at least some cases to use individual isotopomers as target data where possible. In some instances, however, the lack of position-specific labeling information from certain fragments may not allow such an approach (e.g., the cases of succinate, malate and OAA $M^{+2}$ enrichments). In such instances, this issue may be resolved by creating combined pools for each metabolite containing all the isotopomers with two labeled carbons.

To perform a flux analysis, the rates of $V_{PDH}$, $V_{PC}$, $V_{ICDH}$ and $v_{Glut_{on}}$ may be allowed to vary freely in order to obtain a best fit to these time courses.

Having thus described several aspects of at least one embodiment of this invention, it is to be appreciated that various alterations, modifications, and improvements will readily occur to those skilled in the art.

Such alterations, modifications, and improvements are intended to be part of this disclosure, and are intended to be within the spirit and scope of the invention. Further, though advantages of the present invention are indicated, it should be appreciated that not every embodiment of the technology described herein will include every described advantage. Some embodiments may not implement any features described as advantageous herein and in some instances one or more of the described features may be implemented to achieve further embodiments. Accordingly, the foregoing description and drawings are by way of example only.

Also, various inventive concepts may be embodied as one or more methods, of which examples have been provided. The acts performed as part of a method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. A spectrometer, configured to:
receive molecules of a plurality of metabolites including one or more molecules of a first metabolite;
filter the received molecules to retain molecules of the first metabolite including a plurality of different mass isotopomers of the first metabolite;
fragment molecules of a first mass isotopomer of the retained molecules to produce a first plurality of daughter ions;
measure abundances of the first plurality of daughter ions as a function of daughter ion mass;
fragment molecules of a second mass isotopomer, different from the first mass isotopomer, of the retained molecules to produce a second plurality of daughter ions; and
measure abundances of the second plurality of daughter ions as a function of daughter ion mass.

2. The spectrometer of claim 1, wherein the spectrometer is configured to perform said filtering based at least in part on a mobility of the received molecules.

3. The spectrometer of claim 2, wherein the spectrometer is configured to perform said filtering via ion-mobility spectrometry.

4. The spectrometer of claim 3, wherein the spectrometer is configured to perform said filtering via differential mobility spectrometry (DMS).

5. The spectrometer of claim 1, wherein the spectrometer is configured to perform said fragmenting steps and said measuring steps via tandem mass spectrometry.

6. The spectrometer of claim 5, wherein the spectrometer is configured to perform said fragmenting steps and said measuring steps via multiple reaction monitoring (MRM).

7. A system comprising:
the spectrometer of claim 1; and
at least one processor configured to:
receive indications of the measured abundances of the first and second pluralities of daughter ions from the spectrometer; and
determine a metabolic flux for the first metabolite based at least in part on the received indications.

8. The system of claim 7, wherein the at least one processor is further configured to perform a correction to the received indications of the measured abundances based on a process in which isocitrate dehydrogenase (ICDH) reacts with isocitrate.

9. The system of claim 7, wherein the at least one processor is further configured to perform a correction to the received indications of the measured abundances based on a natural abundance of carbon-13.

10. The system of claim 7, wherein the determined metabolic flux comprises a plurality of conversion rates to the first metabolite from metabolites of the plurality of metabolites other than the first metabolite.

11. The system of claim 7, wherein determining the metabolic flux for the first metabolite comprises determining an abundance of a group of positional isotopomers of the first mass isotopomer.

12. A method, comprising:
receiving molecules of a plurality of metabolites including one or more molecules of a first metabolite;
filtering the received molecules to retain molecules of the first metabolite including a plurality of different mass isotopomers of the first metabolite;
fragmenting molecules of a first mass isotopomer of the retained molecules to produce a first plurality of daughter ions;
measuring abundances of the first plurality of daughter ions as a function of daughter ion mass;
fragmenting molecules of a second mass isotopomer, different from the first mass isotopomer, of the retained molecules to produce a second plurality of daughter ions;
measuring abundances of the second plurality of daughter ions as a function of daughter ion mass.

13. The method of claim 12, wherein the received molecules include citrate, pyruvate, aspartate, malate, succinate and glutamate.

14. The method of claim 12, wherein the molecules of the first metabolite include a plurality of isotopologues of the first metabolite.

15. The method of claim 14, wherein the molecules of the first metabolite include a plurality of carbon-13 enriched molecules.

16. The method of claim 12, further comprising introducing a source of carbon-13 to the molecules of the plurality of metabolites.

17. The method of claim 16, further comprising determining metabolic fluxes for the first metabolite at a plurality of time points subsequent to the introduction of the source of carbon-13.

18. The method of claim 12, further comprising determining a metabolic flux for the first metabolite based at least in part on the measured abundances.

19. The method of claim 12, further comprising introducing a plurality of effector molecules to the molecules of the plurality of metabolites.

20. The method of claim 19, further comprising determining metabolic fluxes for the first metabolite at a plurality of time points subsequent to the introduction of the plurality of effector molecules.

* * * * *